United States Patent
Kaufman et al.

(10) Patent No.: US 11,202,703 B2
(45) Date of Patent: Dec. 21, 2021

(54) SPEECH ASSISTANCE DEVICE AND METHOD

(71) Applicant: GEORGIA SPEECH AND SWALLOWING, LLC, Dunwoody, GA (US)

(72) Inventors: Meryl L. Kaufman, Dunwoody, GA (US); J. Noah McNeely, Grayson, GA (US); Donald A. Muntner, Hoschton, GA (US)

(73) Assignee: Georgia Speech and Swallowing, LLC, Dunwoody, GA (US)

( * ) Notice: Subject to any disclaimer, the term of this patent is extended or adjusted under 35 U.S.C. 154(b) by 0 days.

(21) Appl. No.: 16/505,898

(22) Filed: Jul. 9, 2019

(65) Prior Publication Data
US 2020/0008933 A1     Jan. 9, 2020

Related U.S. Application Data

(60) Provisional application No. 62/695,512, filed on Jul. 9, 2018.

(51) Int. Cl.
*A61F 2/20*     (2006.01)

(52) U.S. Cl.
CPC .......... *A61F 2/20* (2013.01); *A61F 2002/206* (2013.01); *A61F 2220/0033* (2013.01); *A61F 2250/0069* (2013.01)

(58) Field of Classification Search
CPC ........ A61F 2/20; A61F 2/04; A61F 2002/206; A61F 2002/481; A61F 2002/6809; A61F 2002/0069
See application file for complete search history.

(56) References Cited

U.S. PATENT DOCUMENTS

| | | | |
|---|---|---|---|
| 1,867,350 A | 7/1932 | Burchett | |
| 1,910,966 A * | 5/1933 | Riesz | A61F 2/20 623/9 |
| 2,024,601 A | 12/1935 | Riesz | |
| 3,066,186 A | 11/1962 | Trammell | |

(Continued)

FOREIGN PATENT DOCUMENTS

| | | |
|---|---|---|
| CN | 201399015 | 2/2010 |
| CN | 201968865 | 9/2011 |

(Continued)

OTHER PUBLICATIONS

Brook, Itzhak. "The Laryngectomee Guide," Jul. 29, 2013; CreateSpace Publication. (Year: 2013).*

(Continued)

*Primary Examiner* — Yashita Sharma
*Assistant Examiner* — Amanda M Barkan
(74) *Attorney, Agent, or Firm* — ayor English Duma LLP

(57) ABSTRACT

A speech assistance device includes: an adaptor defining a first end and a second end, a first end of the adaptor configured to cover and seal directly or indirectly against a tracheal stoma defined in a neck of a user, the adaptor comprising a compressible material; a reed module connected to the adaptor, the reed module including a reed configured to produce sound using air expelled by the user from the stoma; and a tube coupled to the reed module, the tube configured to be inserted into a mouth of the user.

21 Claims, 29 Drawing Sheets

(56) References Cited

U.S. PATENT DOCUMENTS

| | | | |
|---|---|---|---|
| 4,264,989 A | | 5/1981 | Wiley |
| 4,494,252 A | * | 1/1985 | Chaoui .................. A61F 2/203 128/207.16 |
| 4,821,326 A | | 4/1989 | MacLeod |
| 5,910,039 A | | 6/1999 | Primos et al. |
| 8,771,350 B2 | | 7/2014 | Huang |
| 2013/0017755 A1 | | 1/2013 | Hooks |
| 2016/0182994 A1 | | 6/2016 | Korch-Haahr et al. |

FOREIGN PATENT DOCUMENTS

| KR | 20040084058 | 10/2004 |
|---|---|---|
| WO | 1991016011 | 10/1991 |
| WO | 2020014216 | 1/2020 |

OTHER PUBLICATIONS

Green, et al.; American Speech-Language-Hearing Association; Article entitled: "Preferences for Three Types of Alaryngeal Speech", Journal of Speech and Hearing Disorders, vol. 47, 141-145, May 1982, 5 pgs.

Chalstrey, et al.; Cambridge Core; Article entitled: "A pneumatic artificial larynx popularized in Hong Kong", The Journal of Laryngology and Otology, Oct. 1994, vol. 108, pp. 852-854, 3 pgs.

Kaye, et al.; Dovepress; Article entitled: "The electrolarynx: voice restoration after total laryngectomy", Medical Devices: Evidence and Research 2017:10 133-140, published Jun. 21, 2017, 8 pgs.

Electrolarynx speech sample on YouTube, available at <https://www.youtube.com/watch?v=riHLUOXt1Aw&t=20s>, published Sep. 26, 2012.

Ooe, et al.; Elsevier; Article entitled: "Development of Controllable Artificial Larynx by Neck Myoelectric Signal", available at <www.sciencedirect.com>, Procedia Engineering 47 ( 2012 ) 869-872, published Sep. 9-12, 2012, 4 pgs.

Esophageal speech sample on YouTube, available at <https://www.youtube.com/watch?v=kyN_NFoBfiw>, published Dec. 24, 2013.

Nelson, et al.; Article entitled: "The Modified Tokyo Larynx", Arch Otolaryngol/vol. 101, Feb. 1975, 2 pgs.

New Atlas; "Article entitled: Respiratory-driven, non-surgical artificial larynx produces more human voice", located at <https://newatlas.com/prosthetic-artificial-larynx-restores-voice-laryngectomy/53519/>, published Feb. 24, 2018, 6 pgs.

Ng, et al.; Article entitled: "Speech Performance of Adult Cantonese-Speaking Laryngectomees Using Different Types of Alaryngeal Phonation", Journal of Voice, vol. II. No. 3, pp. 338-344, copyright 1997, 7 pgs.

Plos One; Article entitled: "A pneumatic Bionic Voice prosthesis—Pre-clinical trials of controlling the voice onset and offset", located at <https://doi.org/10.1371/journal.pone.0192257>, published Feb. 21, 2018, 20 pgs.

Tokyo Pneumatic Speech Aid speech sample on Facebook; available at <https://www.facebook.com/John.Isler.III/videos/1936271946653699/?hc_location=ufi>, published Jun. 28, 2017.

Tracheoesophageal Voice Prosthesis (TEP) speech sample on YouTube, available at <https://www.youtube.com/watch?v=XJgPOpmhOKA>, published Nov. 23, 2011.

Ultravoice; Article entitled: "How It Works", located at <https://www.ultravoice.com/electrolarynx-speech-device-works/>, publicly available prior to Jul. 9, 2018, 4 pgs.

Webwhispers; Article entitled: "Electrolarynx", located at <http://www.webwhispers.org/library/Electrolarynx.asp>, accessed on Apr. 26, 2018, 12 pgs.

Webwhispers; Article entitled: "Nat Quick—Laryngectomee Artist", located at <http://www.webwhispers.org/news/dec2002.htm>, published Dec. 2002, 9 pgs.

Webwhispers; Article entitled: "Whispers on the web", located at <http://www.webwhispers.org/news/oct2004.htm>, published Oct. 2004, 16 pgs.

Western Sydney University; Article entitled: "Discovery to alter the path of bionic voice research worldwide", located at <https://www.westernsydney.edu.au/newscentre/news_centre/more_news_stories/discovery>, published Feb. 22, 2018, 2 pgs.

Wikipedia; Article entitled: "Heat and moisture exchanger after laryngectomy", located at <https://en.wikipedia.org/wiki/Heat_and_moisture_exchanger_after_laryngectomy>, last edited on Nov. 13, 2016, 3 pgs.

Kaufman, Meryl L.; Invitation to Pay Additional Fees for PCT/US19/40989, filed Jul. 9, 2019, mailed Sep. 13, 2019, 2 pgs.

Ultravoice electrolarynx speech sample, available at <https://www.ultravoice.com/electrolarynx-device-voice-sample/>, published Jun. 8, 2016.

Kaufman, Meryl L.; International Search Report and Written Opinion for PCT Application No. PCT/US19/40989, filed Jul. 9, 2019, dated Nov. 18, 2019, 13 pgs.

Kaufman, Meryl L.; International Preliminary Report on Patentability for PCT Application No. PCT/US19/40989, filed Jul. 9, 2019, dated Jan. 21, 2021, 10 pgs.

\* cited by examiner

SPEECH ASSISTANCE DEVICE AND METHOD

REFERENCE TO RELATED APPLICATIONS

This application claims the benefit of U.S. Provisional Application No. 62/695,512, filed Jul. 9, 2018, which is hereby specifically incorporated by reference herein in its entirety.

TECHNICAL FIELD

Field of Use

This disclosure relates to a speech aid or speech assistance device for laryngectomy patients. More specifically, this disclosure relates to speech aids that mimic or in other ways substitute for a natural human voice lost with the removal of a larynx.

Related Art

Laryngectomy patients, or laryngectomees, are those whose larynx or vocal cords have been removed (a procedure sometimes also described as a total laryngectomy). While such removal can be for a variety of reasons, occurrence of a disease such as cancer is often an underlying factor. Laryngectomees can sometimes have warning of the conditions or at least the surgery leading to larynx removal, but in any case the effect can be devastating on such an individual's ability to effectively, naturally, and efficiently communicate with family, friends, colleagues, and others.

Some methods for communication after laryngectomy, while natural and effective can require regular and very expensive follow-up by health care professionals—often a team of doctors, nurses, and/or speech language pathologists—and are not possible in all circumstances and can for some be prohibitively expensive—easily costing the laryngectomee hundreds or thousands of dollars for each device, procedure, or visit. Most alternative methods of communication after laryngectomy, while varying significantly in quality, cost, and availability, can produce speech that, rather than mimicking natural human speech, sounds "electronic" or "robotic." Such speech can be difficult for many who depend on a more natural voice in their career, family, community, and other activities.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

In one aspect, disclosed is a speech assistance device comprising: an adaptor defining a first end and a second end, the first end of the adaptor configured to cover and seal directly or indirectly against a tracheal stoma defined in a neck of a user, the adaptor comprising a compressible material; a reed module connected to the adaptor, the reed module comprising a reed configured to produce sound using air expelled by the user from the stoma; and a tube coupled to the reed module, the tube configured to be inserted into a mouth of the user.

In a further aspect, disclosed is a speech assistance device comprising: a monolithic body comprising a tube configured to be inserted into a mouth of a user; the body defining a reed module cavity, a reed module positioned within the reed module cavity of the body, the reed module comprising a reed; and an adaptor configured to cover and seal directly or indirectly against a tracheal stoma defined in a neck of the user, the adaptor comprising a compressible material.

In yet another aspect, disclosed is a method of using a speech assistance device, the method comprising: sealing against leakage at a connection between a first end of an adaptor of the device and an air source, the first end of the adaptor comprising a compressible material; and generating with the device a first vibratory sound defining a first set of characteristics, the device generating the first vibratory sound with a first reed module incorporated therein, the first reed module comprising a first reed, the device further comprising: an adaptor defining a first end and a second end, the first reed module connected to the adaptor; and a tube connected to the reed module, the tube configured to be inserted into a mouth of a user.

In yet another aspect, disclosed is a speech assistance device comprising: a body comprising an ear attachment hook, the ear attachment hook configured to secure the body to an ear of a user; a tube coupled to the body, the tube configured to be inserted into a mouth of the user; and a speaker coupled to the tube and configured to transmit vibrations through the tube to an oral cavity of the user.

In yet another aspect, disclosed is a speech assistance device comprising: a body comprising an ear attachment hook, the ear attachment hook configured to secure the body to an ear of a user; and a speaker configured to contact a skin surface of the user to transmit vibrations through the skin surface to an oral cavity of the user.

In yet another aspect, disclosed is a speech assistance device comprising: a body comprising an open ring configured to be worn around the neck of a user; a tube coupled to the body, the tube configured to be inserted into a mouth of the user; and a speaker coupled to the tube and configured to transmit vibrations through the tube to an oral cavity of the user.

In yet another aspect, disclosed is a speech assistance device comprising: a body comprising an open ring configured to be worn around a neck of a user; and a speaker coupled to the body and configured to contact a skin surface of the user to transmit vibrations through the skin surface to an oral cavity of the user.

In yet another aspect, disclosed is a speech assistance device comprising: a disc configured to be affixed to a neck of a user, the disc comprising a sound transducer; and a portable electronic device in wireless communication with the disc, the portable electronic device configured to produce audio signals resembling speech.

Various implementations described in the present disclosure may comprise additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims. The features and advantages of such implementations may be realized and obtained by means of the systems, methods, features particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

The accompanying drawings, which are incorporated in and constitute a part of this specification, illustrate several aspects of the disclosure and together with the description, serve to explain various principles of the disclosure. The drawings are not necessarily drawn to scale. Corresponding features and components throughout the figures may be designated by matching reference characters for the sake of consistency and clarity.

DETAILED DESCRIPTION

Figure 1:
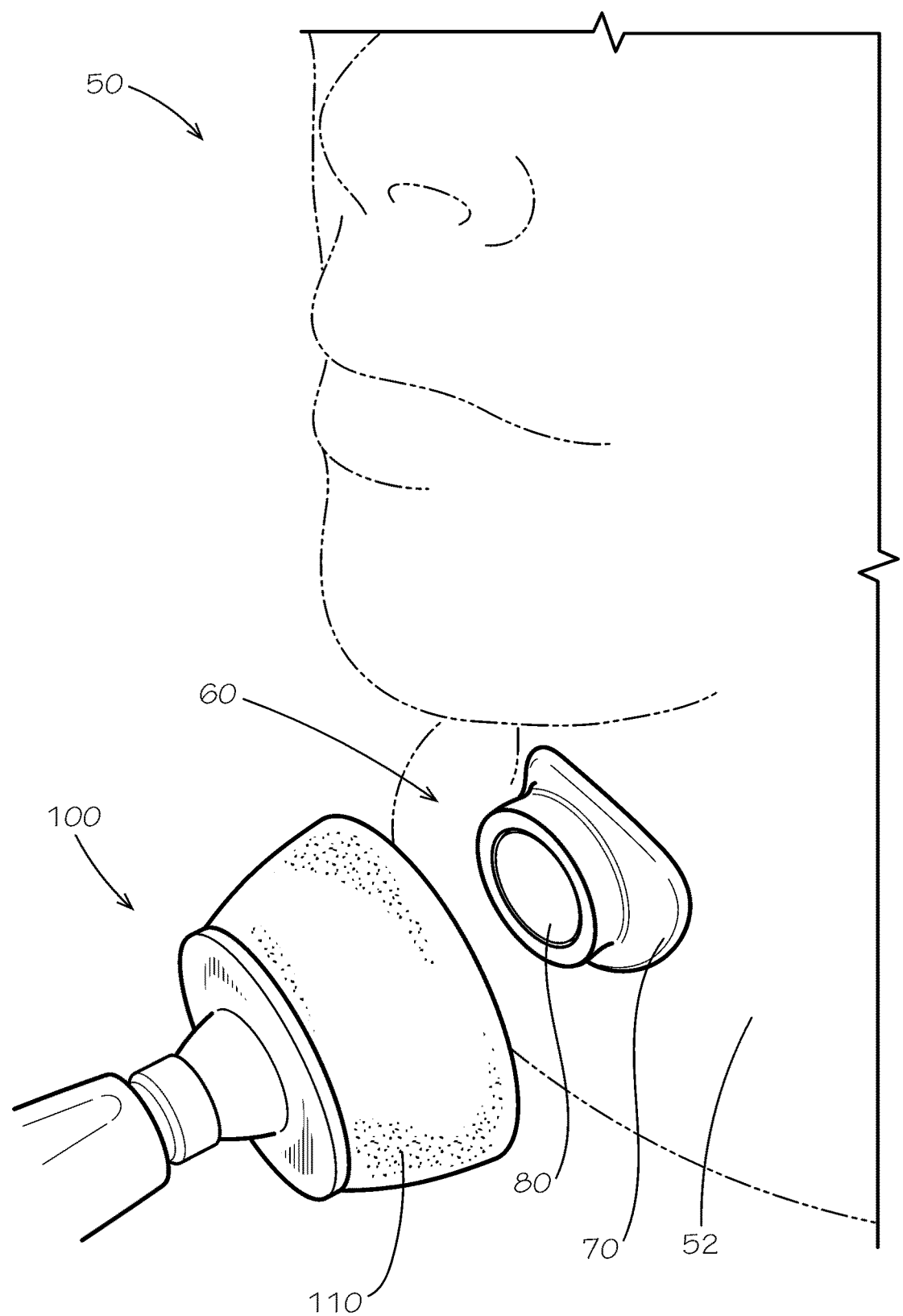
FIG. 1 is a perspective view of a neck of a user and a speech assistance device in accordance with one aspect of the current disclosure showing a first end of the device proximate to and facing a stoma defined in a neck of the user, the stoma covered by a heat and moisture exchange (HME) cassette.

The present disclosure can be understood more readily by reference to the following detailed description, examples, drawings, and claims, and their previous and following description. However, before the present devices, systems, and/or methods are disclosed and described, it is to be understood that this disclosure is not limited to the specific devices, systems, and/or methods disclosed unless otherwise specified, as such can, of course, vary. It is also to be understood that the terminology used herein is for the purpose of describing particular aspects only and is not intended to be limiting.

The following description is provided as an enabling teaching of the present devices, systems, and/or methods in their best, currently known aspect. To this end, those skilled in the relevant art will recognize and appreciate that many changes can be made to the various aspects described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to a quantity of one of a particular element can comprise two or more such elements unless the context indicates otherwise. In addition, any of the elements described herein can be a first such element, a second such element, and so forth (e.g., a first widget and a second widget, even if only a "widget" is referenced).

Ranges can be expressed herein as from "about" one particular value, and/or to "about" another particular value. When such a range is expressed, another aspect comprises from the one particular value and/or to the other particular value. Similarly, when values are expressed as approximations, by use of the antecedent "about" or "substantially," it will be understood that the particular value forms another aspect. It will be further understood that the endpoints of each of the ranges are significant both in relation to the other endpoint, and independently of the other endpoint.

For purposes of the current disclosure, a material property or dimension measuring about X or substantially X on a particular measurement scale measures within a range between X plus an industry-standard upper tolerance for the specified measurement and X minus an industry-standard lower tolerance for the specified measurement. Because tolerances can vary between different materials, processes and between different models, the tolerance for a particular measurement of a particular component can fall within a range of tolerances.

As used herein, the terms "optional" or "optionally" mean that the subsequently described event or circumstance may or may not occur, and that the description comprises instances where said event or circumstance occurs and instances where it does not.

The word "or" as used herein means any one member of a particular list and also comprises any combination of members of that list.

To simplify the description of various elements disclosed herein, the conventions of "left," "right," "front," "rear," "top," "bottom," "upper," "lower," "inside," "outside," "inboard," "outboard," "horizontal," and/or "vertical" may be referenced. Unless stated otherwise, "front" describes that end of the device nearest to or facing a portion of the device nearest to the front of a user of the device; "rear" is that end of the device that is opposite or distal the front; "left" and "right" are from the perspective of the user. "Horizontal" or "horizontal orientation" describes that which is in a plane extending from left to right and aligned with the horizon. "Vertical" or "vertical orientation" describes that which is in a plane that is angled at 90 degrees to the horizontal.

In one aspect, a speech assistance device and associated methods, systems, devices, and various apparatuses are disclosed herein. In one aspect, the speech assistance device can comprise a reed or a speaker.

Human speech comes in various forms and typically requires and involves three elements: a pulmonary source or air generator—typically the lungs, a sound source or vibrating apparatus—typically a larynx located proximate to an outlet of the lungs, and a modulating device or articulating tract, which can comprise any of the cavities through which sound produced by the larynx can travel before exiting the body. The most common or natural form of human speech makes use of the larynx or "voice box" and involves the forceful flow of air blown through the trachea from the lungs and across vocal folds of the larynx, which are sometimes referred to also as "vocal cords." The vibration of the vocal folds results in a usually audible sound wave that is then modulated by a pharynx (the tract through which the air flows after leaving the larynx but before entering an oral cavity of a human), the oral cavity including through manipulation of the tongue, teeth, and lips, and in some cases the nasal cavity. Each of the oral cavity and the nasal cavity can be considered a resonating cavity in which sound produced elsewhere can resonate.

Whenever any of the aforementioned elements necessary for human speech is compromised or missing, such as is the case for laryngectomy patients, other forms of speech may be required. For example, without the human vocal cords, another "vibrating apparatus" or sound source can become necessary. It can be possible to produce speech without the larynx using one of the common forms of alaryngeal speech, of which there are at least the following two types: esophageal speech and buccal speech. Esophageal speech, shown in FIG. 48, can be extremely difficult or impossible to master and involves swallowing or injecting air into the upper esophagus and then speaking while "burping" up that same air. It requires significant skill and patience and allows one to speak only a few words at a time. Buccal speech, popularized by the voice actor behind the Disney character Donald Duck, involves squeezing air inside one's mouth to produce a sound, which can be modulated as other speech but is also difficult to produce and not a practical option. Outside of these categories, however, laryngectomees have three other main options, each of which involves the use of an artificial speech aid: a so-called electrolarynx, a pneumatic speech aid, and tracheoesophageal voice prosthesis (TEP).

The typical electrolarynx is basically a small hand-held and typically battery powered electromechanical device that produces vibrations that, when the device is held against the neck or check or inserted into the oral cavity via an oral adaptor or tubing, can produce sound through manipulations of the oral cavity to modulate that sound and form intelligible speech.

The typical pneumatic device—a variation of which is or at least was popularly known as the Tokyo device—directs air from the lungs, its primary air generator, from a stoma defined in the neck of a patient into and through a rigid bypass tube with a single fixed reed housed therein. The tube carries the air and sound generated by the reed to the mouth for modulation inside the oral cavity, but from an end proximate to the stoma to an end proximate to the mouth of the user—and including the reed therebetween—the typical pneumatic device lacks the adjustability necessary to accommodate the needs of different users. For example, the reed or closest corresponding structure, if any, of the typical device is not configured to be adjustable or interchangeable, and neither end of the device is configured to accommodate the varying physiological differences of users (including, e.g., the varying neck, stoma, and neck accessory shapes and sizes) and various usage preferences. Moreover, some neck accessories and conditions have developed or have been developed since when the Tokyo device was in existence or at least created, and this and similar pneumatic devices are in some if not all cases no longer in production or on sale.

The TEP involves surgically placing in the common wall between the trachea and the esophagus or through a reconstruction of various types that may be required in extended or total laryngectomy (TL)—a small device designed to direct air from the trachea through the prosthesis in the common wall to the esophagus and pharynx (or the reconstruction) to vibrate the esophagus and pharynx and produce sound that is then transmitted into the mouth for speech. The patient closes off the stoma with, e.g., a finger, forcing the air from the lungs through the TEP into the esophagus and pharynx (or the reconstruction). In any case, as will be described, many patients cover the stoma with a heat and moisture exchange (HME) cassette 80 (shown in FIG. 1) for hygiene, comfort, and safety. More specifically, the HME cassette 80 can be any device that interfaces with the stoma to filter, humidify/dehumidify, or otherwise process air 90 (shown in FIG. 24) passing through (into or out of) the stoma 58 (shown in FIG. 48). Many other patients, however, due to financial lack or poor access to health care live regularly with no neck accessory 60 or HME cassette 80 covering the stoma 58.

As noted above, some of these alternative methods are not available for use by some patients, are prohibitively expensive, or simply do not work reliably. One of the most affordable speech aids, the pneumatic device, requires no surgery, no batteries, and can be relatively easy to learn. A typical pneumatic device will not, however, fit over the HME cassette 80 and has never been used widely for various functional and aesthetic issues with the variations available heretofore. In addition, where the typical pneumatic device covered or mated with the stoma 58, such a device was typically formed from a rigid material such as metal. Moreover, as noted above, in some markets such as in the United States such devices are no longer even available for general sale to the public, if at all. Even when successful at producing speech, the speech produced by an electrolarynx can, rather than mimicking natural human speech, sound "electronic" or "robotic." The TEP, while producing what is considered by some to be the highest quality and most naturally sounding human speech available using existing methods, not only requires additional surgery and regular maintenance visits to a health care provider but is not available to some patients, especially those whose treatment results extensive damage to the tissue in the area where the TEP would be installed. Even patients with insurance or similar financial support increasingly cannot receive reimbursement for TEP. Whatever the reason, speech can be difficult for many who depend on a more natural voice—or a voice at all—in their career, family, community, and other activities. Those with more limited means can be without good options altogether.

Because, by some estimates, approximately 3,000 laryngectomies are performed each year in the U.S. alone and approximately 50,000 to 60,000 laryngectomees live in the U.S. alone, the need for improved forms of speech assistance is significant.

The various aspects described herein can be viewed as incorporating elements of one or more of the methods used by other artificial speech aids but in ways that improve one or more aspects of the speech process.

As shown in FIG. 1, a neck 52 of a user 50, which can be a laryngectomy patient, can define a stoma 58 (shown in FIG. 2), which can be a tracheal stoma in that it can be an opening created from the resected trachea proximate to a front of the neck 52. A medical professional or, in some cases, the user 50 herself can affix or install a neck accessory 60 to cover the stoma 58, the exposure of which might otherwise cause issues to the user due to the introduction of contaminating substances or unfiltered air or due to the loss of humidity therein. The neck accessory 60 can be any device configured to interface with the stoma 58 for functional reasons or aesthetic reasons (or both) and can comprise any one or more of a base plate 70, a "tube," a "button," or any equivalent structure. The neck accessory 60 can be sized to receive the HME cassette 80, and the neck accessory 60 can be received within or about the stoma 58.

The base plate 70, which can either receive the HME cassette 80 or incorporate the HME cassette 80 in a monolithic structure, can define an inner surface facing the neck 52 of the user 50 and an outer surface distal from the inner surface and facing outward away from the neck 52. In some aspects, as shown, either or both of the inner surface and the outer surface can be curved or flat to match the contour of the neck 52 as desired. In other aspects, either or both of the inner surface and the outer surface can be curved or flat to match the profile of a speech assistance device 100 as desired. Not only the base plate 70 but any of the other neck accessories 60 including the aforementioned button or the aforementioned tube can extend a distance through the stoma to support the stoma and the trachea and, again, can receive the HME cassette 80. As shown in FIG. 1 and also FIG. 24, a portion of the neck accessory 60 can extend beyond an outer diameter of the HME cassette 80.

In some aspects, as will be described later, the device 100, which can also be a speech aid, can be used by the user 50 to facilitate the production of speech while in communication with the stoma 58 or by any one of a number of other structures and methods described below. More specifically, an adaptor 110 of the device 100 can be configured to cover and seal against the stoma 58 of the user 50, including when the stoma is fitted with the neck accessory 60 comprising the HME cassette 80. More specifically, an inner diameter D115 (shown in FIG. 3) of a cavity 115 (shown in FIG. 3) of the adaptor 110 can be sized to receive the HME cassette 80 including when a portion of the HME cassette 80 protrudes from the neck 52 of the user 50. The adaptor 100 can also be sized to receive any structure surrounding the HME cassette 80 such as, for example and without limitation, the neck accessory 60, In other aspects, no communication between the device 100 and the stoma 58 is necessary. For example and without limitation, in some aspects, as with an electrolarynx, no pulmonary source is necessary.

Figure 2:
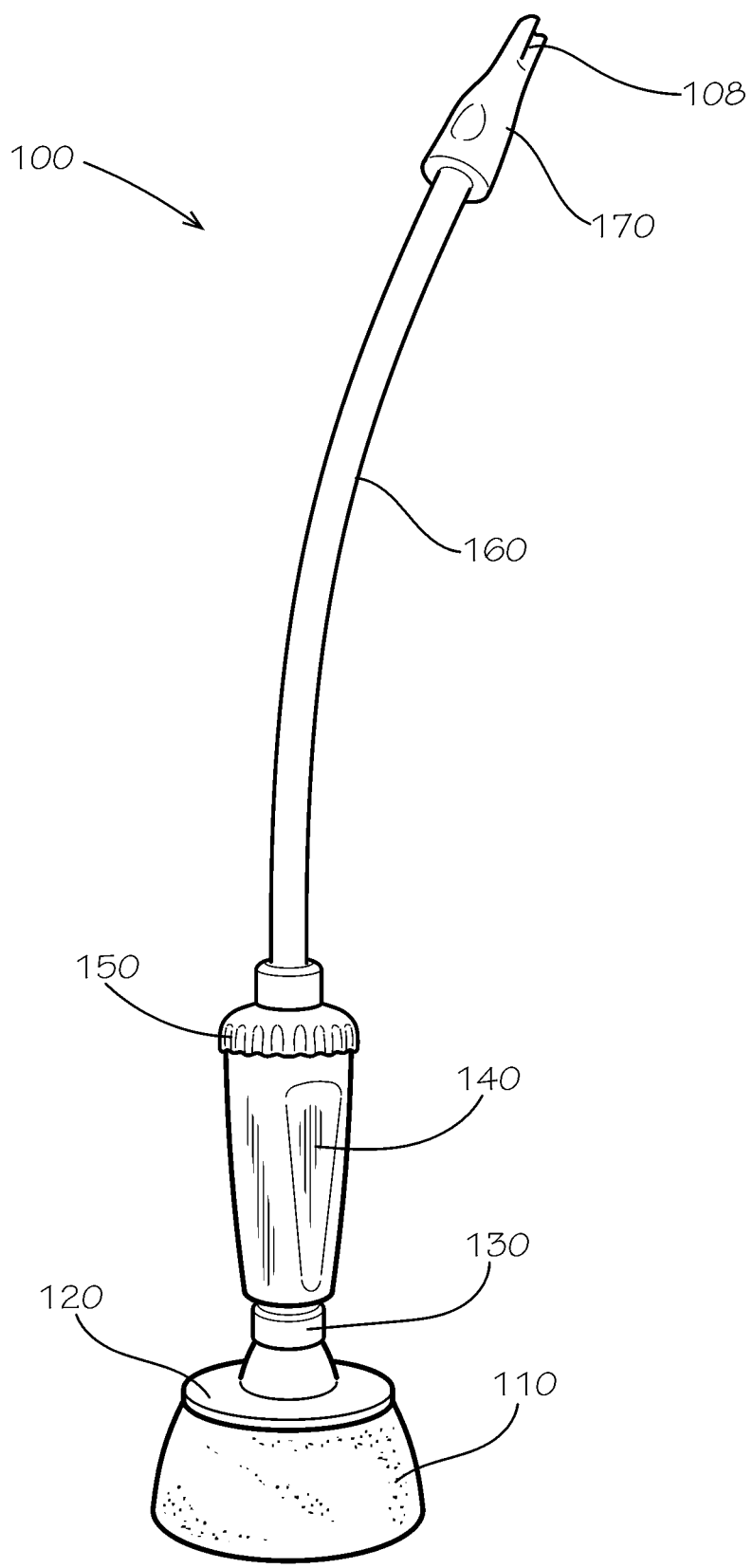
FIG. 2 is a full side perspective view of the speech assistance device of FIG. 1.

As shown in FIGS. 2-19, the device 100 can be of a "durable" configuration comprising parts that can, as desired, be assembled, disassembled, and/or modified as a need or desire may arise to replace individual parts. As shown in FIG. 2, the device 100 can comprise any one or more of an adaptor 110, a mounting plate 120, a joint 130, a body 140, a reed module 150, a tube 160, and a mouthpiece 170, any of which can be directly or indirectly coupled, secured, assembled, or otherwise connected to each other.

Figure 3:
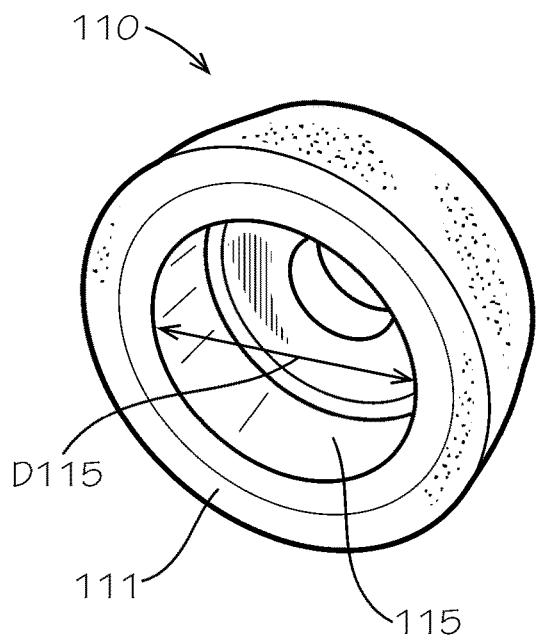
FIG. 3 is a perspective view of a first end of an adaptor of the speech assistance device of FIG. 2.
Figure 4:
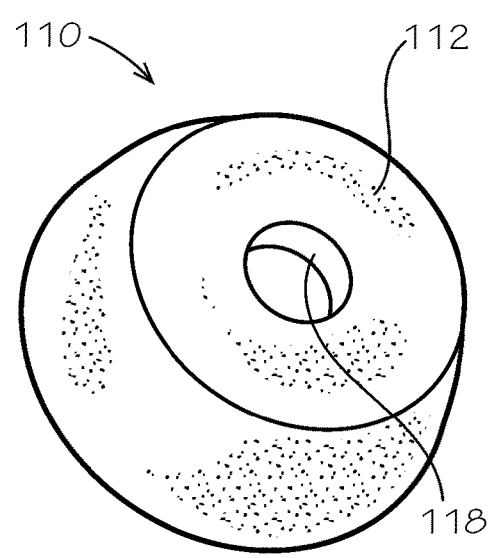
FIG. 4 is a perspective view of a second end of the adaptor of FIG. 3.

As shown in FIGS. 3 and 4, the adaptor 110 can define a first end 111 and a second end 112. In some aspects, the adaptor 110 can define the cavity 115, which can be defined proximate to, for example and without limitation, the first end 111. In other aspects, the adaptor 110 can define a cavity (not shown) proximate to the second end 112. The adaptor 110 can define a bore 118 (shown in FIG. 4), which can be defined proximate to, for example and without limitation, the second end 112. The adaptor 110 can define an axis (not shown), along or about which the bore 118 or any other feature can be aligned. In some aspects, either of an inner surface or a first end surface of the adaptor 110 can define the cavity 115 and can, more specifically, define a cylindrical shape, which can be sized and shaped to receive the HME cassette 80—including by adjusting a depth and inner diameter of the adaptor 110. In other aspects, the inner surface of the adaptor 110 can define other than a cylindrical shape. In some aspects, an outer surface or an inner surface or both an outer surface and an inner surface of the adaptor 110 can define or have the shape of a truncated paraboloid, in whole or in part. In other aspects, such a surface of the adaptor 110 can define or have a frustoconical shape, in whole or in part. In other aspects, such a surface of the adaptor 110 can define or have any other desired shape. In some aspects, as shown, a second end surface of the second end 112 can define or have a flat shape (i.e., can comprise a planar surface). In some aspects, a first adaptor 110 can be replaced with a second adaptor 110 having a shape that more suitably matches the shape of the neck 52 and/or the neck accessory 60 of the user 50.

A portion of the adaptor 110 such as, for example and without limitation, the bore 118 can be sized to allow the passage of air completely through the adaptor 110 from the first end 111 to the second end 112. Any portion of the adaptor 110 can be sized and shaped to receive or be received within any portion of a mating part such as any of the mounting plate 120, the joint 130, the body 140, the reed module 150, the tube 160, and the mouthpiece 170. For example and without limitation, the bore 118 can be sized to receive any portion of a mating part such as any of the mounting plate 120, the joint 130, the body 140, the reed module 150, the tube 160, and the mouthpiece 170. As shown, a first end 121 of the mounting plate 120 can be secured to the adaptor 110.

Figure 5:
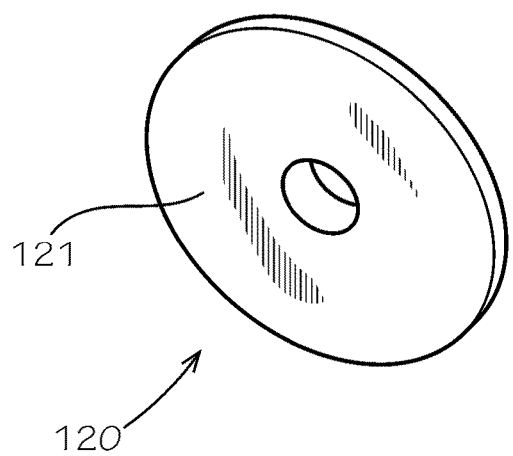
FIG. 5 is a perspective view of a first end of a mounting plate of the speech assistance device of FIG. 2.
Figure 6:
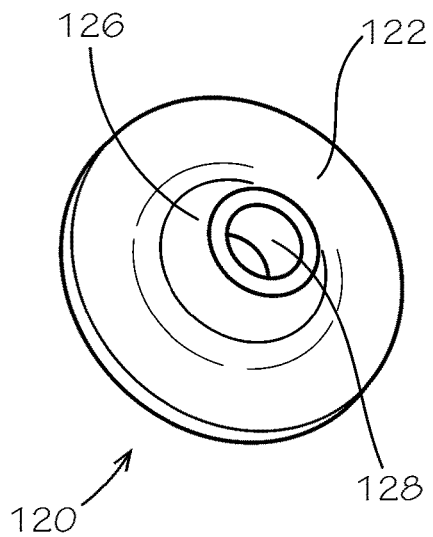
FIG. 6 is a perspective view of a second end of the mounting plate of FIG. 5.

As shown in FIGS. 5 and 6, the mounting plate 120 can comprise the first end 121 and a second end 122. The mounting plate 120 can define a cavity (not shown), which can be defined proximate to, for example and without limitation, the first end 121. The mounting plate 120 can define a bore 128 (shown in FIG. 6), which can be defined proximate to, for example and without limitation, each of the first end 121 and the second end 122. The mounting plate 120 can define an axis (not shown), along or about which the bore 128 or any other feature can be aligned. In some aspects, an inner surface or a first end surface of the mounting plate 120 can define a flat shape (i.e., can comprise a planar surface), which can be sized and shaped to receive or mate with the second end surface of the adaptor 110 as shown in FIG. 2. In other aspects, the inner surface of the mounting plate 120 can define other than a flat shape or planar surface. In some aspects, an outer surface or an inner surface or both an outer surface and an inner surface of the mounting plate 120 can define or have the shape of a truncated paraboloid, in whole or in part. As shown, such a surface of the mounting plate 120 can define a raised boss 126. In other aspects, such a surface of the mounting plate 120 can define or have a frustoconical shape, in whole or in part. In other aspects, such a surface of the mounting plate 120 can define or have any other desired shape.

A portion of the mounting plate 120 such as, for example and without limitation, the bore 128 can be sized to allow the passage of air completely through the mounting plate 120 from the first end 121 to the second end 122. Any portion of the mounting plate 120 can be sized and shaped to receive or be received within any portion of a mating part such as any of the adaptor 110, the joint 130, the body 140, the reed module 150, the tube 160, and the mouthpiece 170. For example and without limitation, the bore 128 can be sized to receive any portion of a mating part such as any of the adaptor 110, the joint 130, the body 140, the reed module 150, the tube 160, and the mouthpiece 170. As shown, a first end 131 of the joint 130 can be secured to the mounting plate 120. More specifically, the first end 131 and the first portion 710 of the joint 130 can be received and secured within the bore 128 of the mounting plate 120.

Figure 7:
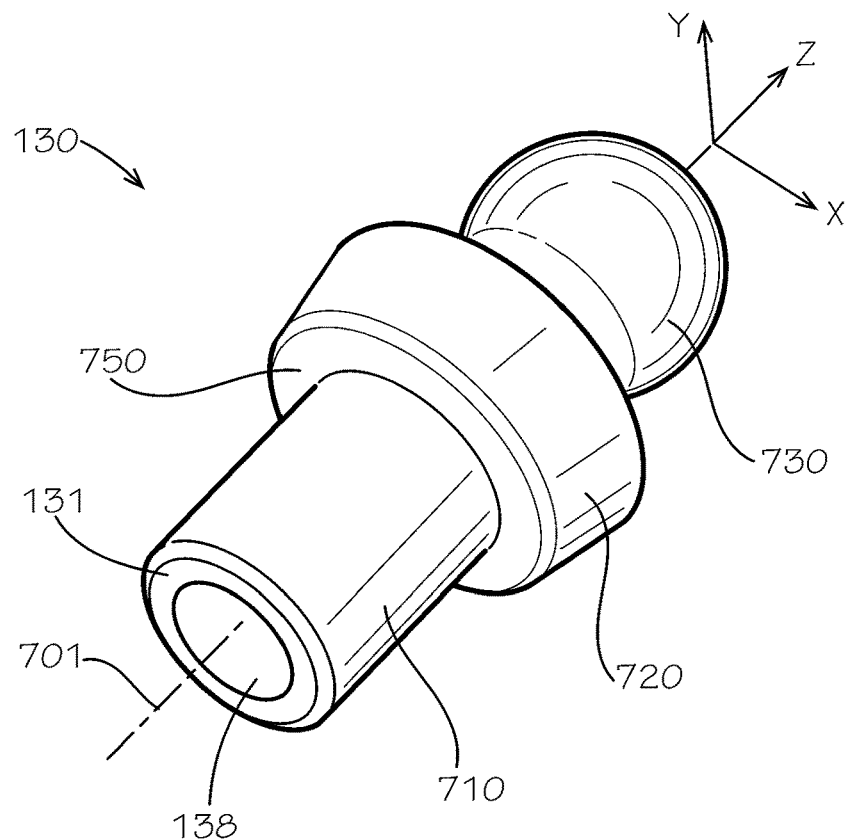
FIG. 7 is a perspective view of a first end of a joint of the speech assistance device of FIG. 2.
Figure 8:
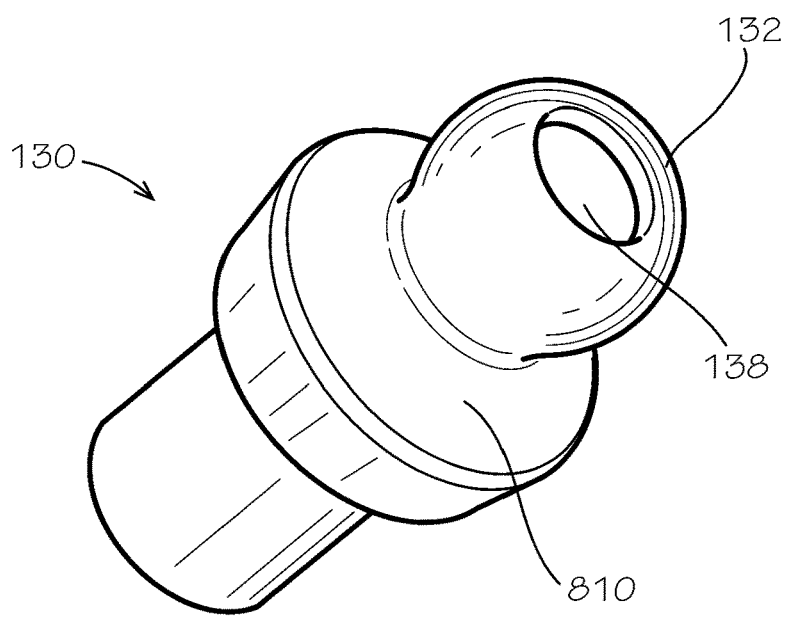
FIG. 8 is a perspective view of a second end of the joint of FIG. 7.

As shown in FIGS. 7 and 8, the joint 130 can comprise the first end 131 and a second end 132. The joint 130 can define a cavity (not shown), which can be defined proximate to, for example and without limitation, the first end 131. The joint 130 can define a bore 138, which can be defined proximate to, for example and without limitation, each of the first end 131 and the second end 132. The joint 130 can define an axis 701, along or about which the bore 138 or any other feature can be aligned. In some aspects, a first end surface of the joint 130 can define a flat shape (i.e., can comprise a planar surface), which can be sized and shaped to receive or mate with a portion of a mating part such as the second end 122 of the mounting plate 120 as shown in FIG. 2. In other aspects, the inner surface of the joint 130 can define other than a flat shape or planar surface.

In some aspects, an outer surface of any of a first portion 710, a second portion 720, and a third portion 730 of the joint 130 can define or have a cylindrical shape, in whole or in part. In other aspects, the outer surface of any of the first portion 710, the second portion 720, and the third portion 730 of the joint 130 can define or have a frustoconical shape, in whole or in part. In other aspects, the outer surface of any of the first portion 710, the second portion 720, and the third portion 730 of the joint 130 can define or have a spherical or ball shape, in whole or in part. In other aspects, the outer surface of any of the first portion 710, the second portion 720, and the third portion 730 of the joint 130 can define or have any other shape as desired, in whole or in part.

In some aspects, the joint 130 can be formed separately from other components of the device 100 described separately herein. In other aspects, features of the joint 130 can be incorporated into another component in order to create a monolithic part incorporating the features of the joint and the other component.

In some aspects, the shape of any of the first portion 710, the second portion 720, and the third portion 730 of the joint 130 can be such that rotation of the joint 130 or a part mated to it about one or more axes such as the axes X, Y, Z is possible (the X-Y-Z coordinate axes shown being representative of coordinate axes present but not shown for any of the components of the device 100). For example and without limitation, with the third portion 730 defining a spherical or ball shape as shown the body 140 can rotate about a center of such shape to allow articulation of the body 140 with respect to the joint 130. Furthermore, any portion of the joint 130 can be sized and shaped to facilitate such movement. For example and without limitation, the second portion 720 can define a conical surface or tapered surface 810, which can allow further rotation of the body 140 with respect to the joint 130. The tapered surface 810 and its proximity to the third portion 730 can be configured to prevent rotation of the body 140 with respect to the joint 130 to the point where passage of air through the bore 138 into any corresponding cavity of a mating part such as the body 140 would be restricted or impeded. As shown, the first portion 710 can have a cylindrical shape, the second portion 720 can define a frustoconical shape, and the third portion 730 can define a spherical shape. The second portion 720 can define a stop surface 750 by which insertion of the joint 130 in an axial direction into a mating component such as the mounting plate 120 can be limited.

Any portion of the joint 130 can be sized and shaped to receive or be received within any portion of a mating part such as any of the adaptor 110, the mounting plate 120, the body 140, the reed module 150, the tube 160, and the mouthpiece 170. In some aspects, any of the first portion 710, the second portion 720, and the third portion 730 of the joint 130 can be sized and shaped to receive or be received within any of the adaptor 110, the joint 130, the body 140, the reed module 150, the tube 160, and the mouthpiece 170. In other aspects, the bore 138 can be sized to receive any portion of a mating part such as any of the adaptor 110, the mounting plate 120, the body 140, the reed module 150, the tube 160, and the mouthpiece 170. A portion of the joint 130 such as, for example and without limitation, the bore 138 itself can be sized to allow the passage of air completely through the joint 130 from the first end 131 to the second end 132. As shown, the first end 141 and the first portion 710 of the body 140 can be secured to the second end 132 of the joint 130.

Figure 9:
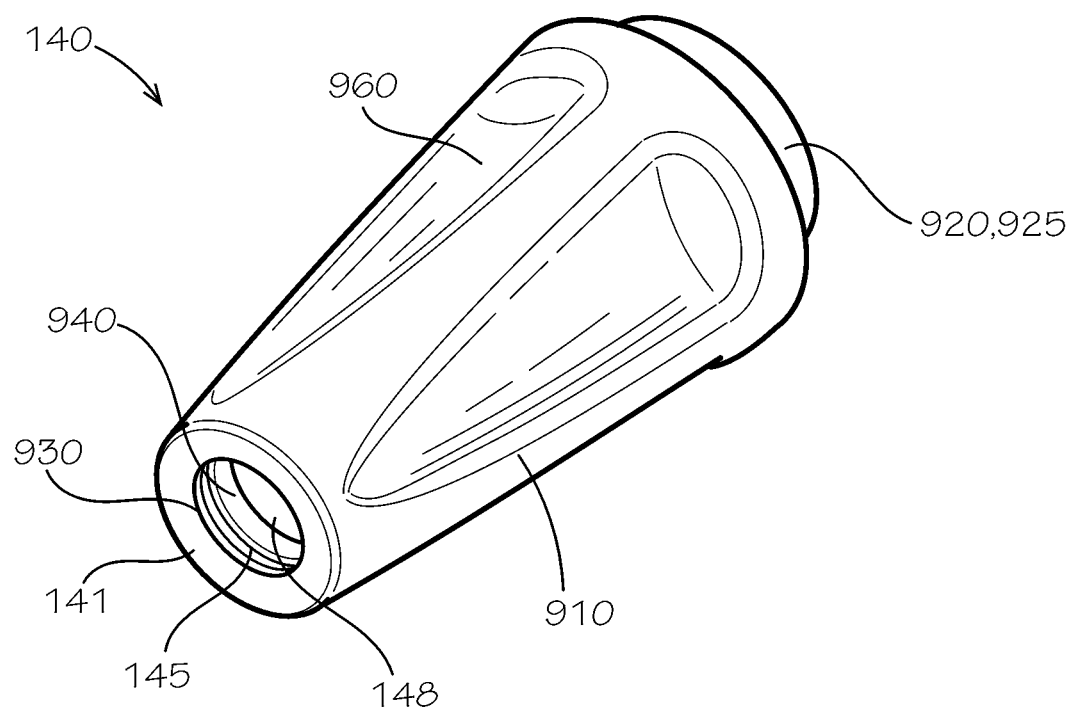
FIG. 9 is a perspective view of a first end of a body of the speech assistance device of FIG. 2.
Figure 10:
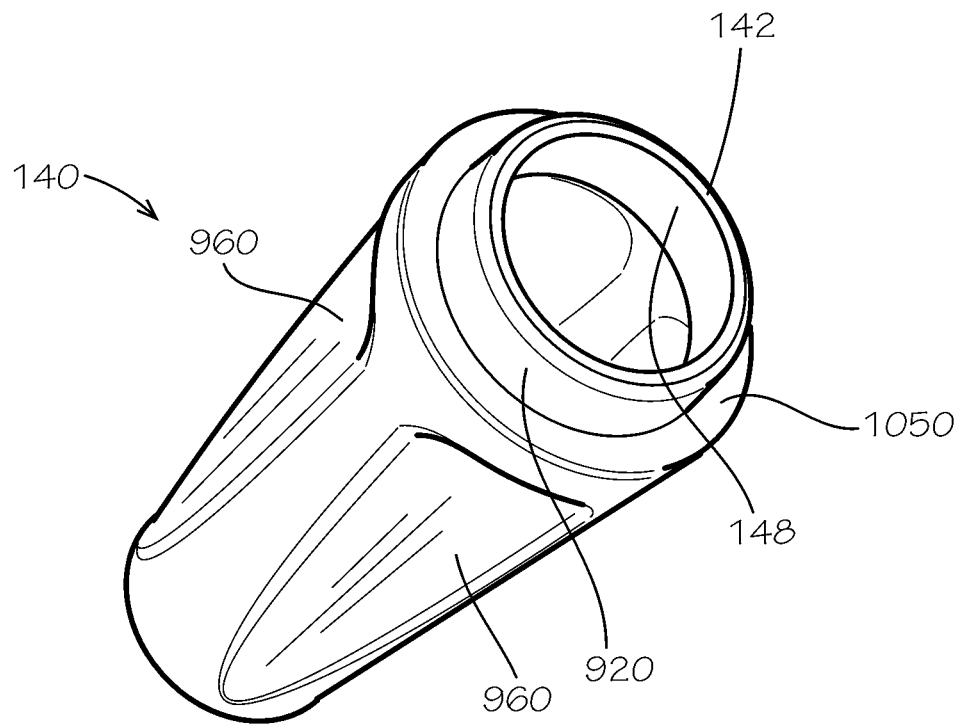
FIG. 10 is a perspective view of a second end of the body of FIG. 9.

As shown in FIGS. 9 and 10, the body 140 can comprise the first end 141 and a second end 142. The body 140 can define a cavity 145, which can be defined proximate to, for example and without limitation, the first end 141. In some aspects, the cavity 145 can define a spherical shape. In other aspects, the body 140 at the cavity 145 can comprise a first ridge 930 and a second ridge 940, which individually or together can lock in an axial position a portion of a mating part such as the third portion 730 of the joint 130. In some aspects, the cavity 145 can vary in diameter, can extend towards the second end 142, and can accommodate more than the joint 130. The body 140 can define a bore 148, which can be defined proximate to, for example and without limitation, each of the first end 141 and the second end 142. The body 140 can define an axis (not shown), along or about which the bore 148 or any other feature can be aligned. In some aspects, a first end surface of the body 140 can define a rounded surface, which can be sized and shaped to facilitate receipt of or mating with a portion of a mating part such as the second end 132 of the joint 130. In other aspects, the first end surface of the body 140 can define any other shape including a flat shape (i.e., can comprise a planar surface).

In some aspects, an outer surface of any of a first portion 910 and a second portion 920 of the body 140 can define or have a cylindrical shape, in whole or in part. In other aspects, the outer surface of any of the first portion 910 and the second portion 920 of the body 140 can define or have a frustoconical shape, in whole or in part. In other aspects, the outer surface of any of the first portion 910 and the second portion 920 of the body 140 can define or have any other shape as desired, in whole or in part.

In some aspects, the shape of any of the first portion 910 and the second portion 920 of the body 140 can be such that rotation of the body 140 or a part mated to it about one or more axes is possible. For example and without limitation, the body 140 can rotate about a center of the cavity 145 to allow articulation of the body 140 with respect to the joint 130. Furthermore, any portion of the body 140 can be sized and shaped to facilitate such movement. For example and without limitation, the first portion 910 can define a conical surface or tapered surface, which can allow further rotation of the body 140 with respect to the joint 130. The tapered surface and its proximity to the first end 141 can be configured to prevent rotation of the joint 130 with respect to the body 140 to the point where passage of air through the bore 148 into any corresponding cavity of a mating part such as the joint 130 would be restricted or impeded. As shown, the first portion 910 can have a frustoconical shape and the second portion 920 can define a cylindrical shape. Either of the first portion 910 or the second portion 920 can define a stop surface 1050 (shown in FIG. 10) by which insertion of the body 140 in an axial direction into a mating component such as the reed module 150 can be controlled, limited, or maintained.

Either of the first portion 910 and the second portion 920 can define indentations 960. In some aspects, the indentations 960 can facilitate general holding or gripping of the device 100 by the user 50 or holding or gripping of the body 140 to facilitate assembly or disassembly of a mating portion such as the reed module 150. In other aspects, the indentations 960 can increase the strength—or, more specifically, the rigidity—of the body 140 by increasing its resistance to deformation when gripped or otherwise manipulated. In other aspects, the indentations 960 can facilitate thinning of a material thickness of the body 140 beyond a point that would otherwise be desirable when the body 140 does not define the indentations 960.

Figure 14A:
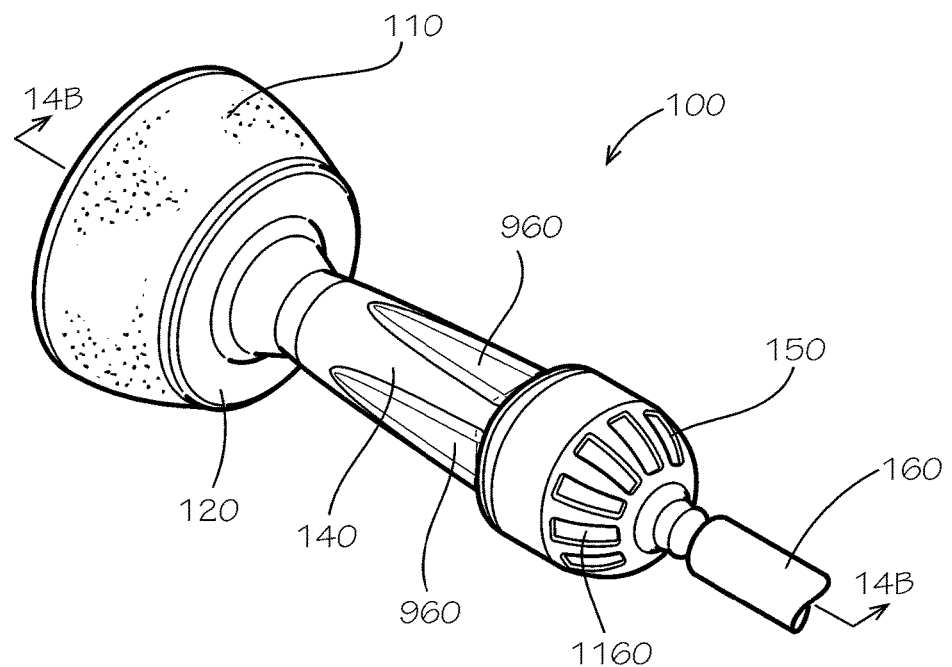
FIG. 14A is a top perspective view of the speech assistance device of FIG. 2 showing the reed module in accordance with another aspect of the current disclosure.
Figure 14B:
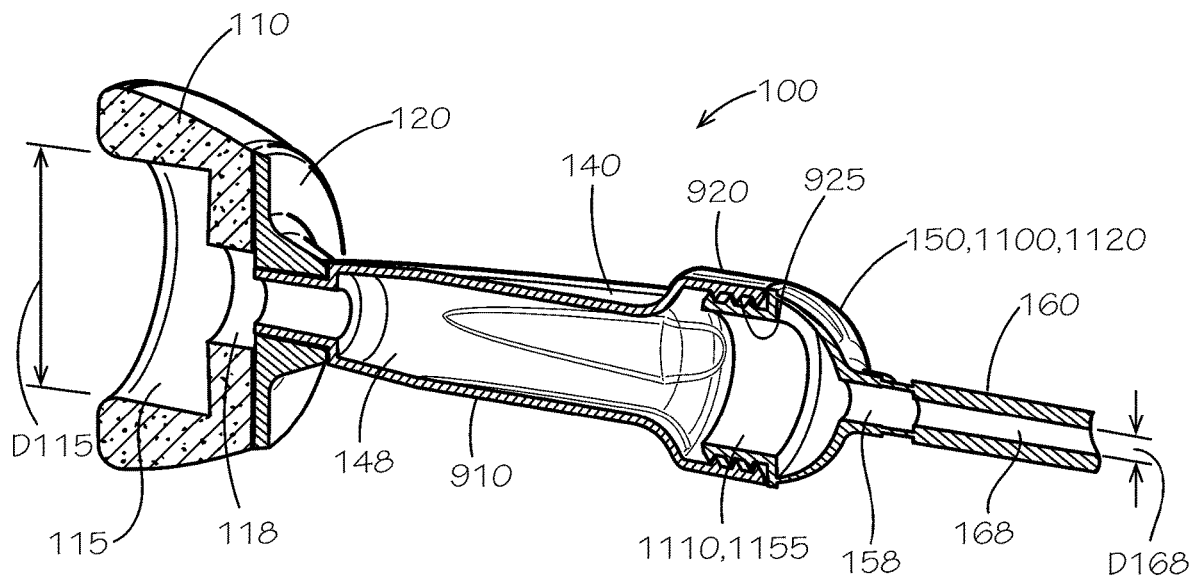
FIG. 14B is a section view of the speech assistance device of FIG. 2 taken from line 14B-14B of FIG. 14A but with the reeds themselves and some structure directly surrounding the reeds removed.

Either of the first portion 910 and the second portion 920 can define a fastening element 925. In some aspects, the fastening element 925 can comprise threads (not shown), which can comprise male threads (i.e., facing outward relative to a central axis of the body 140), to facilitate assembly and disassembly of a mating component. In other aspects, the fastening element 925 can comprise a boss protruding from or an indentation defined in a surface of the second portion 920. The boss or indentation can facilitate a press-fit assembly or disassembly of a mating portion such as the reed module 150. In other aspects, as shown in FIG. 14B, the fastening element 925 can comprise female threads (i.e., facing inward relative to a central axis of the body 140). In any case, the threads of the fastening element 925 can be of any size or class, including both fine and coarse classifications of any diameter and pitch. In other aspects, including to facilitate assembly and disassembly of mating parts, any of the adaptor 110, the mounting plate 120, the joint 130, the reed module 150, the tube 160, and the mouthpiece 170 can define a fastening element comprising any of the features of the fastening element 925.

Any portion of the body 140 can be sized and shaped to receive or be received within any portion of a mating part such as any of the adaptor 110, the mounting plate 120, the joint 130, the reed module 150, the tube 160, and the mouthpiece 170. In some aspects, any of the first portion 910 and the second portion 920 of the body 140 can be sized and shaped to receive or be received within any of the adaptor 110, the mounting plate 120, the joint 130, the reed module 150, the tube 160, and the mouthpiece 170. In other aspects, the bore 148 can be sized to receive any portion of a mating part such as any of the adaptor 110, the mounting plate 120, the joint 130, the reed module 150, the tube 160, and the mouthpiece 170. A portion of the body 140 such as, for example and without limitation, the bore 148 itself can be sized to allow the passage of air completely through the body 140 from the first end 141 to the second end 142. As shown, the reed module 150 can be secured to the second end 142 of the body 140.

Figure 11:
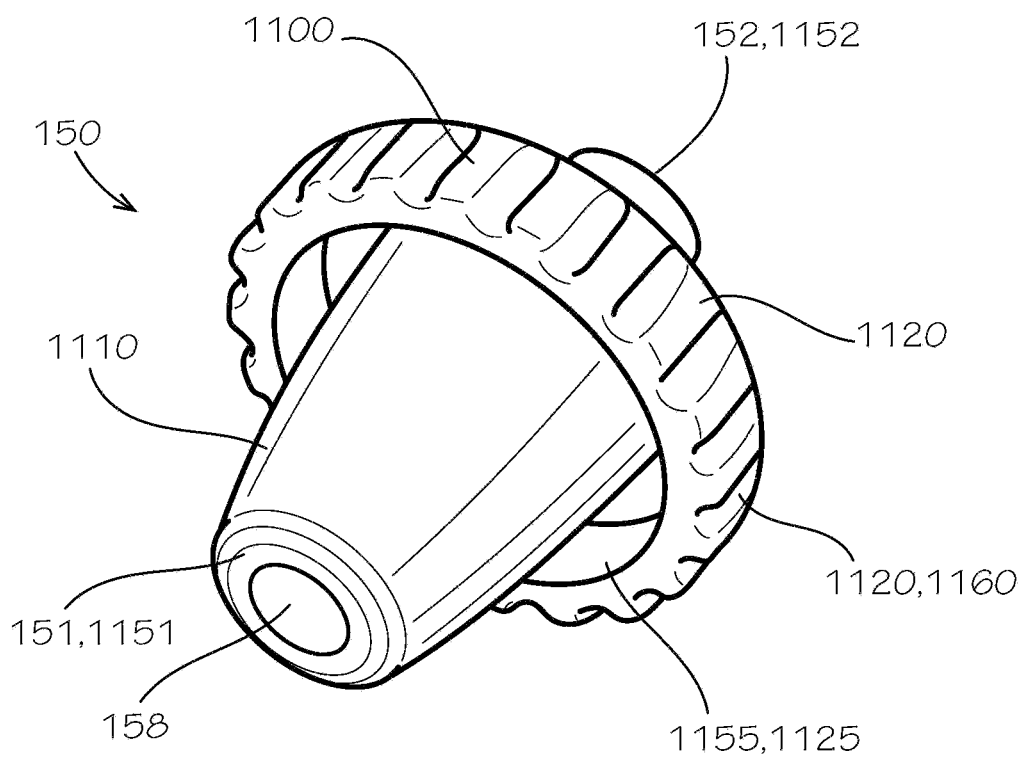
FIG. 11 is a perspective view of a first end of a reed module of the speech assistance device of FIG. 2.
Figure 12:
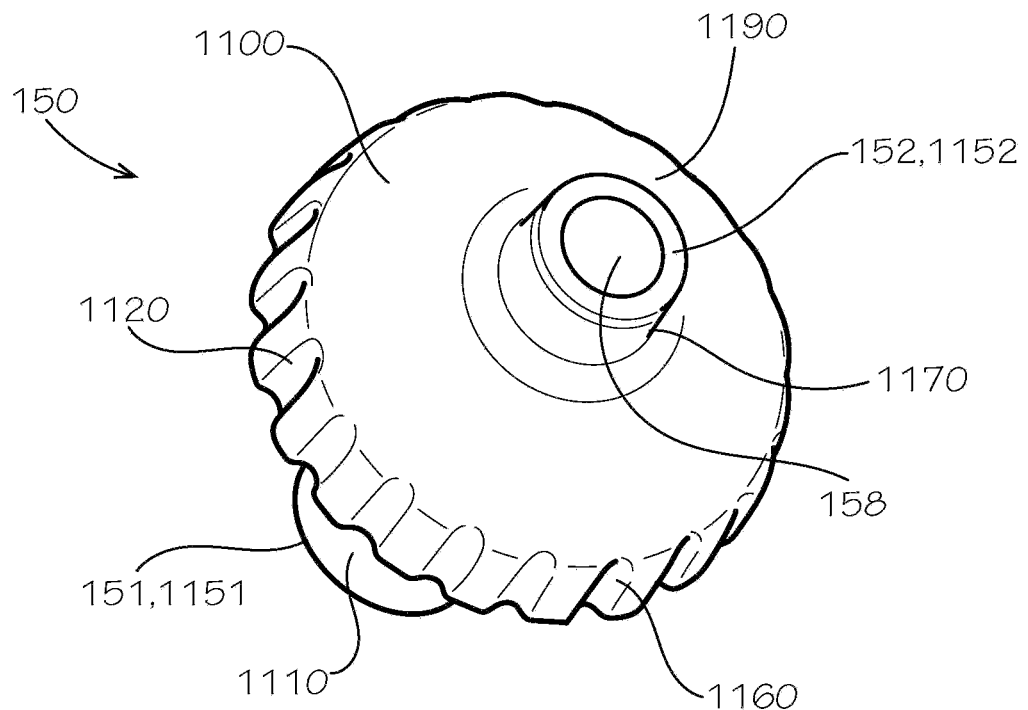
FIG. 12 is a perspective view of a second end of the reed module of FIG. 11.

As shown in FIGS. 11 and 12, the reed module 150 can comprise a reed holder 1100, which can comprise a first end 1151 and a second end 1152. The reed holder 1100 can define a cavity 1155, which can be defined proximate to, for example and without limitation, the first end 1151. In some aspects, the cavity 1155 can define a cylindrical shape. In other aspects, the reed holder 1100 at the cavity 145 can comprise a non-cylindrical shape. The reed holder 1100 can define a bore 158, which can be defined proximate to, for example and without limitation, each of the first end 1151 and the second end 1152. The reed holder 1100 can define an axis (not shown), along or about which the bore 158 or any other feature can be aligned. In some aspects, a first end surface of the reed holder 1100 can have a flat shape (i.e., can comprise a planar surface), which can be sized and shaped to facilitate receipt of or mating with a portion of a mating part such as the second end 142 of the body 140. In other aspects, the first end surface of the reed holder 1100 can define any other shape.

In some aspects, an outer surface or an inner surface or both an outer surface and an inner surface of any of a first portion 1110 and a second portion 1120 of the reed holder 1100 can define or have a cylindrical shape, in whole or in part. In other aspects, such a surface of any of the first portion 1110 and the second portion 1120 of the reed holder 1100 can define or have a frustoconical shape, in whole or in part. In other aspects, such a surface of any of the first portion 1110 and the second portion 1120 of the reed holder 1100 can define or have any other shape as desired such as, for example and without limitation, a conical, tapered, parabolic, spherical or ball surface, with or without truncation, in whole or in part. As shown, the first portion 1110 can have the shape of a truncated paraboloid, and the second portion 1120 can have frustoconical and paraboloid elements. Either of the first portion 1110 or the second portion 1120 can define a stop surface 1190 by which insertion of the reed holder 1150 in an axial direction into a mating component such as the tube 160 can be controlled, limited, or maintained.

In some aspects, the shape of any of the first portion 1110 and the second portion 1120 of the reed holder 1100 can be such that rotation of the reed holder 1100, in whole or in part, or a part mated to it about one or more axes is possible. For example and without limitation, the tube 160 or a separate portion of the reed module 150 can rotate about a center of a cavity (now shown) defined in the second end 1152 to allow articulation of a mating component such as, for example and without limitation, the tube 160 with respect to the reed holder 1100. Furthermore, any portion of the reed holder 1100 can be sized and shaped to facilitate such movement such as the cavity 145 is sized to facilitate movement of the body 140 with respect to the joint 130.

Either of the first portion 1110 and the second portion 1120 can define indentations 1160. In some aspects, the indentations 1160 can facilitate general holding or gripping of the device 100 by the user 50 or holding or gripping of the reed module 150 to facilitate assembly or disassembly of a mating portion such as the body 140 or the tube 160. In other aspects, the indentations 1160 can increase the strength—or, more specifically, the rigidity—of the reed holder 1100 by increasing its resistance to deformation when gripped or otherwise manipulated. In other aspects, the indentations 1160 can facilitate thinning of a material thickness of the reed holder 1100 beyond a point that would otherwise be desirable when the reed holder 1100 does not define the indentations 1160.

Figure 14C:
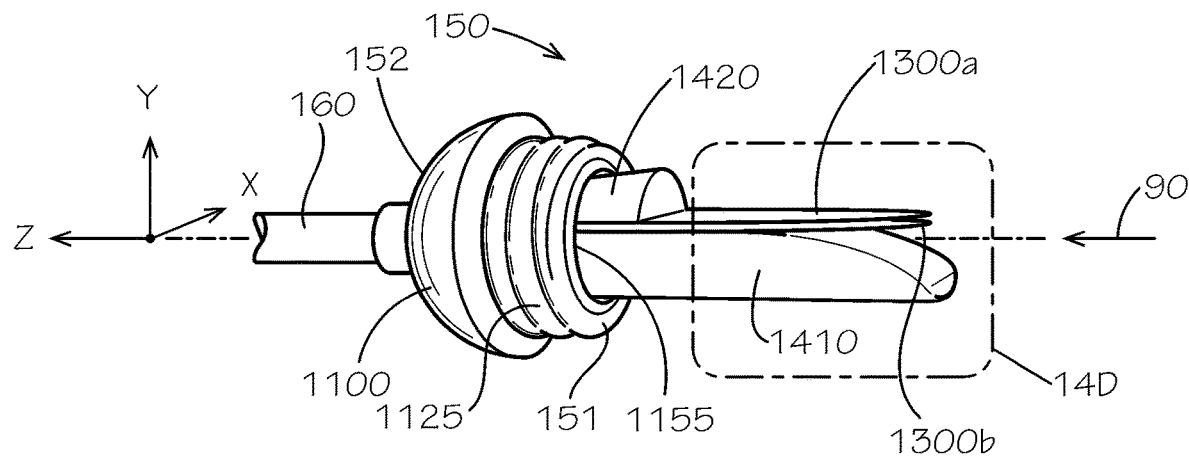
FIG. 14C is a bottom perspective view showing the reed module of FIG. 14A.

Either of the first portion 1110 and the second portion 1120 can define a fastening element 1125. In some aspects, the fastening element 1125 can comprise threads, which can comprise female threads, to facilitate assembly and disassembly of a mating component. In other aspects, the fastening element 1125 can comprise a boss protruding from or an indentation defined in a surface of the second portion 1120 such as an inner surface of the cavity 1155. The boss or indentation can facilitate a press-fit assembly or disassembly of a mating portion such as the body 140. In other aspects, as shown in FIGS. 14B and 14C, the fastening element 1125 can comprise male threads. In any case, the threads of the fastening element 1125 can be of any size or class, including both fine and coarse classifications of any diameter and pitch.

Any portion of the reed holder 1100 can be sized and shaped to receive or be received within any portion of a mating part such as any of the adaptor 110, the mounting plate 120, the joint 130, the body 140, the tube 160, and the mouthpiece 170. In some aspects, any of the first portion 1110 and the second portion 1120 of the reed holder 1100 can be sized and shaped to receive or be received within any of the adaptor 110, the mounting plate 120, the joint 130, the body 140, the tube 160, and the mouthpiece 170. In other aspects, the bore 158 can be sized to receive any portion of a mating part such as any of the adaptor 110, the mounting plate 120, the joint 130, the body 140, the tube 160, and the mouthpiece 170. A portion of the reed holder 1100 such as, for example and without limitation, the bore 158 itself can be sized to allow the passage of air completely through the reed holder 1100 from the first end 1151 to the second end 1152. As shown, a first end 161 of the tube 160 can be secured to a protrusion 1170 of the second end 1152.

Figure 13A:
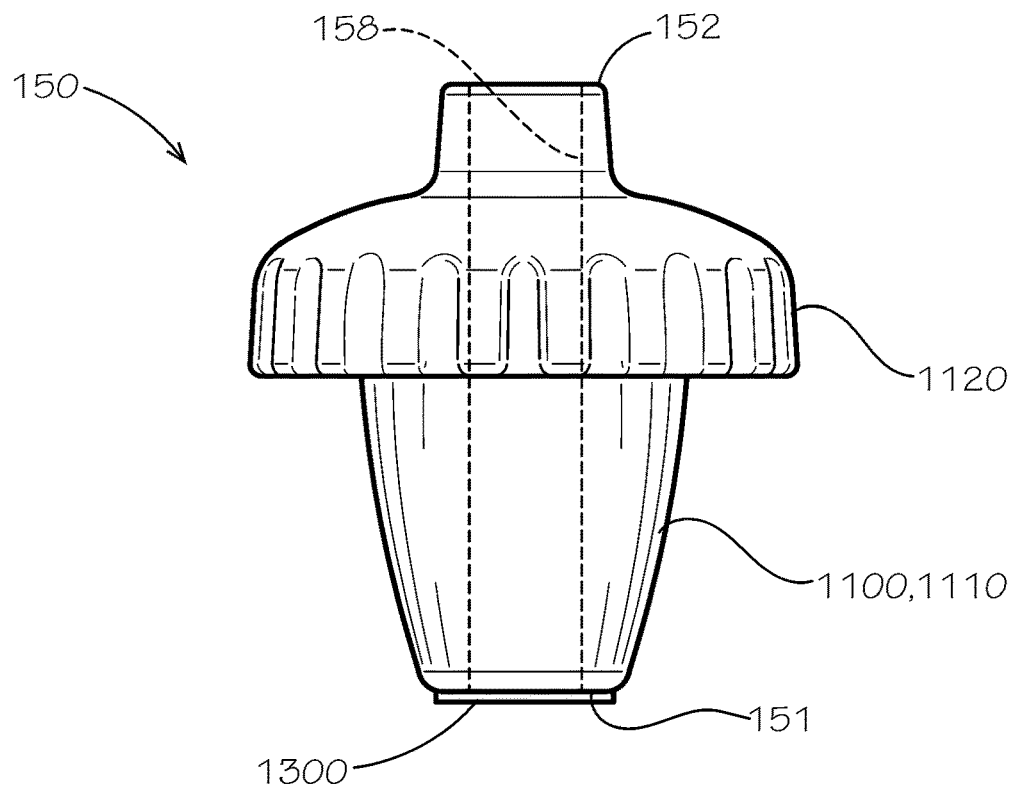
FIG. 13A is a side view of the reed module of FIG. 11 comprising a reed in accordance with one aspect of the current disclosure.
Figure 13B:
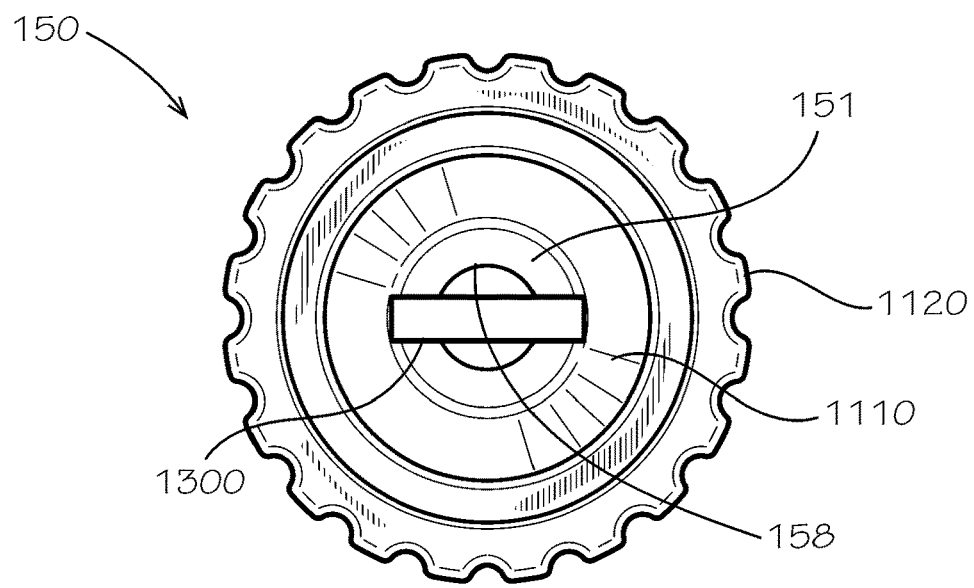
FIG. 13B is a bottom view of the reed module of FIG. 13A.

As shown in FIGS. 13A and 13B, the reed module 150 can comprise a reed 1300. In some aspects, as shown, the reed 1300 can be secured to the reed holder 1100 proximate to a first end 151 of the reed module 150 and the first end 1151 of the reed holder 1100. In other aspects, the reed 1300 can be secured to the reed holder 1100 proximate to a second end 152 of the reed module 150 and the second end 1152 of the reed holder 1100. In other aspects, the reed 1300 can be secured to the reed holder 1100 at a position between the first ends 151, 1151 and the respective second ends 152, 1152. In some aspects, as shown in FIG. 13B, the reed 1300 can be stretched or suspended across the bore 158. The reed 1300 can be secured in place against the reed holder 1100 with a fastener such as, for example and without limitation, an elastic band securing ends of the reed 1300 in place against the reed holder 1100 or, as shown, a flexible adhesive material positioned between the reed 1300 and the reed holder 1100 affixing the reed 1300 against the reed holder 1100. The flexible adhesive material can be an elastic adhesive able to hold the reed 1300 in place on the reed holder 1100 without interfering with or limiting the ability of the reed 1300 to naturally vibrate. In other aspects, the reed 1300 can be secured to the reed holder 1100 using securing posts on opposing sides of the reed holder 1100. In other aspects, the reed 1300 can be secured to the reed 1330 by affixing the reed 1300 with a band sitting in a groove or adjacent to a flange on a surface of the reed holder 1100. In other aspects, the reed 1300 can be molded into the reed holder 1100. In some aspects, as shown, the reed 1300 can have a rectangular shape. In other aspects, the reed 1300 can have a non-rectangular shape. In some aspects, the reed 1300 can be stretched tight across the reed holder 1100 and even held in tension during use. In other aspects, the reed 1300 can be allowed to remain loose. In some aspects, a portion of the reed 1300 can protrude axially beyond the first end surface of the reed holder 1100. In other aspects, as shown, the entire reed 1300 can protrude axially beyond the first end surface of the reed holder 1100. In some aspects, a width of the reed 1300 can measure approximately 3 millimeters (approximately ⅛"). In other aspects, the width can measure more or less than this dimension.

Figure 13C:
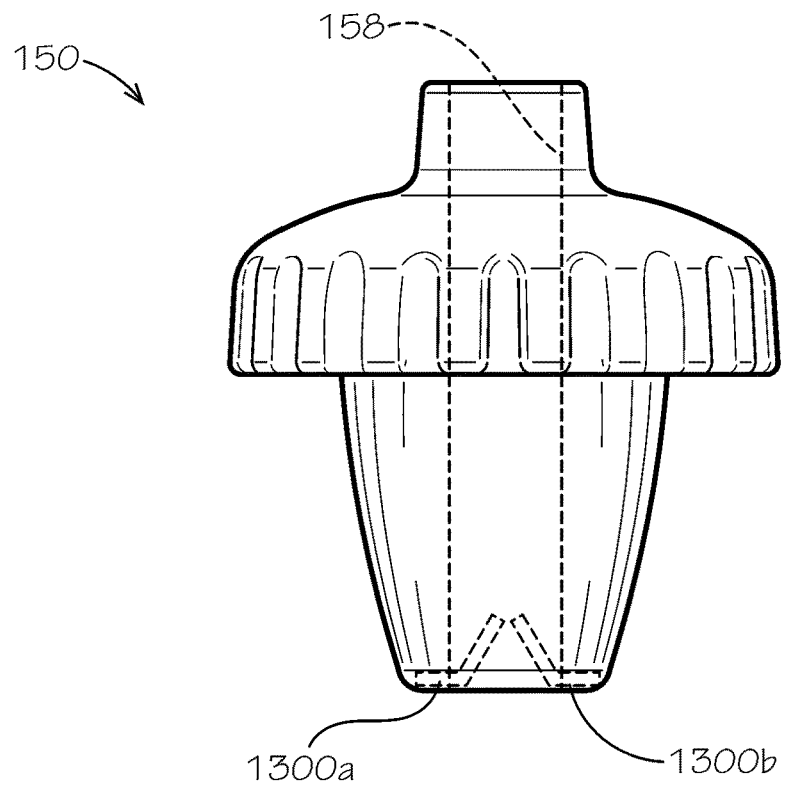
FIG. 13C is a side view of the reed module of FIG. 11 comprising a reed in accordance with another aspect of the current disclosure.
Figure 13D:
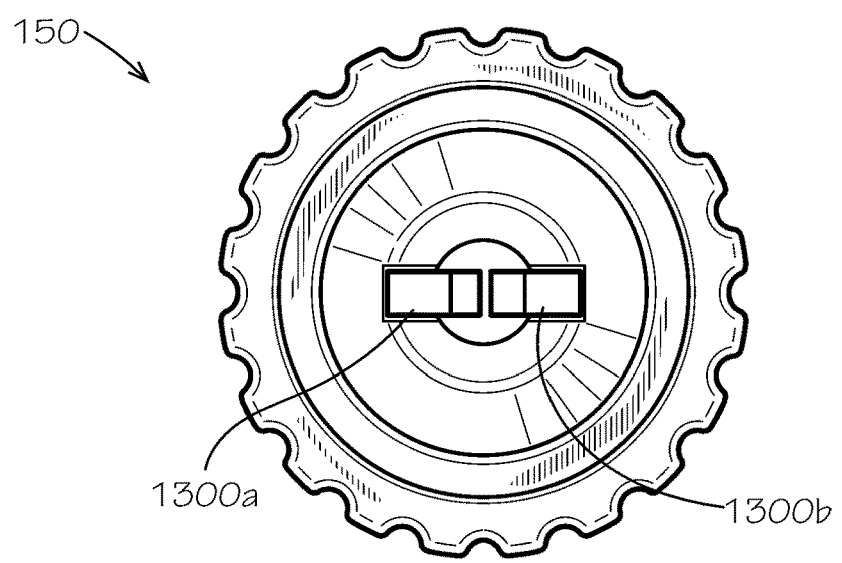
FIG. 13D is a bottom view of the reed module of FIG. 13C.

As shown in FIGS. 13C and 13D, which can resemble the construction of a reed or reeds in a musical instrument comprising them, the reed module 150 can comprise a pair of reeds 1300a,b. In some aspects, as shown, each of a first reed 1300a and a second reed 1300b of the pair of reeds can extend into the bore 158. In some aspects, the reeds 1300a,b can define a gap therebetween. In some aspects, at least a portion of the reeds 1300a,b can sit below the first end surface of the reed holder 1100. As shown, an axially outermost surface of the reeds 1300a,b can sit flush with the first end surface of the reed holder 1100. In other aspects, the reeds 1300a,b can abut each other such that no gap exists between them except during their movement. In some aspects, such as with the reed 1300 shown in FIGS. 13A and 13B, sound can be produced by air traveling around the reed 1300. In other aspects, such as with the reed 1300 shown in FIGS. 13C and 13D, sound can be produced by air traveling through the reeds 1300a,b.

As shown in FIGS. 14A-14E and similarly as shown in FIGS. 13C and 13D, the reed module 150 can comprise at least two of the reeds 1300a,b housed inside, for example and without limitation, the reed module 150 and optionally also inside the body 140, which can be elongated in comparison to the body 140 shown previously. The fastening element 1125 (shown in FIG. 14C) of the reed holder 1100 can be received within and secured to the fastening element 925 of the body 140. In some aspects, the reed module 150 can comprise only the single reed 1300. In other aspects, the reed module 150 can comprise the pair of reeds 1300a,b. In other aspects, the reed module 150 can comprise any number of the reeds 1300, including three or more reeds 1300.

Figure 14D:
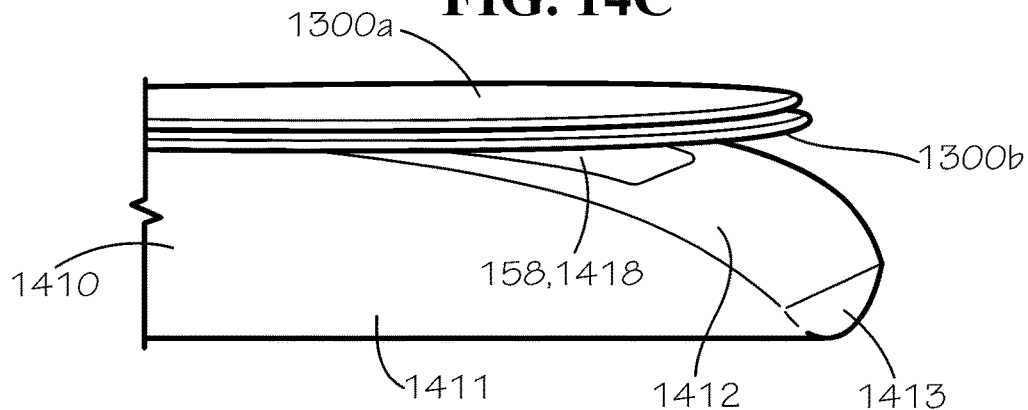
FIG. 14D is a detail perspective view showing the reed module of FIG. 14A taken from detail 14D of FIG. 14C.
Figure 14E:
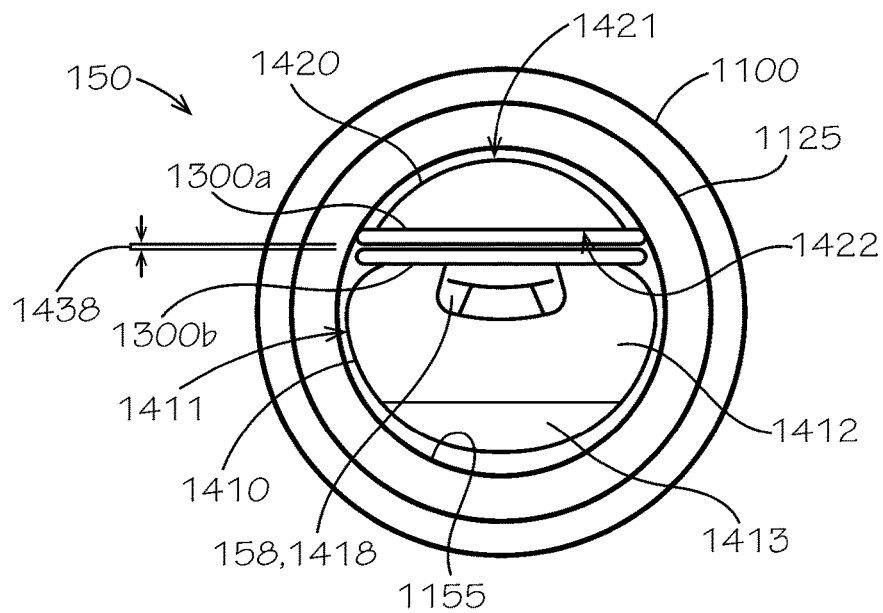
FIG. 14E is a bottom end view of the reed module of FIG. 14A.

More specifically, as shown in FIGS. 14C-14E, the reeds 1300a,b ora single reed 1300 can be held within the cavity 1155 of the reed holder 1100 and, once the reed module 150 is assembled to the device 100, also within the cavity 145 of the body 140. For example and without limitation, the reeds 1300a,b can sandwiched together inside the reed holder 1100, with or without a gap 1438 therebetween based on the desired sound to be produced. More specifically, the reeds 1300a,b or a single reed 1300 can be sandwiched between a first support 1410, which can be a sound board, and a second support 1420, which can be a wedge.

Respective outer surfaces 1411,1421 (shown in FIG. 14E) of the supports 1410,1420 can contact a surface of the cavity 1155 of the reed holder 1100 to fix the position of both the supports 1410,1420 and the reeds 1300a,b. Each of the first support 1410 and the second support 1420 can define a length sufficient to secure the reeds 1300a,b or the single reed 1300 inside the cavity 1155. As shown in FIGS. 14D and 14E, a supporting surface such as respective contacting portions of an inner surface 1412 of the first support 1410 and an inner surface 1422 of the second support 1420 can contact the respective reeds 1300b,a for an axial distance measured from a base of the reeds 1300a,b (the base behind hidden inside the cavity 1155) but can stop short of a tip of the reeds 1300a,b (or, as applicable, the reed 1300) to allow vibration of at least the tip of the reeds 1300a,b during operation. As shown, the first support 1410 can extend to or even beyond the top of the reeds 1300a,b. Furthermore, the tip of the reeds 1300a,b can extend or point towards the incoming air 90. As flow of the air 90 past or through, as the case may be, the reeds 1300a,b, the reeds 1300a,b can vibrate to produce a sound inside the device 100 and traveling with the air 90 through the bore 158 and also specifically through a bore 1418 (shown in FIG. 14D) defined in the first support 1410. As shown, a portion of the inner surface 1412 of the first support 1410 can be curved (i.e., can define a radius) which can allow vibration of and at least partial contact with the reed or reeds 1300. This vibration can comprise rapid alternating movements of the reed or reeds 1300 toward the first support 1410 and then away from the first support 1410. Either of the first support 1410, as shown, or the second support 1420 can be truncated at one end such that, for example and without limitation, an end surface 1413 is defined in the first support 1410. Either of the supports 1410,1420 can define a semicircular cross-section or, as shown in FIG. 14E, can define in cross-section a circular cross-section that is larger than or smaller than a semicircular cross-section. In other aspects, either of the supports 1410,1420 can define a non-circular shape such as, for example and without limitation, the shape of a polygon. A position, a cross-sectional shape, an axial length, and other characteristics of the bore 1418 can be adjusted together with characteristics of the reeds 1300a,b or the reed 1300 to adjust the sound produced by the device 100. As shown, the structure of the supports 1410,1420 and the reeds 1300a,b can, for example and without limitation, be adapted from that used in a bird call—such as a duck call—used by bird hunters.

In addition to other considerations disclosed herein, characteristics of the sound produced by the device 100 including a tone of the sound can be affected by multiple factors including the velocity and the volume of air 90 (shown in FIG. 24) able to be pushed through the stoma 58 (shown in FIG. 24) by the user 50. In some aspects, the velocity and the volume of air 90 can be adjusted before or after the reed module 150 by increasing or decreasing an inner diameter of bores of the device such as one or more of the bores 118,128,138,148,158,168,178—such as, for example and without limitation, an inner diameter D168 of the bore 168 of the tube 160. The tone of the sound produced by the device 100 can also vary depending on dynamics of the resonating cavities (including, e.g., a throat cavity, a nasal cavity, and the oral cavity 51) of the user 50. While the variety of sounds that can be produced can be innumerable based on small changes in the size, position, and orientation of various components, basic qualities of the sound can be altered by not only adjusting the velocity and volume of the air 90 expelled by the user 50 through the stoma 58 but by changing, for example and without limitation, the size (including length, width, and thickness), position, shape, orientation, and material of each of the reeds 1300a,b individually and with respect to each other or by changing the material (such as making it harder to facilitate sound transmission or softer to muffle or limit sound transmission) of one or more of the components 110,120,130,140,150,160, 170 of the device 100. Such adjustment can alter the basic qualities of the sound for at least the reason that the various bores and cavities of the components of the device 100 can themselves function as resonating cavities in addition to functioning as producers and/or transmitters of air and/or sound.

Figure 15:
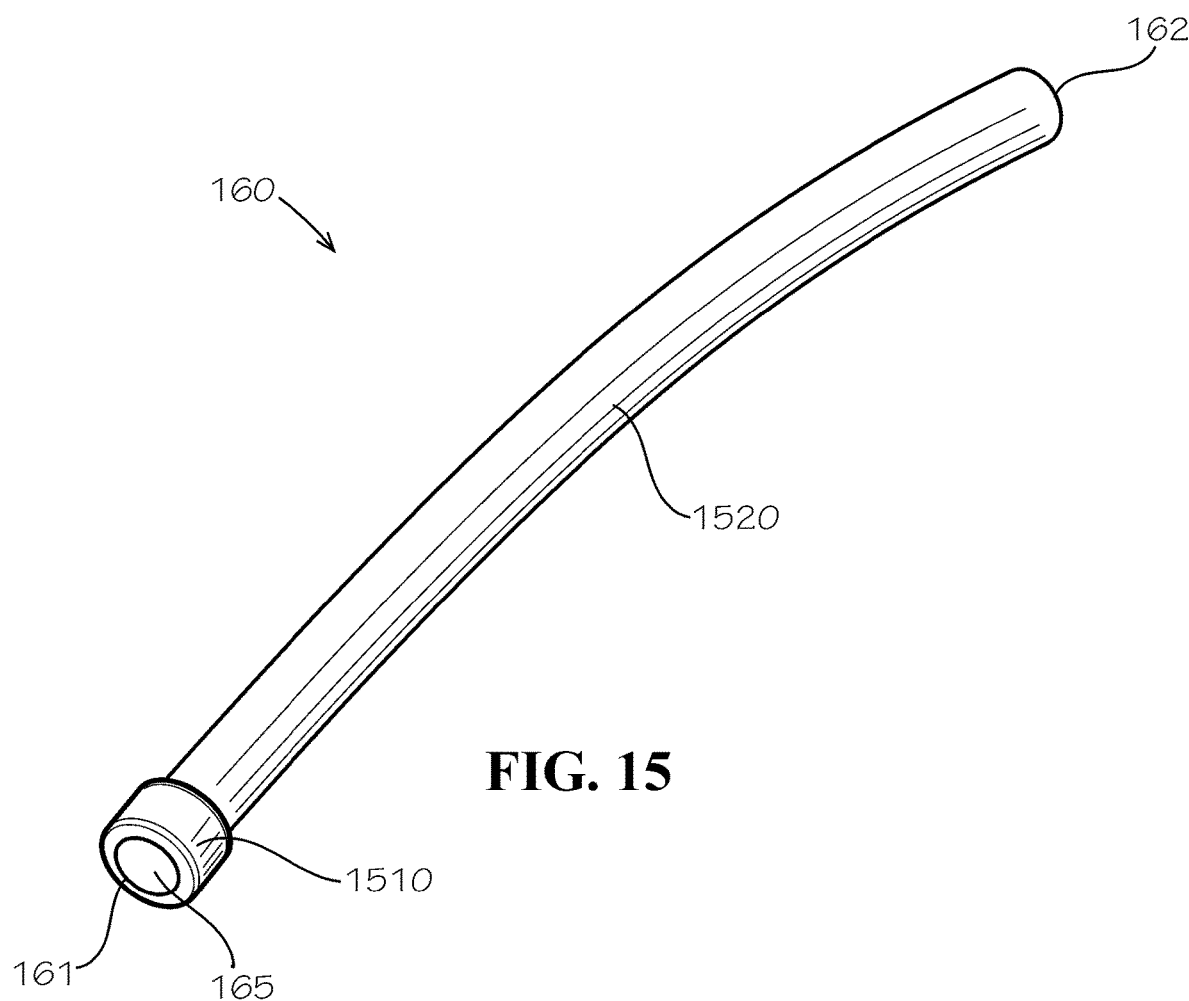
FIG. 15 is a perspective view of a first end of a tube of the speech assistance device of FIG. 2.
Figure 16:
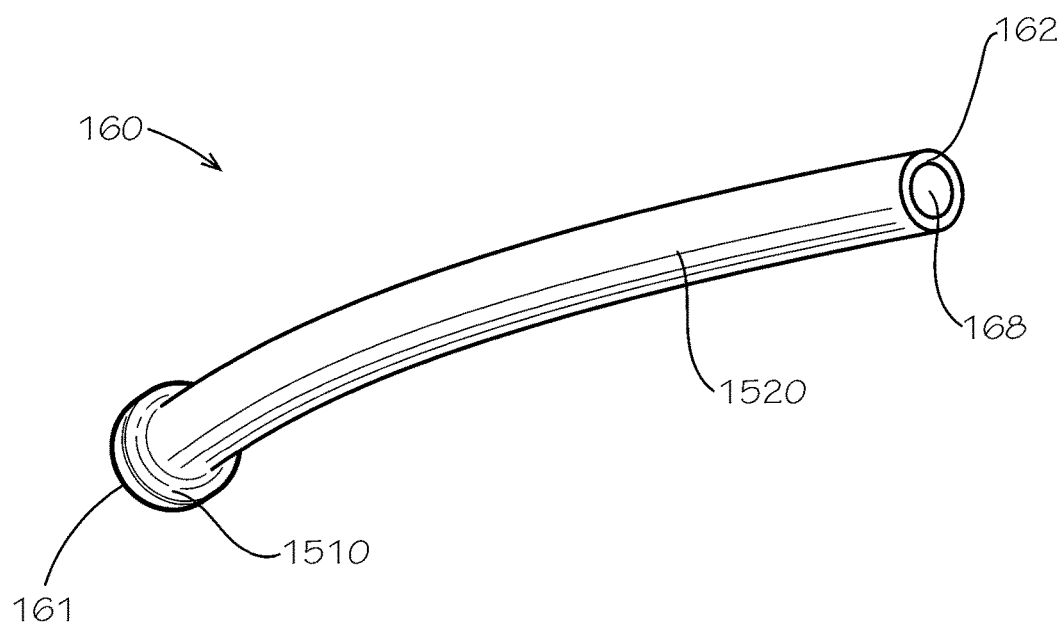
FIG. 16 is a perspective view of a second end of the tube of FIG. 15.

As shown in FIGS. 15 and 16, the tube 160 can comprise a first end 161 and a second end 162. The tube 160 can define a cavity 165, which can be defined proximate to, for example and without limitation, the first end 161. In some aspects, the cavity 165 can define a cylindrical shape. In other aspects, the tube 160 at the cavity 165 can comprise a non-cylindrical shape. The tube 160 can define a bore 168 (shown in FIG. 16), which can be defined proximate to, for example and without limitation, each of the first end 161 and the second end 162. The tube 160 can define an axis (not shown), along or about which the bore 168 or any other feature can be aligned. In some aspects, a first end surface of the tube 160 can have a flat shape (i.e., can comprise a planar surface), which can be sized and shaped to facilitate receipt of or mating with a portion of a mating part such as the second end 152 of the reed module 150. In other aspects, the first end surface of the tube 160 can define any other shape. The tube 160 can be hollow.

In some aspects, an outer surface or an inner surface or both an outer surface and an inner surface of any of a first portion 1510 and a second portion 1520 of the tube 160 can define or have a cylindrical shape, in whole or in part. In other aspects, such a surface of any of the first portion 1510 and the second portion 1520 of the tube 160 can define or have a frustoconical shape, in whole or in part. In other aspects, such a surface of any of the first portion 1510 and the second portion 1520 of the tube 160 can define or have any other shape as desired such as a conical, tapered, parabolic, spherical or ball surface, with or without truncation, in whole or in part. The shape of any of the first portion 1510 and the second portion 1520 of the tube 160 can be such that rotation of the tube 160, in whole or in part, or a part mated to it about one or more axes is possible.

Either of the first portion 1510 or the second portion 1520 can define a stop surface (not shown but, for example, present at an axially innermost surface of the cavity 165) by which insertion of the tube 160 in an axial direction into a mating component such as the reed module 150 can be controlled, limited, or maintained. Any surface of either of the first portion 1510 and the second portion 1520 can further define indentations (not shown).

Either of the first portion 1510 and the second portion 1520 can define a fastening element (not shown). In some aspects, the fastening element can comprise threads, which can comprise male or female threads, to facilitate assembly and disassembly of a mating component. In other aspects, the fastening element can comprise a boss protruding from or an indentation defined in a surface of the tube 160. The boss or indentation can facilitate a press-fit assembly or disassembly of a mating portion such as the reed module 150 or the mouthpiece 170. The threads of the fastening element can be of any size or class, including both fine and coarse classifications of any diameter and pitch.

Any portion of the tube 160 can be sized and shaped to receive or be received within any portion of a mating part such as any of the adaptor 110, the mounting plate 120, the joint 130, the body 140, the reed module 150, and the mouthpiece 170. In some aspects, any of the first portion 1510 and the second portion 1520 of the tube 160 can be sized and shaped to receive or be received within any of the adaptor 110, the mounting plate 120, the joint 130, the body 140, the reed module 150, and the mouthpiece 170. In other aspects, the bore 168 can be sized to receive any portion of a mating part such as any of the adaptor 110, the mounting plate 120, the joint 130, the body 140, the reed module 150, and the mouthpiece 170. A portion of the tube 160 such as, for example and without limitation, the bore 168 itself can be sized to allow the passage of air completely through the tube 160 from the first end 161 to the second end 162. As shown, a first end 171 of the mouthpiece 170 can be secured to the second end 162 of the tube 160.

Figure 17:
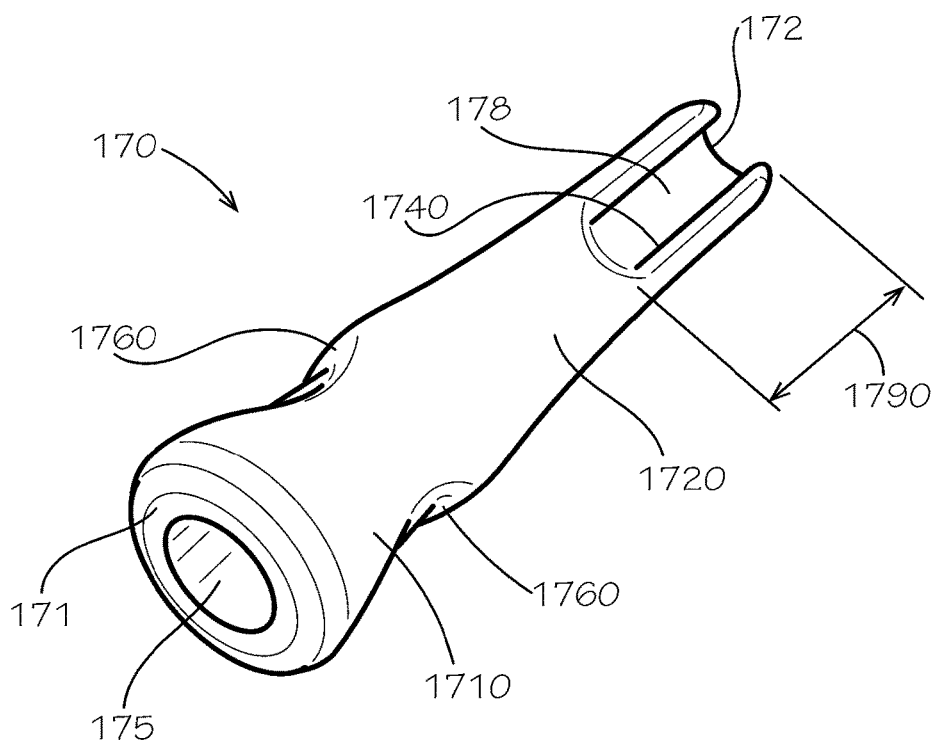
FIG. 17 is a perspective view of a first end of a mouthpiece of the speech assistance device of FIG. 2.
Figure 18:
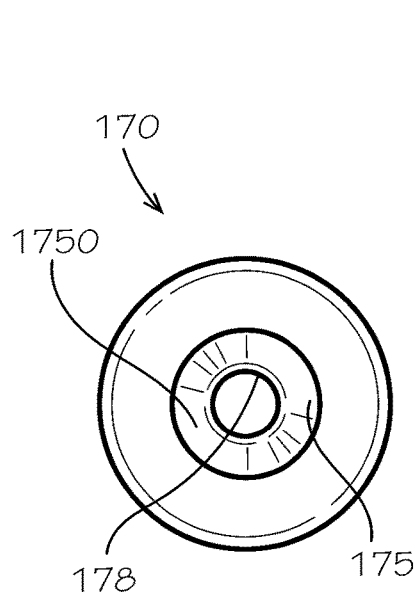
FIG. 18 is an end view of the first end of the mouthpiece of FIG. 17.
Figure 19:
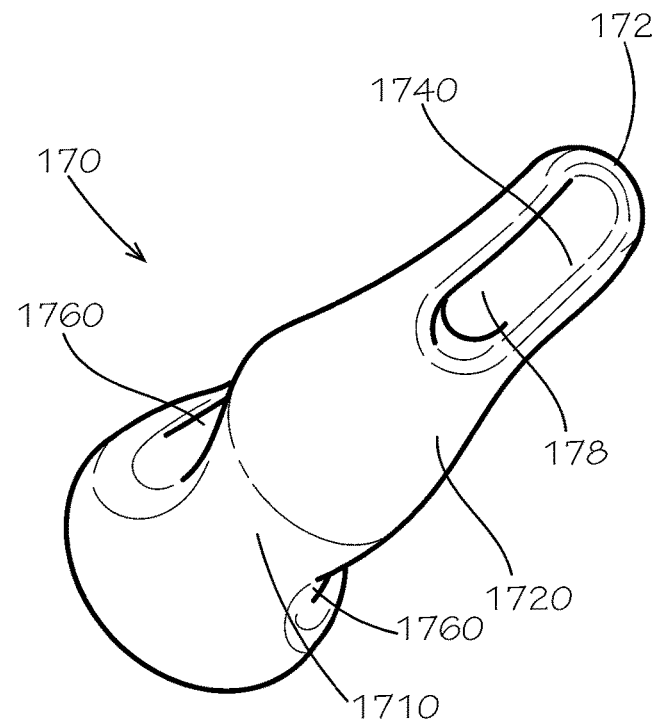
FIG. 19 is a perspective view of a second end of the mouthpiece of FIG. 17.

As shown in FIGS. 17-19, the mouthpiece 170, which as will be described can be configured to be inserted into a mouth 56 (shown in FIG. 24) of the user 50, can define a first end 171 and a second end 172. The mouthpiece 170 can define a cavity 175, which can be defined proximate to, for example and without limitation, the first end 171. In some aspects, the cavity 175 can define a cylindrical shape, in whole or in part. In other aspects, the mouthpiece 170 at the cavity 175 can comprise a non-cylindrical shape. The mouthpiece 170 can define a bore 178, which can be defined proximate to, for example and without limitation, each of the first end 171 and the second end 172. The mouthpiece 170 can define an axis (not shown), along or about which the bore 178 or any other feature can be aligned. In some aspects, a first end surface of the mouthpiece 170 can have a flat shape (i.e., can comprise a planar surface), which can be sized and shaped to facilitate receipt of or mating with a portion of a mating part such as the second end 162 of the tube 160. In other aspects, the first end surface of the mouthpiece 170 can define any other shape.

In some aspects, an outer surface or an inner surface or both an outer surface and an inner surface of any of a first portion 1710 and a second portion 1720 of the mouthpiece 170 can define or have the shape of a truncated paraboloid, in whole or in part. In other aspects, such a surface of any of the first portion 1510 and the second portion 1520 of the tube 160 can define or have a frustoconical shape, in whole or in part. In other aspects, such a surface of any of the first portion 1710 and the second portion 1720 of the mouthpiece 170 can define or have a cylindrical shape, in whole or in part. In other aspects, such a surface of any of the first portion 1710 and the second portion 1720 of the mouthpiece 170 can define or have any other shape as desired such as a conical, tapered, spherical or ball surface, with or without truncation, in whole or in part. The shape of any of the first portion 1710 and the second portion 1720 of the mouthpiece 170 can be such that rotation of the mouthpiece 170, in whole or in part, or a part mated to it about one or more axes is possible.

Either of the first portion 1710 or the second portion 1720 can define a stop surface 1750 by which insertion of the mouthpiece 170 in an axial direction into or about a mating component such as the tube 160 can be controlled, limited, or maintained. Any surface of either of the first portion 1710 and the second portion 1720 can further define indentations 1760. In some aspects, the indentations 1760 can facilitate general holding or gripping of the device 100 by the user 50 or holding or gripping of the mouthpiece 170 to facilitate assembly or disassembly of a mating portion such as the tube 160. In other aspects, the indentations 1760 can increase the strength—or, more specifically, the rigidity—of the mouthpiece 170 by increasing its resistance to deformation when gripped or otherwise manipulated. In other aspects, the indentations 1760 can facilitate thinning of a material thickness of the mouthpiece 170 beyond a point that would otherwise be desirable when the mouthpiece 170 does not define the indentations 1760. As shown, the indentations 1760 can facilitate insertion in and comfortable gripping by the mouth 56 (shown in FIG. 24) of the user 50.

The mouthpiece 170, or any other portion of the device 100 that is configured to be inserted into the mouth—such as, for example, the tube 160 without the mouthpiece 170—can further define a vent 1740 proximate to the second end 172. The vent 1740, which can be a slot as shown or any other opening such as a circular or non-circular opening defined in a surface of the mouthpiece 170, can allow movement of air into and out of the bore 178 of the mouthpiece 170 even when the mouth 56 of the user 50 is otherwise closed around the mouthpiece 170 but not blocking entirely the vent 1740. The vent 1740 can sit on the teeth or on the palate and can shield the mouthpiece 170 and the bore 178 from movement of the tongue of the user 50. The vent 1740 can extend through the thickness of a wall of the mouthpiece and can define a vent length 1790, which can extend in an axial direction from the second end 172. The vent 1740 can define a vent width in a transverse direction of the mouthpiece 170—orthogonal to the axial direction—that can be less than a diameter of the portion of the mouthpiece 170 in which it is defined. In some aspects, either of the first portion 1710 and the second portion 1720 can have different shapes for aesthetic and/or functional reasons. In other aspects, either of the first portion 1710 and the second portion 1720 can have shapes that are indistinguishable from each other.

Either of the first portion 1710 and the second portion 1720 can define a fastening element (not shown). In some aspects, the fastening element can comprise threads, which can comprise male or female threads, to facilitate assembly and disassembly of a mating component. In other aspects, the fastening element can comprise a boss protruding from or an indentation defined in a surface of the mouthpiece 170. The boss or indentation can facilitate a press-fit assembly or disassembly of a mating portion such as the tube 160. The threads of the fastening element can be of any size or class, including both fine and coarse classifications of any diameter and pitch.

Any portion of the mouthpiece 170 can be sized and shaped to receive or be received within any portion of a mating part such as any of the adaptor 110, the mounting plate 120, the joint 130, the body 140, the reed module 150, and the tube 160. In some aspects, any of the first portion 1710 and the second portion 1720 of the mouthpiece 170 can be sized and shaped to receive or be received within any of the adaptor 110, the mounting plate 120, the joint 130, the body 140, the reed module 150, and the tube 160. In other aspects, the bore 178 can be sized to receive any portion of a mating part such as any of the adaptor 110, the mounting plate 120, the joint 130, the body 140, the reed module 150, and the tube 160. A portion of the mouthpiece 170 such as, for example and without limitation, the bore 178 itself can be sized to allow the passage of air completely through the mouthpiece 170 from the first end 171 to the second end 172.

In some aspects, as shown in the above-described figures, the tube 160 of the device 100 can be pre-bent or molded in a bent condition such that the tube 160 or mouthpiece 170 is offset or rotated from an otherwise straight condition to facilitate use by the user 50. In other aspects, the tube 160 can be straight. In some aspects, the tube 160 can comprise a moldable material or combination of materials in the sense that the tube 160 can be bent into a shape—a shape that is useful for routing the tube 160 towards the mouth 52 of the user 50—or straightened from a previous bent condition and the tube retain that shape. For example, the tube 160 can comprise a wall material that is flexible to bend into any desired shape but also weak enough not to plastically deform and weaken in the process. At the same, the tube 160 can comprise a wall reinforcement material such as, for example and without limitation, sufficiently large metal rods or a metal mesh, inside a wall of the tube that can plastically deform into a new shape but also be strong enough to retain the new shape.

Figure 20:
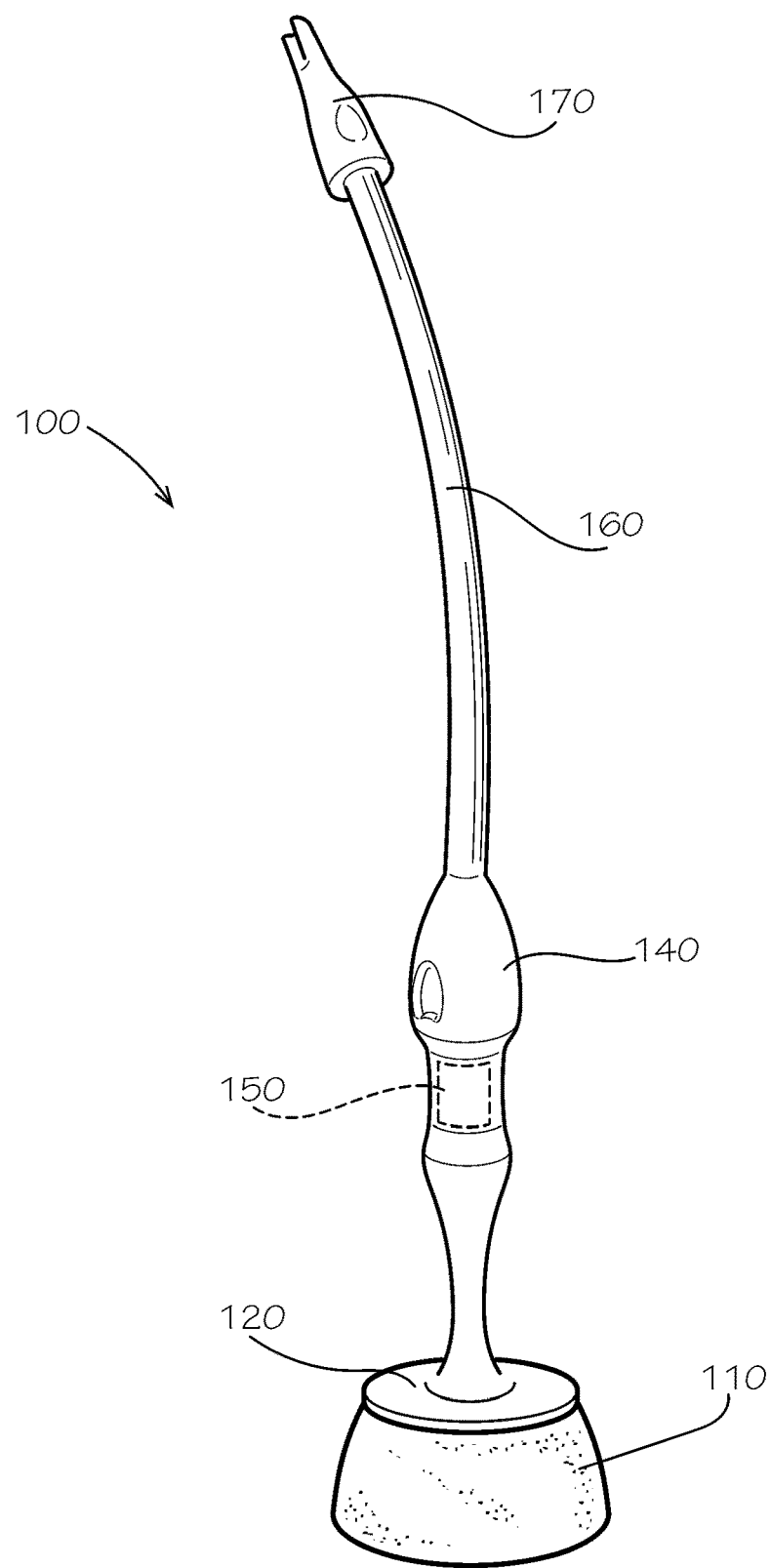
FIG. 20 is a perspective view of the speech assistance device in accordance with another aspect of the current disclosure.

As shown in FIGS. 20-23, the device 100 can be of a "disposable" configuration comprising parts that can, as desired, be assembled, disassembled, and/or modified as needs may arise to replace individual parts but will generally be sealed as shown and not amenable to disassembly and subsequent re-use. As shown in FIG. 20, the device 100 can comprise any one or more of an adaptor 110, a mounting plate 120, a joint (not shown), a body 140, a reed module 150, a tube 160, and a mouthpiece 170. In some aspects, as shown, the device 100 can comprise a monolithically formed body 140, which can itself comprise the mounting plate 120 and the tube 160 and incorporate also a joint such as the joint 130, even if the flexibility of the joint differs due to the monolithic construction compared to the joint 130 that is shown in FIGS. 7 and 8. In other aspects, the body 140 can comprise fewer or greater components. For example and without limitation, the body 140 can still be formed separate from and later joined to any of the adaptor 110, the mounting plate 120, the joint 130, the reed module 150, the tube 160, and the mouthpiece 170. In other aspects, the body 140 can comprise in a monolithic construction not just the mounting plate 120, the tube 160, and the joint 130 but also each of the adaptor 110, the reed module 150, and the mouthpiece 170. In some aspects, as shown, the body 140 can permanently enclose the reed module 150.

In some aspects, the device 100 as shown can be disposable after use because of its particularly low cost of manufacture. The lower cost of manufacture can be based on, for example and without limitation, its fewer number of parts due to the monolithic construction. In other aspects, the device 100 as shown can be used repeatedly over an extended period of time by any single user 50, but the low manufacturing cost can result in many more such users 50 having access to the device 100. As shown, the adaptor 110 and the mouthpiece 170 can be formed separately from the body 140.

Figure 21:
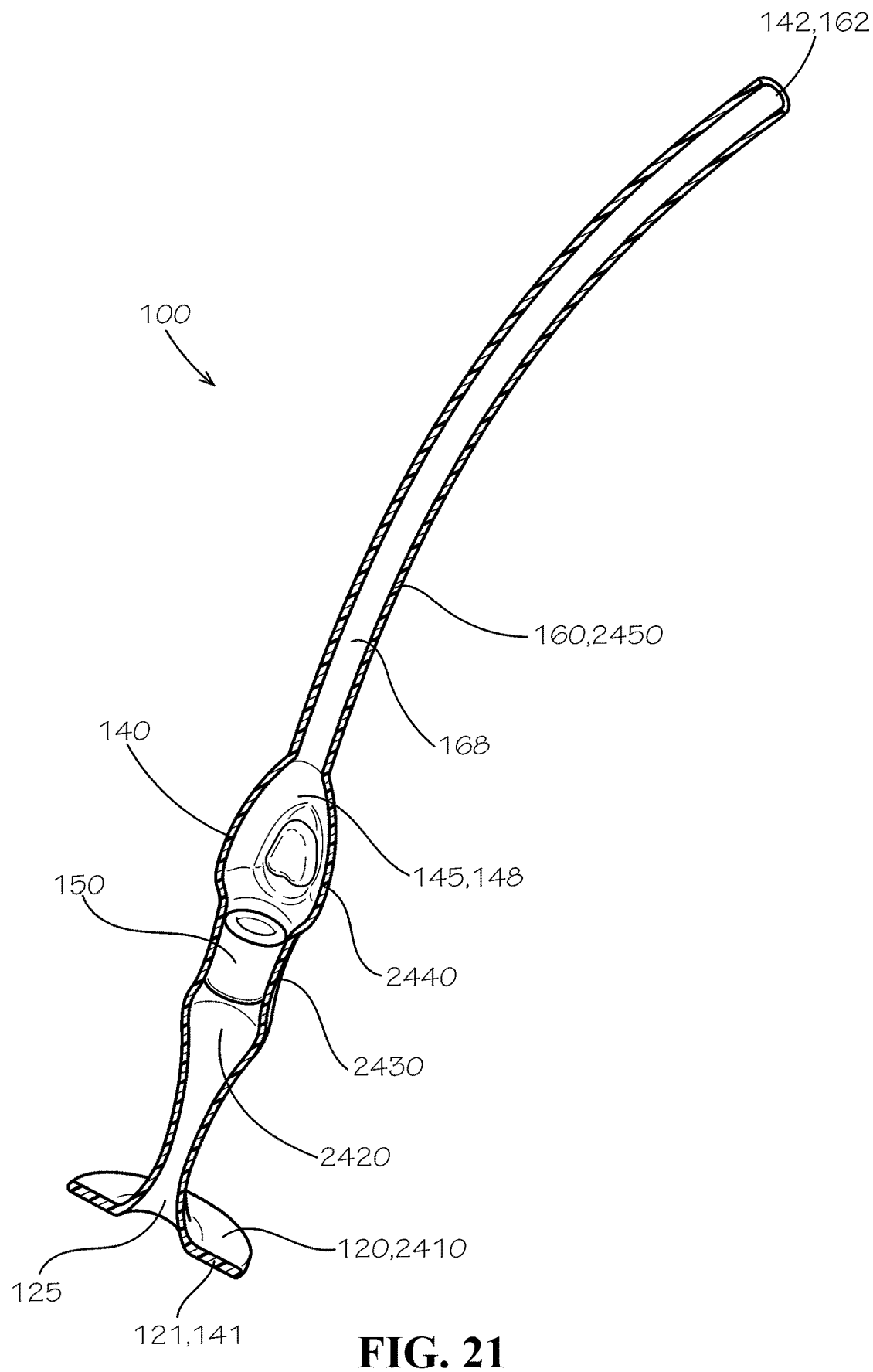
FIG. 21 is a sectional perspective view of a body and a reed module of the speech assistance device of FIG. 20.
Figure 22:
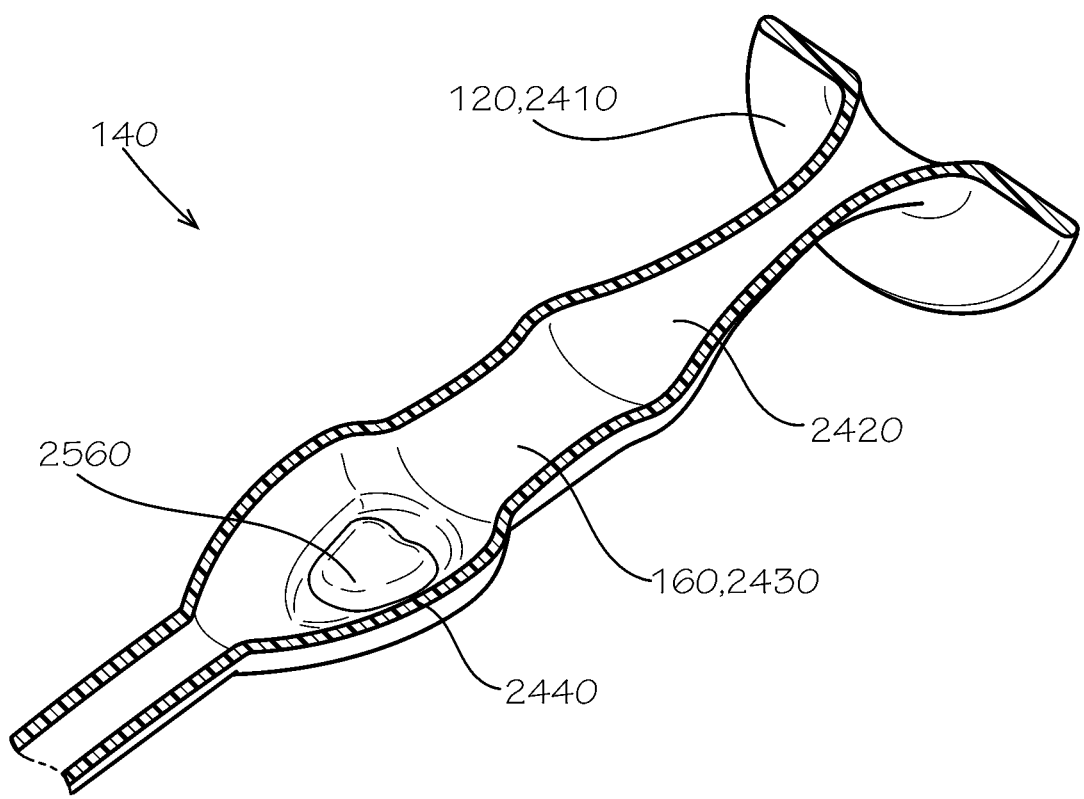
FIG. 22 is a detail sectional perspective view of a portion of the body of the speech assistance device of FIG. 20.

As exemplarily shown in FIGS. 21 and 22, the body 140 can comprise a first portion 2410, which can comprise any or all of the features of a mounting plates such as, for example and without limitation, the mounting plate 120 shown in FIGS. 5 and 6, which can define a cavity 125; a second portion 2420, which can comprise any or all of the features of a joint such as, for example and without limitation, the joint 130 shown in FIGS. 7 and 8; a third portion 2430 and a fourth portion 2440, either of which can comprise any or all of the features of a body such as, for example and without limitation, the body 140 shown in FIGS. 9 and 10 and a reed module such as the reed module 150 shown in FIGS. 11 and 12 or, with a larger body 140 as needed, any of the reed modules 150 shown in FIGS. 13A-D or in FIGS. 14A-E; and a fifth portion 2450, which can comprise any or all of the features of a tube such as, for example and without limitation, the tube 160 shown in FIGS. 15 and 16. Any portion of body 140 such as, for example and without limitation, the third portion 2430 can be or can define a reed module cavity, in which the reed module 150 can be positioned and permanently sealed. By "permanently sealed," it is meant that removal of the reed module 150 is possible only by cutting open or deforming the body 140 or by other destructive means, after which time the device 100 would not generally be expected to function as before such removal, even if an attempt were made to re-install the reed module 150.

In one aspect, as shown in FIG. 22, any portion such as the fourth portion 2440 of the body 140 can define an indentation 2560—shown in FIG. 22 from an inside of the body 140, which can facilitate general holding or gripping of the device 100 by the user 50. In other aspects, the indentation 2560 can increase the strength—or, more specifically, the rigidity—of the body 140 by increasing its resistance to deformation when gripped or otherwise manipulated. In other aspects, the indentations 2560 can facilitate thinning of a material thickness of the body 140 beyond a point that would otherwise be desirable when the body 140 does not define the indentations 2560. In other aspects, an opposing pair of indentations 2560 can reduce the strength of a grip required to hold the body 140 in position during use by, for example, allowing one or more fingers of the user 50 to positively lock in the indentations 2560 and thereby secure the position of the body 140 with less reliance on friction between the fingers and the otherwise smooth surface of the body 140. In other aspects, an opposing pair of indentations 2560, when squeezed to compress the body 140 at or proximate to the indentations 2560, can modulate the operation of the reed module 150 enclosed within the body 140 by mechanical deformation of the body 140 and, by extension, also the reed module 150, or by direct squeezing of the reed module 150. In such case, deformation of the reed module that causes the reed 1300 (such as the reed 1300 shown in FIG. 13A) to tighten or loosen can change the pitch of that sound produced by the reed 1300.

In some aspects, an outer surface or an inner surface or both an outer surface and an inner surface of any of the first portion 2410, the second portion 2420, the third portion 2430, the fourth portion 2440, and the fifth portion 2450 of the body 140 can define or have the shape of a truncated paraboloid, in whole or in part. In other aspects, such a surface of any of the first portion 2410, the second portion 2420, the third portion 2430, the fourth portion 2440, and the fifth portion 2450 can define or have a frustoconical shape, in whole or in part. In other aspects, such a surface of any of the first portion 2410, the second portion 2420, the third portion 2430, the fourth portion 2440, and the fifth portion 2450 can define or have a cylindrical shape, in whole or in part. In other aspects, such a surface of any of the first portion 2410, the second portion 2420, the third portion 2430, the fourth portion 2440, and the fifth portion 2450 can define or have any other shape as desired such as a conical, tapered, spherical or ball surface, with or without truncation, in whole or in part. As shown, the first portion 2410 defines both planar and parabolic surfaces; the second portion 2420 defines a parabolic surface; the third portion 2430 defines a cylindrical surfaces; the fourth portion 2440 defines a combination of parabolic and frustoconical or conical surfaces; and the fifth portion 2550, when straightened, defines a cylindrical surface. The shape and material properties of any of the first portion 2410, the second portion 2420, the third portion 2430, the fourth portion 2440, and the fifth portion 2450 can be such that rotation of one portion with respect to the other about one or more axes is possible.

Figure 23:
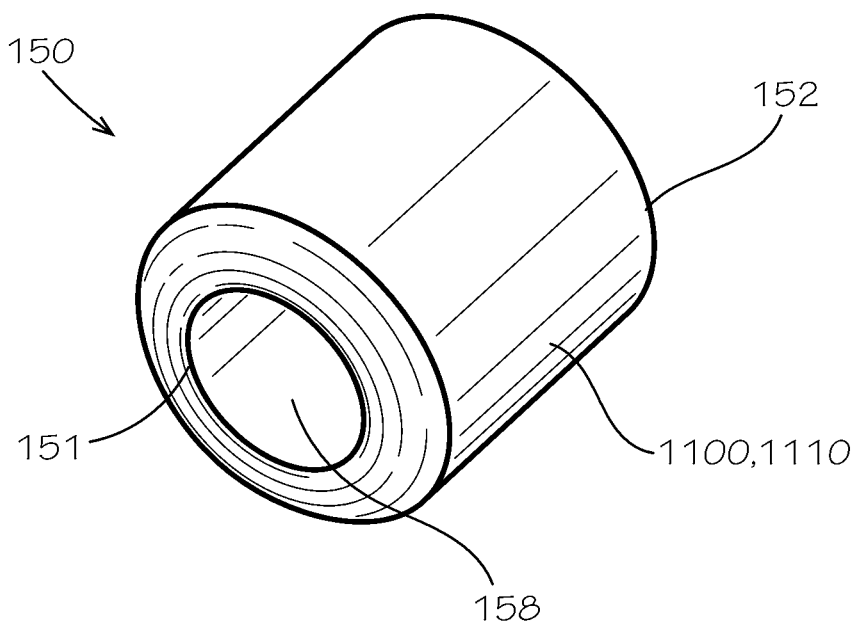
FIG. 23 is a detail perspective view of the reed module of the speech assistance device of FIG. 20.

The reed holder 1100 of the reed module 150 can define an outer surface or an inner surface or, as shown in FIG. 23, both an outer surface and an inner surface defining a cylindrical shape. The reed 1300 (shown in FIG. 13A) can be attached to the reed module 150 as exemplarily shown in FIGS. 13A-13B or in FIGS. 14A-14B.

Figure 24:
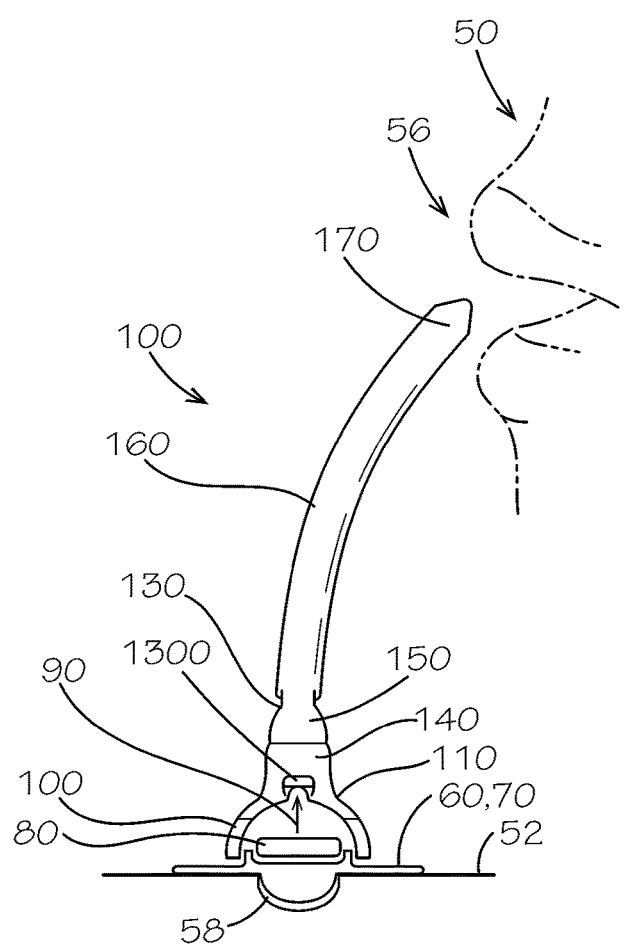
FIG. 24 is a partial sectional view of the speech assistance device in accordance with another aspect of the current disclosure.

As shown in FIG. 24, the joint 130 can be positioned between the reed module 150 and the tube 160. Indeed, the position of any of the parts of the device 100 including the adaptor 110, the mounting plate 120, the joint 130, the body 140, the reed module 150, the tube 160, and the mouthpiece 170 can be different than that disclosed in the figures. For example and without limitation, in other aspects, the joint 130 can be positioned between the tube 160 and the mouthpiece 170, the reed module 150 can be positioned between the tube 160 and the mouthpiece 170, and so forth. Also as shown and noted above, the mouthpiece 170 need not be present or can be incorporated into the design of the tube 160.

In some aspects, as also shown, the surface of the neck 52 can be flat in cross-section. In other aspects, however, the surface of the neck 52 can be non-flat in cross-section or flat in one sectional view but non-flat in other sectional views. Wth or without the neck accessory 60, the stoma 58 can be fitted with the HME cassette 80 (which, again, known devices have not been able to accommodate). As shown, it can be advantageous for the adaptor 110 to not only fit over and around the HME cassette 80, it can be advantageous for the adaptor to be configured to compressibly seal against the surface of the neck accessory 60 or the neck 52, including when the stoma 58 varies in shape—as it typically will for each patient based on the patient's particular anatomy and any neck accessory 60 that can be fit over it. Such compression can be facilitated by use of a soft, compressible, and pliable material such as, for example and without limitation, foam. In some aspects, as shown, just a portion of the adaptor 110 can comprise the compressible material. In other aspects, as shown in FIG. 3, the entire adaptor 110 can comprise the compressible material.

In some aspects, any of the edges of the parts disclosed herein can be sharp where adjoining surfaces intersect or can otherwise be formed without a radius. In other aspects, any of these same edges can incorporate a radius or chamfer or other edge treatment or be replaced with a radiused or chamfered or other non-sharp edge for advantageous reasons such as, for example and without limitation, safety or aesthetics.

In some aspects, any of the parts described herein can have a constant thickness. In other aspects, any of the parts can have a variable thickness. In some aspects, the respective bores 118,128,138,148,158,168,178—which together can form a device bore 108 (shown in FIG. 2)—can have an internal diameter D that is constant along an axial direction.

In other aspects, the internal diameter D of the respective bores 118, 128, 138, 148, 158, 168, 178 can vary along an axial direction. Such variance in the internal diameter can be, for example and without limitation, to facilitate a constant wall thickness throughout or for other functional or aesthetic considerations.

In some aspects, no separate seal is necessary between assembled parts. In other aspects, a seal (not shown) such as, for example and without limitation, a gasket or washer or liquid adhesive or liquid sealant (at least as dispensed) can be present between any of the parts described herein to prevent air and/or moisture leakage into or from adjoining parts.

The components of any of the devices 100 disclosed above or below can comprise any one or more of a number of different materials. In some aspects, any of the adaptor 110, the mounting plate 120, the joint 130, the body 140, the reed module 150, the tube 160, and the mouthpiece 170 can comprise any one or more of a number of different materials such as, for example and without limitation, a metallic, polymeric, rubber, or composite material. In some aspects, to facilitate low cost, dimensional stability, and tight tolerances, any of the parts can be molded from or can comprise any one or more of a variety of engineered polymers such as, for example and without limitation, a terpolymer such as acrylonitrile butadiene styrene (ABS), a polyamide such as NYLON-brand resin from DuPont, and an acetal like DELRIN-brand resin from DuPont. In other aspects, any of the parts can be molded from or can comprise any one or more of a variety of other synthetic or natural materials such as, for example and without limitation, silicone, natural rubber, or synthetic rubber. In some aspects, the material used to form any of the adaptor 110, the mounting plate 120, the joint 130, the body 140, the reed module 150, the tube 160, and the mouthpiece 170 can be rigid. In other aspects, the material used to form any of the adaptor 110, the mounting plate 120, the joint 130, the body 140, the reed module 150, the tube 160, and the mouthpiece 170 can be flexible.

In some aspects, the adaptor 110 can comprise a material such as foam that is flexible and compressible. In other aspects, the adaptor 110 can comprise any other material, including a material that is not flexible or compressible. The material of the adaptor 110 can be non-porous such that air and other fluids will not pass through the material and such that the adaptor 110 can be easily cleaned.

In some aspects, the reed 1300 can comprise a natural material such as, for example and without limitation, parchment or another wood product. In other aspects, the reed 1300 can comprise a man-made or synthetic material such as, for example and without limitation, polycarbonate (PC) or acrylic. A pitch of the voice produced by the user using the device 100 can be adjusted to match that recognizable as a male, female, adult, or children's voice depending on the preferences of the user 50. In some aspects, this adjustment can be made by, for example and without limitation, adjusting a width, a thickness, a length, a material, and/or a resulting vibratory capacity of the reed 1300 itself—thinner and tighter generally producing a higher voice, not unlike the actual vocal folds of a human—instead of the user 50 always having a male voice, which is typical for the device 100 of the pneumatic and electrolarynx varieties made available in the past. As described below, the entire reed module 150 can be easily replaceable as a unit to accomplish such an adjustment. For example, the reed module 150 can be calibrated to facilitate production of a male voice or a female voice and replaced with another reed module 150 already calibrated to facilitate production of another voice.

In other aspects, the reed 1300 could be made in structure and in function like that of a musical instrument. For example and without limitation, the reed 1300, which can comprise two parts that come together, can produce sound at various pitches when air passes through or between it depending on airflow through and tension (and other mechanical and material properties) of the reed 1300.

In some aspects, no adhesive is necessary between mating parts. In other aspects, an adhesive can be used to join mating parts. In some aspects, any of the adaptor 110, the mounting plate 120, the joint 130, the body 140, the reed module 150, the tube 160, and the mouthpiece 170 can be joined to each other using a friction fit connection, a snap-fit connection, a threaded connection, a magnetic connection, a fastener, or any other connection as desired.

The components of any of the devices 100 disclosed above or below can manufactured using any one or more of a number of different processes. In some aspects, any of the adaptor 110, the mounting plate 120, the joint 130, the body 140, the reed module 150, the tube 160, and the mouthpiece 170 can be manufactured using a molding process such as injection molding. In other aspects, any of these same parts can be manufactured through an additive manufacturing process such as, for example and without limitation, three-dimensional printing or through a subtractive manufacturing process such as, for example and without limitation, machining.

Figure 25:
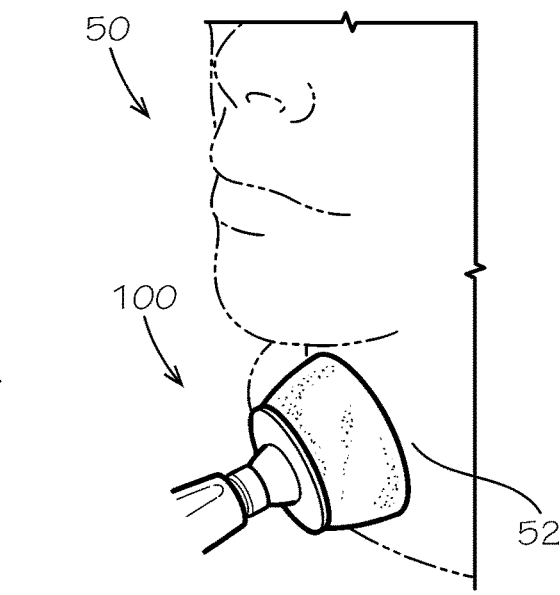
FIG. 25 is a partial sectional view of the speech assistance device as placed against the neck of the user in accordance with another aspect of the current disclosure.

As shown in FIG. 25, the device 100 can be placed against the neck 52 of the user 50. The device 100 and in particular the adaptor 110 can seal around the open stoma 58 or the neck accessory 60 (shown in FIG. 1) such that all air 90 (shown in FIG. 24) driven by the lungs through the stoma 58 (shown in FIG. 24) is pushed through the device 100 instead of leaking out in a gap between the stoma 58 or the neck accessory 60 and the adaptor 110. Leaking due to an incomplete seal of the adaptor 110 against the neck 52 proximate to the stoma 58 or the neck accessory 60 can mean that the user 50 will have to deliver more air to the device 100 than if the seal were complete as shown. In some aspects, the user 50 can apply more pressure to the device 100, can rotate or reposition the device 100, or can rotate or otherwise move his or her body (including, e.g., the neck or chin) to better seal a connection between the device 100 and the user 50 and thereby reduce or eliminate leakage therebetween. In some aspects, the adaptor 100 of any of the devices 100 disclosed herein can be specifically shaped to match particular geometry of the neck 52, the stoma 58, and/or the neck accessory 60 of the particular user 50.

Figure 26:
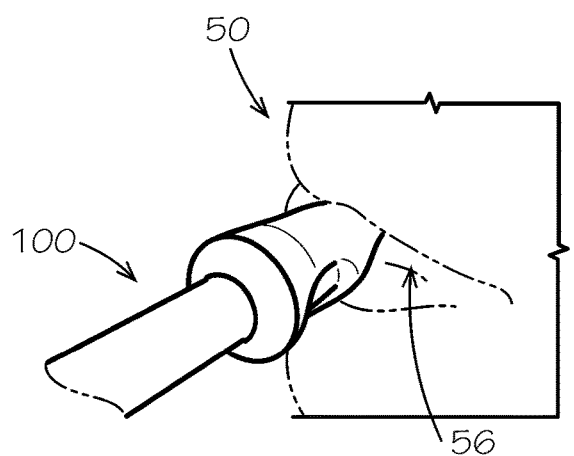
FIG. 26 is a perspective view of the mouthpiece of FIG. 17 inserted into a mouth of the user of the speech assistance device of FIG. 3.

As shown in FIG. 26, the mouthpiece 170 of the device 100 can be inserted into the mouth 56 of the user 50. The air 90 (shown in FIG. 24) pushed through the device bore 108 (shown in FIG. 2) can then form a sound as it passes the reed 1300 or the reeds 1300a,b and can be translated into intelligible letters, words, and other expressions as it enters the mouth 56 by modulation of the air through manipulation of the oral cavity, tongue, teeth, lips, and so forth.

In other aspects, instead of pushing air through the device 100 with the air 90 expelled by the user 50, a compact fan or other air flow device can either replace the adaptor 110 or mate with the adaptor 110 to produce a steady flow. Furthermore, such flow of the air 90 from such a separate air source can be separately adjusted using a method such as, for example and without limitation, that used in an electrolarynx to module changes in the vibrations produced by the electrolarynx.

Figure 27:
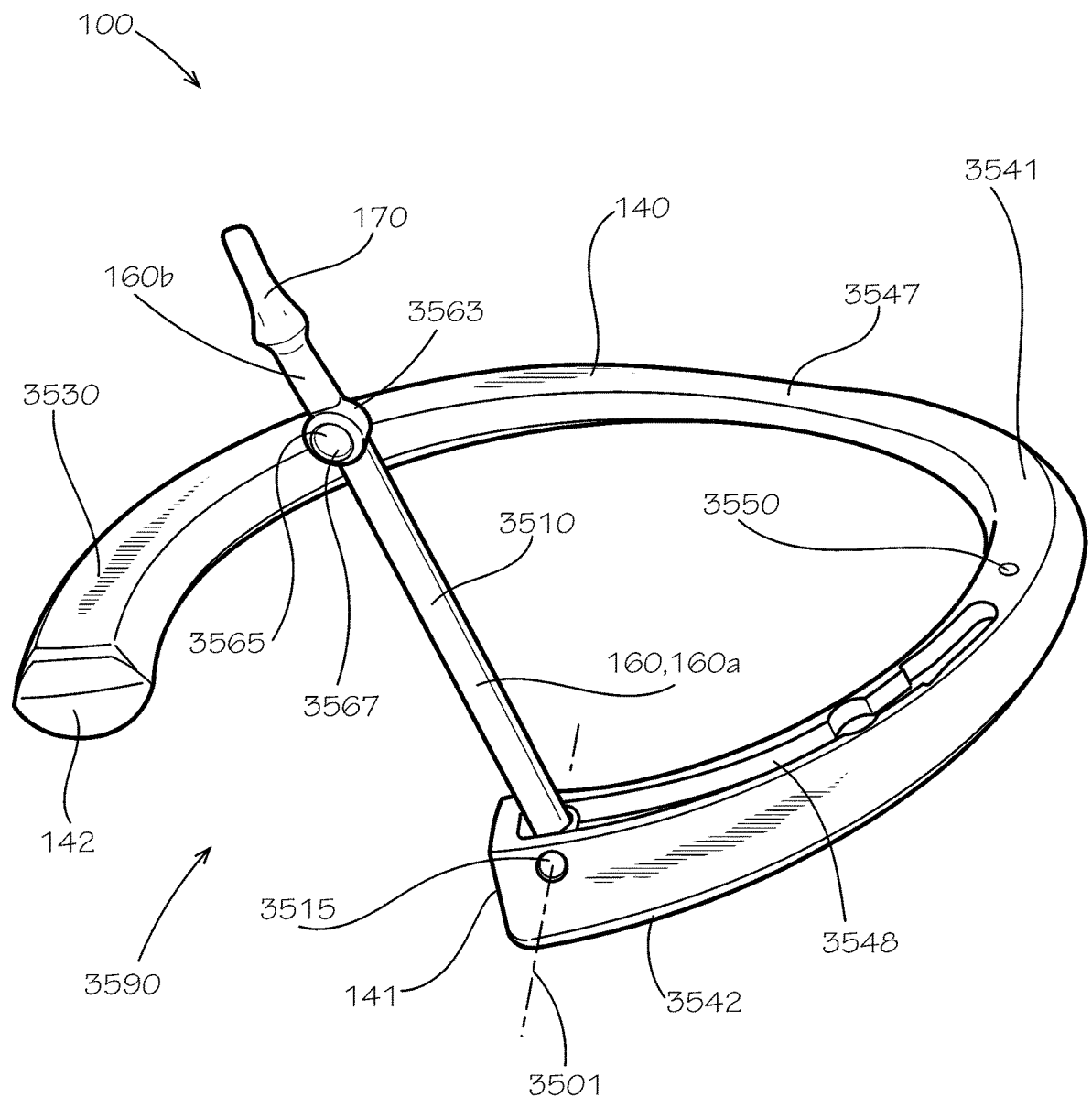
FIG. 27 is a perspective view of a speech assistance device in accordance with another aspect of the current disclosure.
Figure 29:
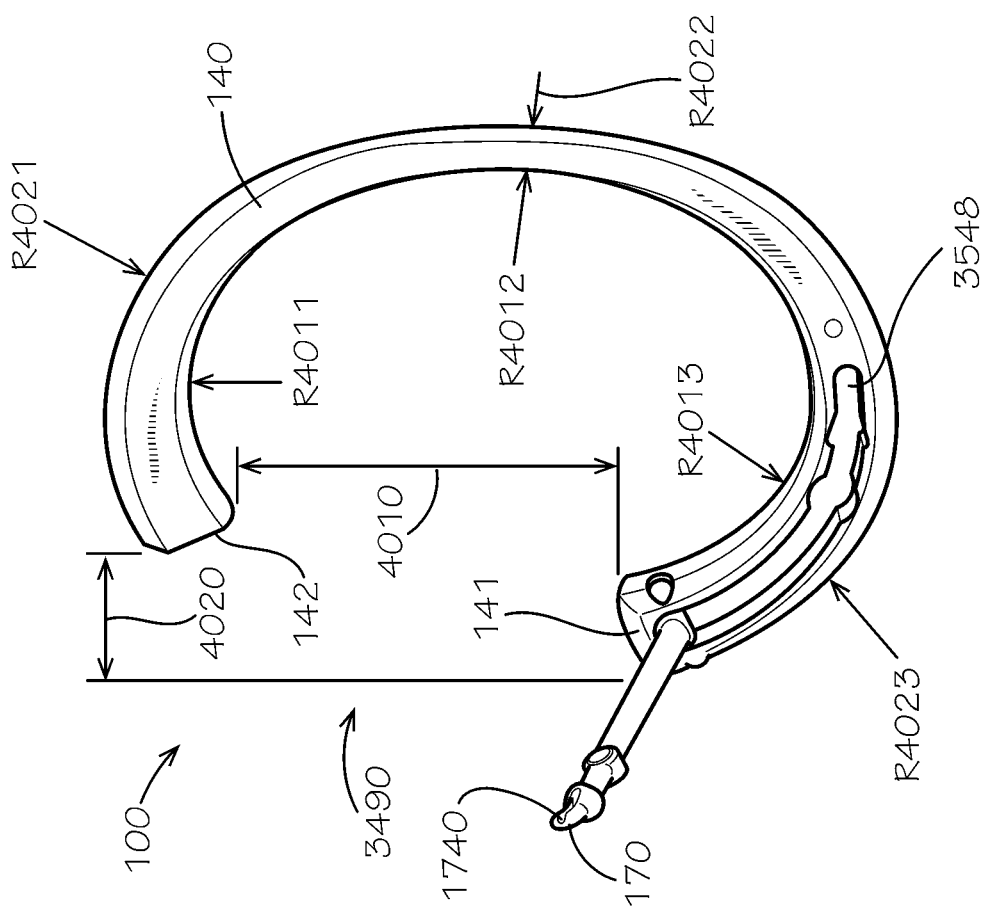
FIG. 29 is a top view of the speech assistance device of FIG. 34.
Figure 28:
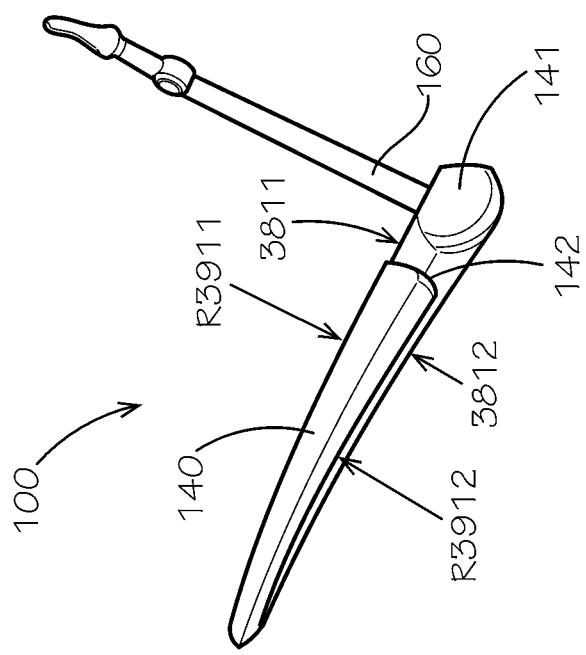
FIG. 28 is a side view of the speech assistance device of FIG. 34.

As shown in FIGS. 27-29, the device 100 can comprise a body 140, which can define or have the shape of an open ring configured to be worn around the neck of the user 50. As shown in FIG. 27, the body 140 can comprise the first end 141 and the second end 142, which can define the ends of the ring shape and an opening 3590 therebetween. The body 140 can define an upper surface 3541 and a lower surface 3542. In some aspects, the body 140 can define a constant thickness in either of a radial direction from a center of a local radius of the body 140 and a direction perpendicular to the upper surface 3541 or the lower surface 3542. In other aspects, the body 140 can vary in thickness in either orientation or in any other orientation. In some aspects, as shown, a thickness of the body 140 can be thinnest at a position between the first end 141 and the second end 142 such as, for example and without limitation, a rear portion 3547. In other aspects, the thickness of the body 140 can be thinnest at either the first end 141 or the second end 142.

The body can define an arm cavity 3548, which can be sized and shaped to at least partially receive an arm 3510 in either an extended or a retracted condition. In some aspects, the arm cavity 3548 can be defined in the body 140 proximate to the first end 141. In other aspects, the arm cavity 3548 can be defined in the body 140 proximate to the second end 142. In other aspects, the arm cavity 3548 can be defined in the body 140 distal from both the first end 141 and the second end 142. The body 140 can comprise a cover 3530, behind which controls, a power supply comprising, for example and without limitation, one or more batteries, or other components can be housed, including any of the other components disclosed herein. The cover 3530 can be removable to access such components. The body 140 can also define one or more connection ports (not shown) for, e.g., recharging the batteries of the device 100 or for the uploading or downloading of data to or from the device 100.

As shown, the device 100 can further comprise the arm 3510, which can be an elongated element configured to be extend from the body 140 to the mouth 56 of the user 50. The arm 3510 can be coupled to the body 140. The arm 3510 can comprise the tube 160—more specifically tubes 160a,b, which can be configured to be inserted into the mouth 56 of the user 50. The tube 160 can comprise the mouthpiece 170. In some aspects, the tube 160 can be flexible enough to bend into any position in the oral cavity 51 (shown in FIG. 48). In other aspects, the tube 160 can be rigid enough to retain its shape in an open extended position in order to facilitate rapid positioning for speech and define a sufficient wall thickness so as also not to collapse or kink and therefore affect sound conduction through the tube 160. The arm 3510 can pivot about a pivot axis 3501 defined by a pivot 3515, which can comprise a pivot pin as shown.

As shown, the arm 3510 can comprise a housing 3563. In some aspects, the housing 3563 can house or comprise a switch 3565. In other aspects, the housing 3563 can house or comprise a sound transducer 3567, which can be a speaker. The housing 3563 can also house or comprise both a switch 3565 and a sound transducer 3567. In other aspects, the switch 3565 or the housing 3563 can be located anywhere else on the device 100 including, for example and without limitation, on the body 140. Either of the sound transducer 3567 or the switch 3565 can be coupled to the tube 160. In some aspects, functioning in some respects as an improved electrolarynx, by activation of the switch 3565 or by any other desired method, the sound transducer 3567 can direct, transmit, or conduct sound or other vibrations through the tube 160, which can be hollow, up the arm 3510 towards the mouthpiece 170 and into the oral cavity of the user 50.

The power setting or status of the device 100 can be indicated on the device 100 itself by an indicator 3550, which can be a power indicator. In other aspects, the indicator 3550 can be used to display or signal other information about the device.

As shown in FIG. 27, the lower surface 3542 of the body 140 can define a smoothly radiused surface. As shown in FIG. 28, the body 140 can define an upper radius R3811 and a lower radius R3812 proximate to a first side of the device 100 and can define an upper radius R3911 and a lower radius R3912 proximate to a second side of the device 100. Any of the aforementioned radii can be sized to facilitate a comfortable and secure fit of the device 100 around the neck 52 and on a shoulder or shoulders 57 (shown in FIG. 32) of the user 50.

As shown in FIG. 29, the mouthpiece 170 can define the aforementioned vent 1740. As also shown, the body 140 can define an inner radius R4011 proximate to the first end 141, an inner radius R4013 proximate to the second end 142, and an inner radius R4012 measured at a point between the first end 141 and the second end 142. Similarly, the body 140 can define an outer radius R4021 proximate to the first end 141, an outer radius R4023 proximate to the second end 142, and an outer radius R4022 measured at a point between the first end 141 and the second end 142. The opening 3490 can measure an opening width 4010 between the first end 141 and the second end 142 from left to right across the opening 3490. In some aspects, as shown, a forwardmost portion of the second end 142 can be offset from a forwardmost portion of the first end 141 towards the rear by an offset distance 4020. In other aspects, a forwardmost portion of the second end 142 can be offset from a forwardmost portion of the first end 141 towards the front by the offset distance 4020. In other aspects, a forwardmost portion of the second end 142 can be aligned with a forwardmost portion of the first end 141 such that the offset distance 4020 is zero.

Figure 30:
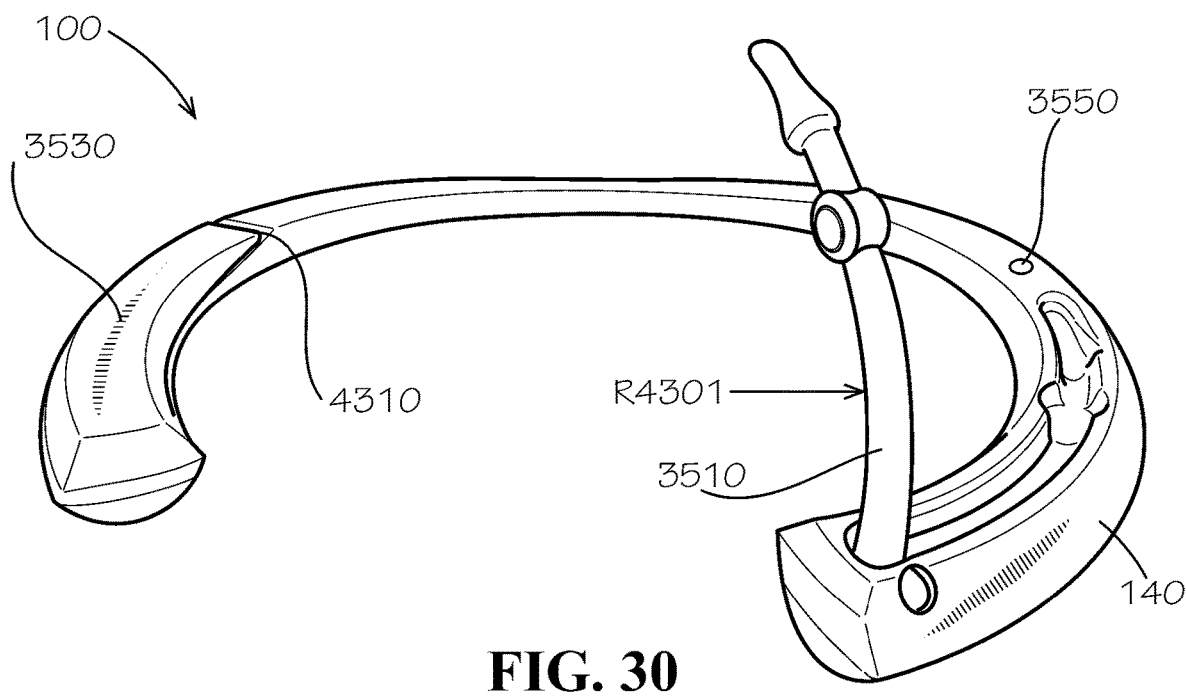
FIG. 30 is a front view of a speech assistance device in accordance with another aspect of the current disclosure.

As shown in FIG. 30, a shape of the arm cavity 3548 can substantially match the shape of the arm 3510 to facilitate retraction of the arm 3510 into or within the body 140. Also as shown, the arm 3510 can be bent at an arm radius R4301—measured in the bend plane of the arm 3510, which can be advantageous to the user 50 by, for example and without limitation, facilitating ergonomic positioning of the mouthpiece 170 relative to the mouth 56 of the user 50 or facilitating retraction of the arm 3510 within the body 140. As shown, removal of the cover 3530 can be facilitated by incorporation of a removal catch 4310, which can be a small cavity defined between a main portion of the body 140 and the cover 3530. As shown, the indicator 3550 can comprise a light source such as, for example and without limitation, a light-emitting diode (LED) and associated circuitry.

Figure 31:
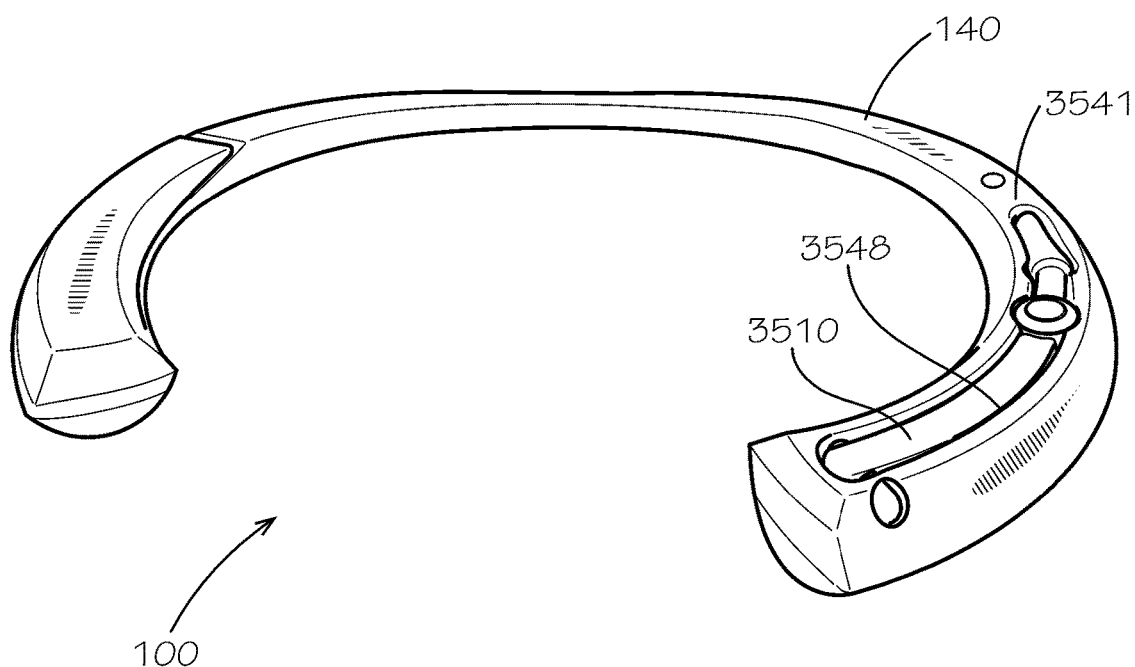
FIG. 31 is a perspective view of the speech assistance device of FIG. 30 with the arm of the device in a retracted condition.

As shown in FIG. 31, the arm 3510 can be retractable into the body 140 and, more specifically, into the arm cavity 3548. As shown, the arm 3510 can sit substantially flush with the upper surface 3541 of the body 140 when the arm 3510 is in a retracted position.

Figure 32:
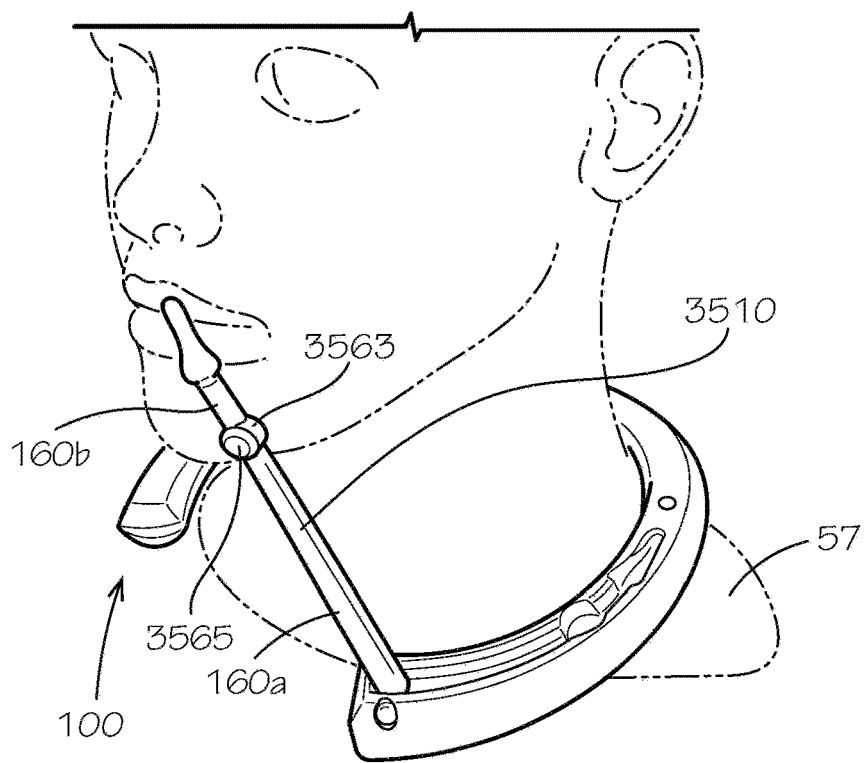
FIG. 32 is a perspective view of the speech assistance device of FIG. 27 as worn by the user with the arm of the device in an extended condition.
Figure 33:
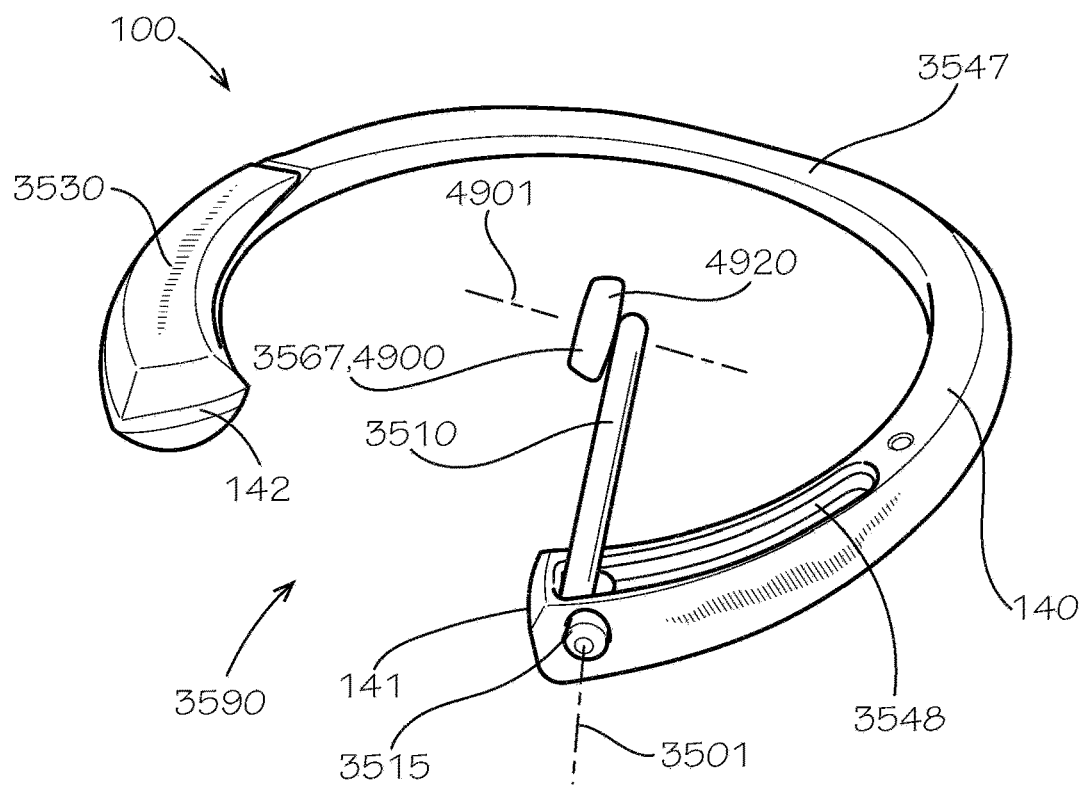
FIG. 33 is a perspective view of the speech assistance device in accordance with another aspect of the current disclosure with the arm of the device in an extended condition.

As shown in FIG. 32, the arm 3510 can be sized and positioned to reach the mouth 56 of the user 50 when the device 100 is wrapped around the neck 52 and supported on the shoulders 57 of the user 50. In some aspects, respective lengths of the tubes 160a,b and an overall length of the arm 3510 can stop short of the mouth 56 so as not to interfere with other user activities, in which case the user 50 can rotate or move his or her mouth 56 towards the arm 3510 to use the device 100 when desired. In other aspects, the arm 3510—and the aforementioned lengths—can be sized and positioned so that the user 50 need not move towards the arm 3510. The switch 3565, shown in an exemplary position that can be moved elsewhere, can be pressed to activate the device 100, the operation of which will be described below.

As shown in FIG. 33-37, the device 100 can comprise a housing 4900, which can be mounted on the arm 3510. In some aspects, the housing 4900 can comprise the sound transducer 3567 or a vibration generator. In other aspects, the sound transducer 3567 can be described as comprising the housing 4900. In other aspects, the housing 4900 can comprise another sound or vibration-forming element. In some aspects, the sound transducer 3567 can be positioned inside the body 140, and the sound produced by the sound transducer 3567 can be directed or transmitted through the body 140 and the tube 160 to the mouthpiece 170. In other aspects, the sound transducer 3567 can be pivotably mounted on the arm 3510 inside the housing 4900. The housing 4900 can be configured to rotate about an axis 4901. The housing 4900 can comprise a first side surface 4910 (shown in FIG. 35), a second side surface 4920 distal from the first side surface 4910, a first end surface 4930 (shown in FIG. 35), and a second end surface 4940 (shown in FIG. 35) distal from the first end surface 4930. The housing 4900 can comprise the sound transducer 3567 (shown in FIG. 35), from which sound can be made to emanate. The sound transducer 3567 can comprise or be accompanied by the switch 3565, which can be used to activate the sound transducer 3567 or the housing 4900 generally. The frequency of the sound and the vibrations produced by the sound transducer 3567 can be adjusted. For example and without limitation, as will be described below, sound can be recorded prior to surgery and the same sound or any portion of it—in other words, it can be modified for clarity or to change any of its characteristics—can be loaded onto the device 100, activation of which can be direct or by remote or wireless operation.

Figure 34:
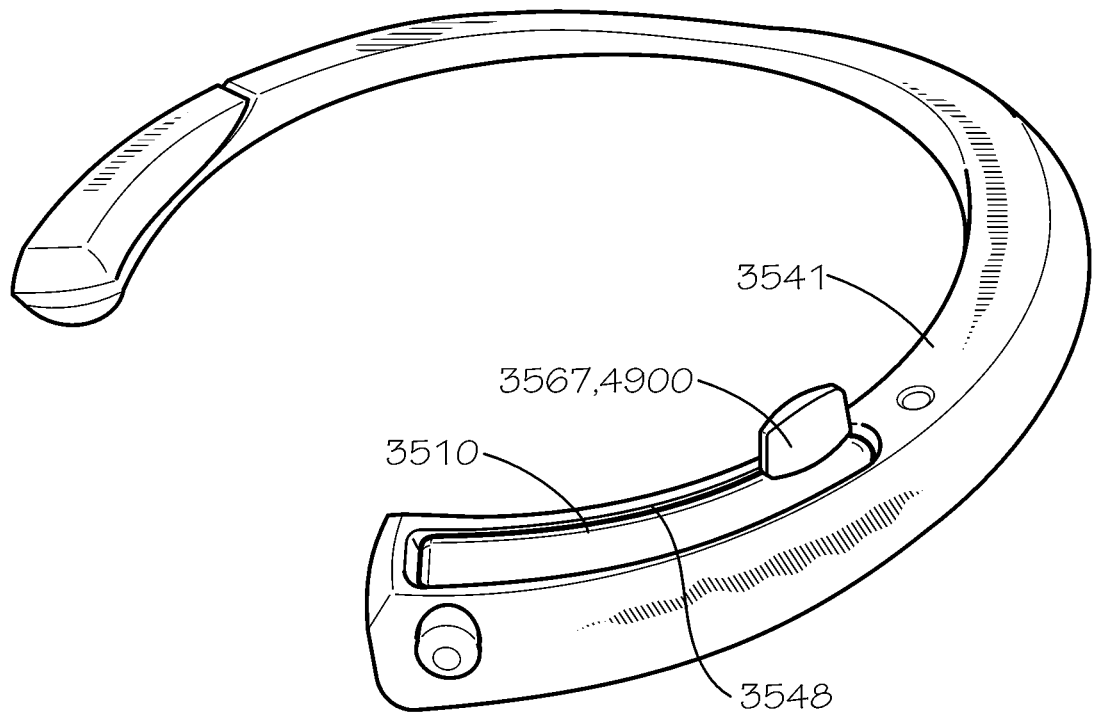
FIG. 34 is a front perspective view of the speech assistance device of FIG. 33 with the arm of the device in a retracted condition.
Figure 35:
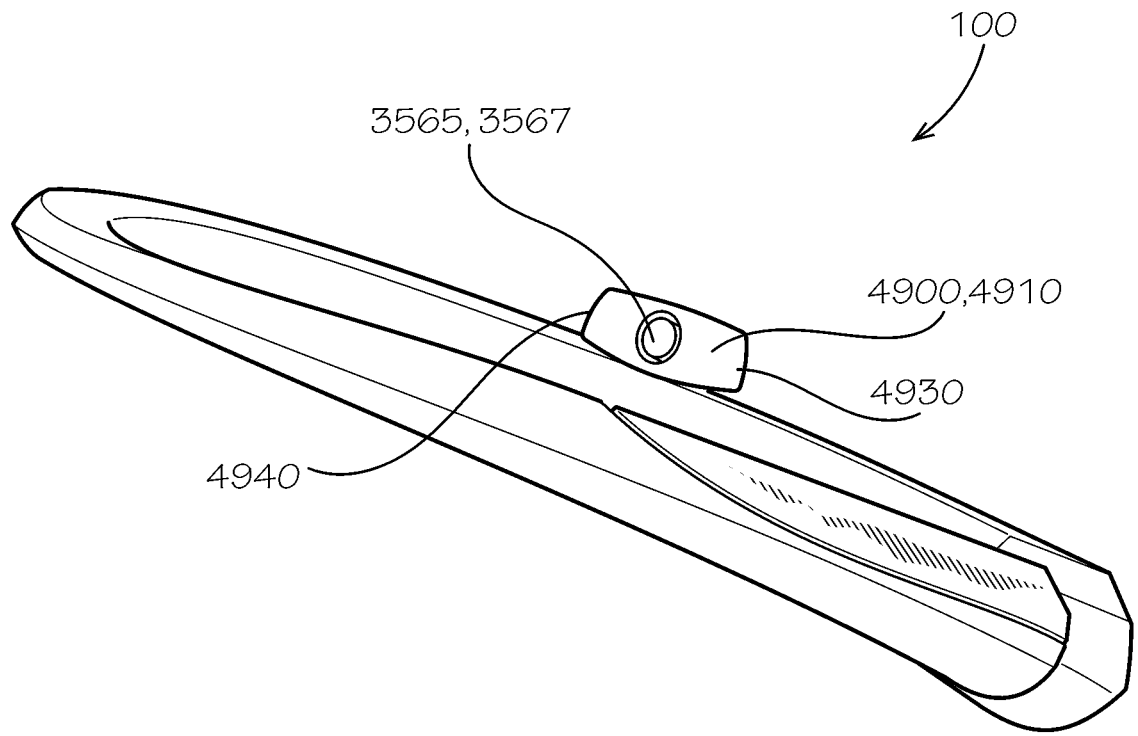
FIG. 35 is a side view of the speech assistance device of FIG. 33.

As shown in FIG. 34, the arm 3510, when in the retracted position, can fit within the arm cavity 3548. In some aspects, as shown, the housing 4900 can protrude beyond the upper surface 3541 of the body 140. In other aspects, the housing 4900 can sit flush with the upper surface 3541.

Figure 36:
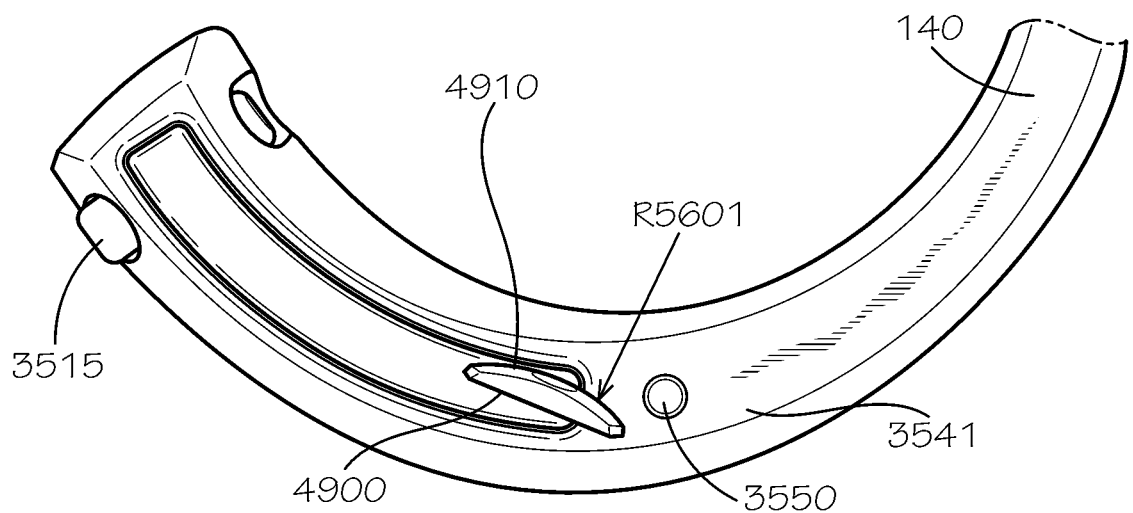
FIG. 36 is a partial top view of the speech assistance device of FIG. 33.

As shown in FIG. 36, the first side surface 4910 of the housing 4900 can be curved and can thereby define a radius R5601.

Figure 37:
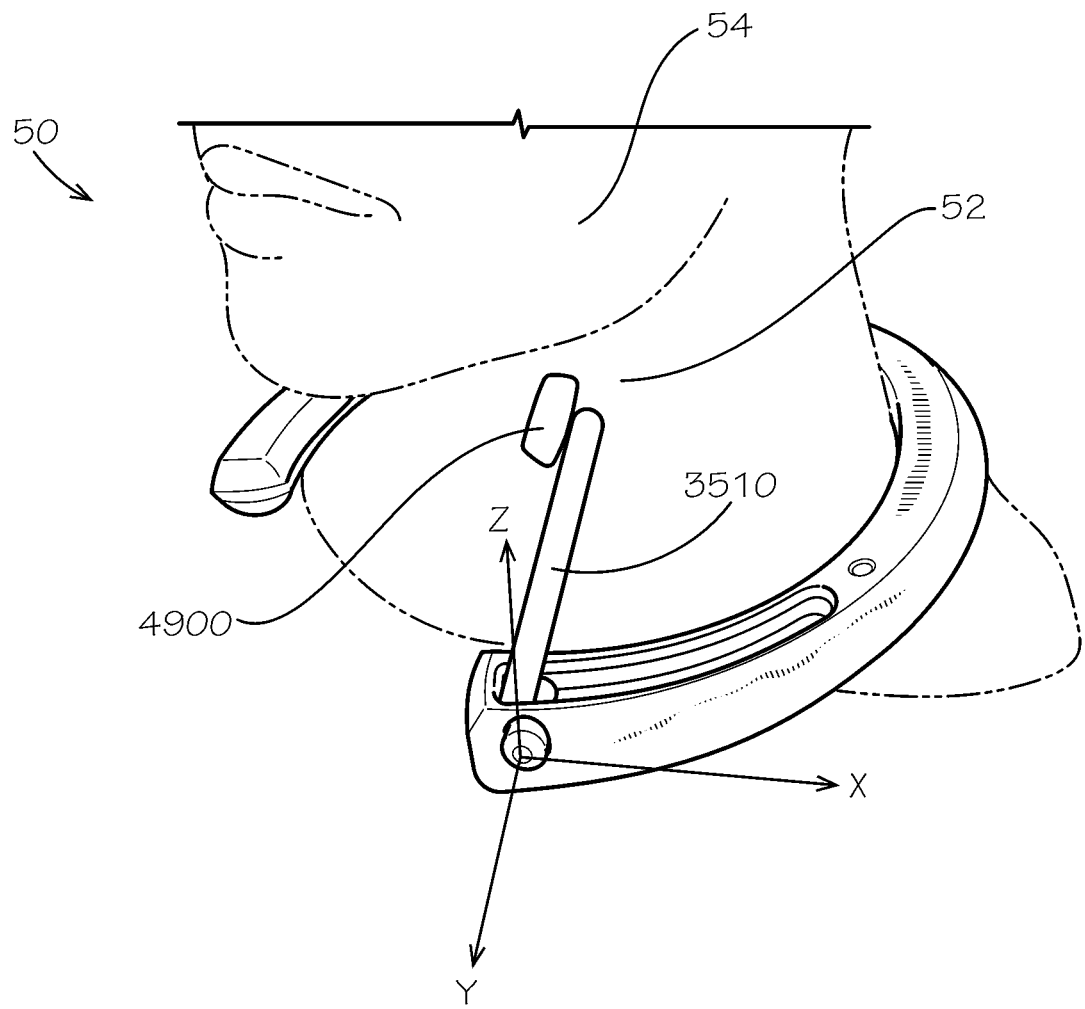
FIG. 37 is a perspective view of the speech assistance device of FIG. 33 as worn by the user.

In some aspects, as shown in FIG. 37, the housing 4900 can be placed in contact with the neck 52 of the user during use. In other aspects, the housing 4900 can be placed in contact with a cheek 54 of the user. In other aspects, the housing 4900 can be placed in contact with another portion of the user 50. In each location, the housing 4900 can be configured to contact the neck 52 of the user 50 and transmit vibrations to the oral cavity of the user 50, which as previously described can be manipulated to produce speech. In some aspects, the user 50 can cause the housing 4900 to contact the desired surface by manually pressing the housing 4900 against the desired body surface with hand pressure. In other aspects, the user 50 can create the same contact with the housing 4900 by moving his or her head such that the desired body surface presses up against the housing 4900, with or without manual hand pressure. In various aspects, the housing 4900 can be made to contact the desired body surface by the incorporation of a biasing element (not shown). For example and without limitation, a biasing element can cause the arm 3510 and the housing 4900 to naturally bend or rotate, e.g., in an Y-axis direction towards the user 50 (through, for example, rotation about the X-axis). The biasing element can comprise a spring or a portion of the device 100 such as the arm 3510 can be formed from an inherently elastic material and the arm 3510 can be pre-bent—or bent by the user 50—to push up against a body surface such as the neck with manual hand or other pressure. In some aspects, by manual manipulation of the housing 4900 the user 50 can activate the sound transducer 3567. In other aspects, the user 50 can activate the sound transducer 3567 by remote activation with a portable electronic device 7300 (shown in FIG. 45). As shown, the X-Y-Z coordinate axes have an origin that is positioned at a center of rotation of the arm 3510.

Figure 38:
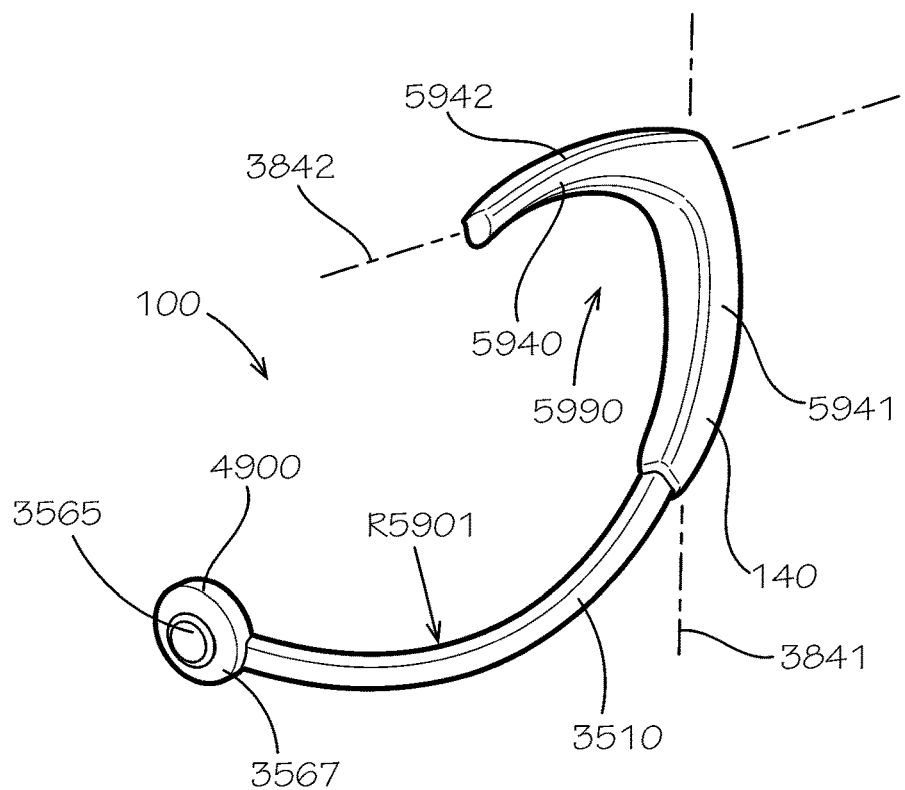
FIG. 38 is a speech assistance device in accordance with another aspect of the current disclosure.

As shown in FIG. 38, the device 100 can comprise a body 140, an arm 3510, and the housing 4900, which again can comprise the sound transducer 3567. The body 140 can comprise an ear attachment hook 5940, which can be configured to detachably secure the body 140 to an ear 59 (shown in FIG. 39) of the user 50. The ear attachment hook 5940, and more generally the body 140 in any of the aspects disclosed herein, can also comprise or house any of the batteries or any of the other components disclosed herein. Such attachment can be aesthetically desirable and more accepted by or more convenient for the user 50 (than, for example, other attachment positions of the device 100) due to the widespread use of wireless phone accessories that can also fit over the ear 59 of the user 50. The ear attachment hook 5940 can define an opening 5990 through which the ear 59 can be received. The opening 5990 can be defined more specifically by a first portion 5941 and a second portion 5942, an orientation direction 3842 of which can be angled with respect to an orientation direction 3841 of the first portion 5941. The arm 3510 can be bent into a radius R5901, whereby the housing 4900 can be brought closer to the desired body surface of the user 50. The housing 4900 can comprise an activation switch such as the switch 3565, which can be used to activate the sound transducer 3567 or the housing 4900 generally. In some aspects, as shown, the arm 3510 can define a rectangular shape in cross-section. In other aspects, as shown in FIG. 40, the arm 3510 can define a circular shape in cross-section. In other aspects, the arm 3510 can define a non-rectangular and non-circular shape in cross-section.

Figure 45:
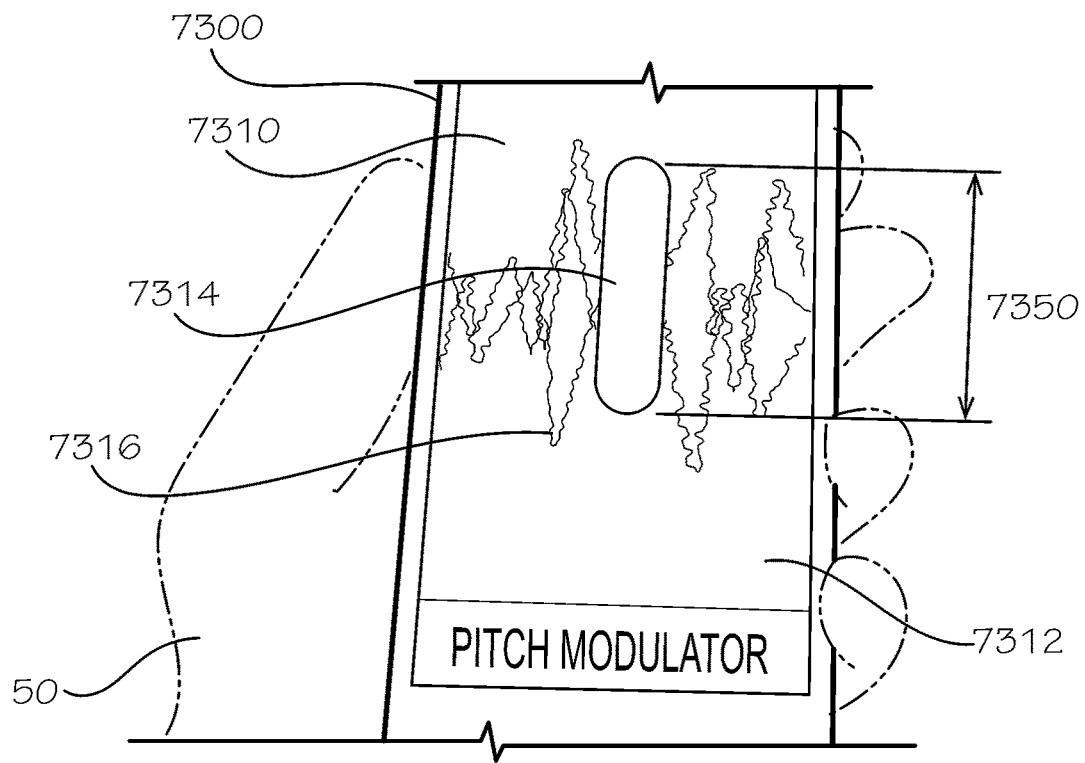
FIG. 45 is a perspective view of a portable electronic device for use with a speech assistance device in accordance with another aspect of the current disclosure, the portable electronic device defining a graphical user interface in a first condition.

As with the device 100 shown in FIGS. 33-37, the housing 4900 can be placed in contact with the neck 52 of the user during use. In other aspects, the housing 4900 can be placed in contact with the cheek 54 of the user. In other aspects, the housing 4900 can be placed in contact with another portion of the user 50. In each location, the housing 4900 can be configured to contact the neck 52 of the user 50 and transmit vibrations to the oral cavity of the user 50. In some aspects, the user 50 can cause the housing 4900 to contact the desired surface by manually pressing the housing 4900 against the desired body surface with hand pressure. In other aspects, the user 50 can create the same contact with the housing 4900 by moving his or her head such that the desired body surface presses up against the housing 4900, with or without manual hand pressure. In other aspects, the housing 4900 can be made to contact the desired body surface by the incorporation of a biasing element (not shown). For example and without limitation, a biasing element can cause the arm 3510 and the housing 4900 to naturally bend or rotate, e.g., in an Y-axis direction towards the user 50. The biasing element can comprise a spring or a portion of the device 100 such as the arm 3510 can be formed from an inherently elastic material and the arm 3510 can be pre-bent—or bent by the user 50—to push up against a body surface such as the neck with manual hand or other pressure. In other aspects, the user 50 can activate the housing 4900 by remote activation with a portable electronic device 7300 such as is shown in FIG. 45.

Figure 41:
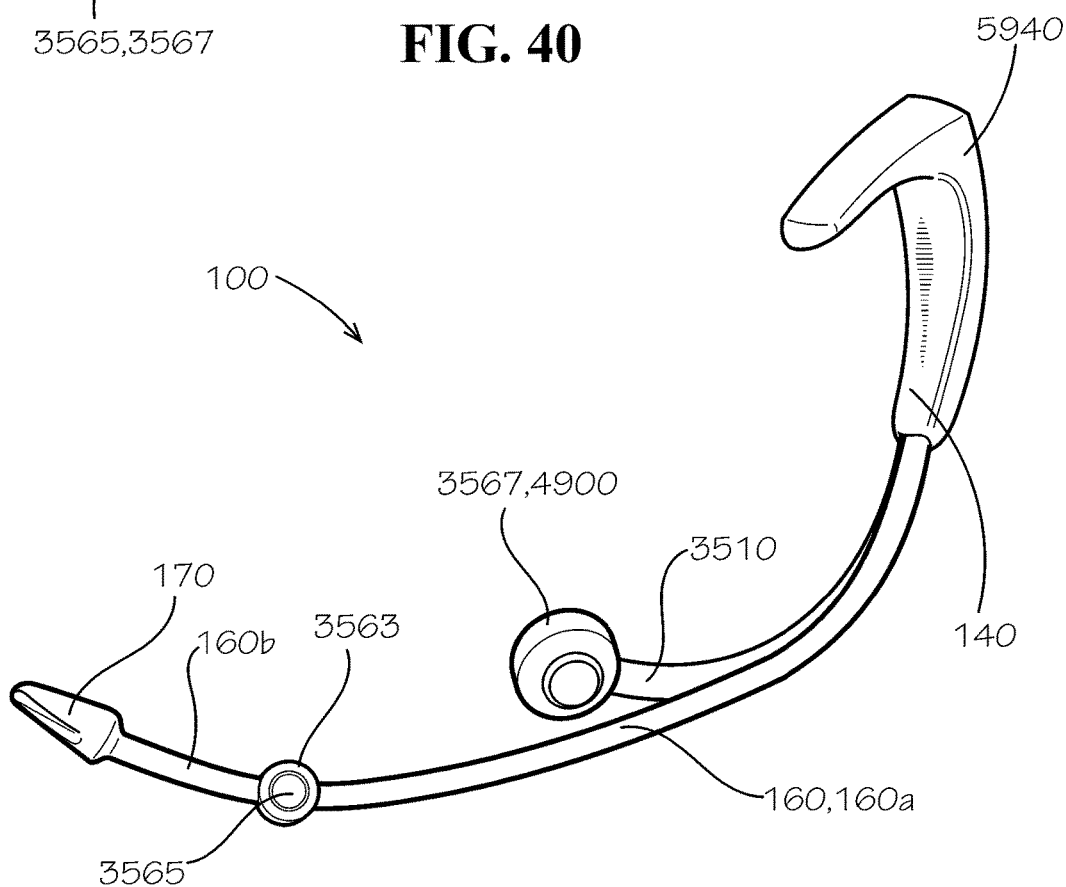
FIG. 41 is a speech assistance device in accordance with another aspect of the current disclosure.

In some aspects, features of the device 100 shown in FIGS. 33-37 can be combined with features of the device 100 shown in FIGS. 27-32 such that, as shown in FIG. 41, the user 40 can use, for example and without limitation, either the tube 160 (shown in FIG. 27) or the sound transducer 3567 (shown in FIG. 33) to produce speech.

Figure 39:
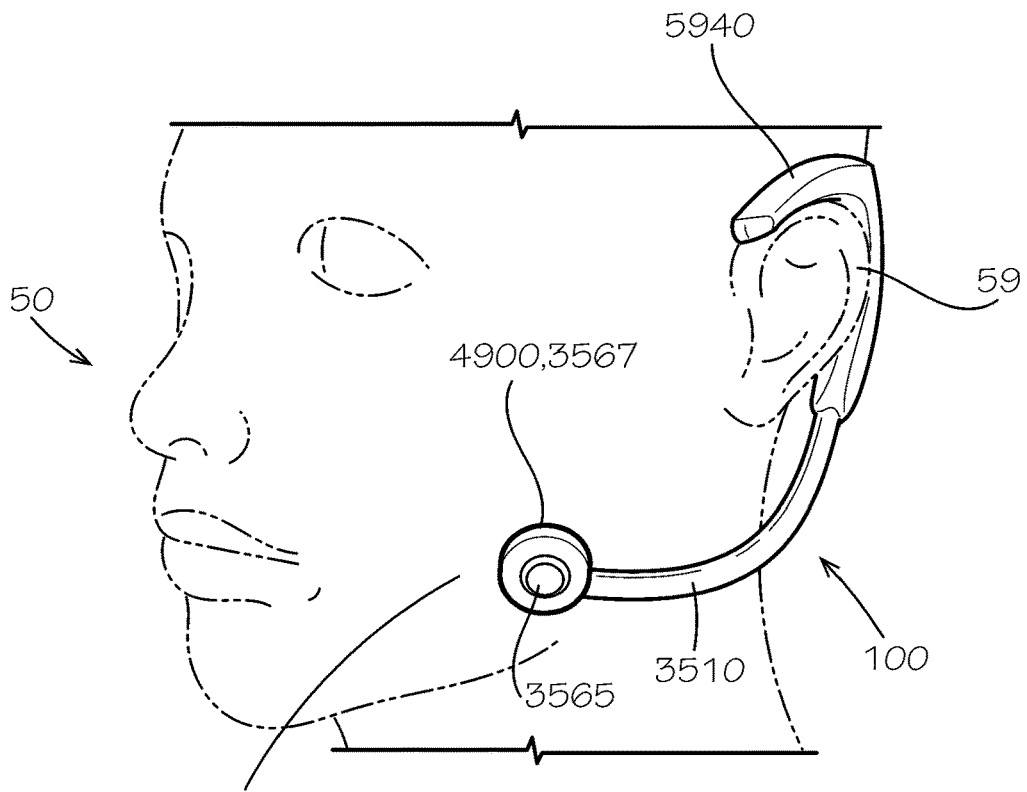
FIG. 39 is a side perspective view of the speech assistance device of FIG. 38 as worn by the user.
Figure 40:
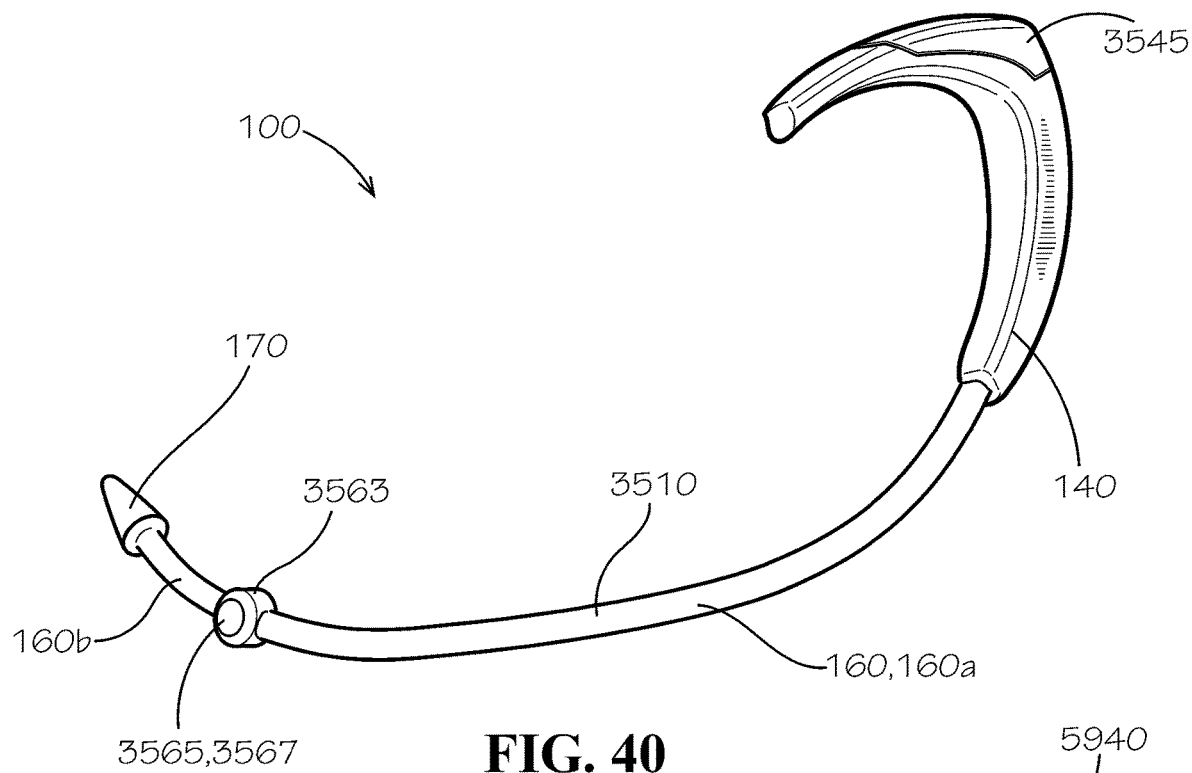
FIG. 40 is a speech assistance device in accordance with another aspect of the current disclosure.

FIG. 39 shows the device 100 of FIG. 38 as worn by the user 50—with the ear attachment hook 5940 wrapped around and secured about the ear 59 and the arm 3510 positioning the sound transducer 3567 against the cheek 54 of the user 50.

As shown in FIG. 40, the tube 160—and, more specifically, the tubes 160a,b—can be coupled to the body 140. The tube 160 can be configured to be inserted into the mouth 56 of the user 50. The cover 3530 can cover a cavity (not shown) of the body 140, which can be defined specifically in the ear attachment hook 5940 and can be sized to receive a power supply or other components for powering the device 100.

Figure 43:
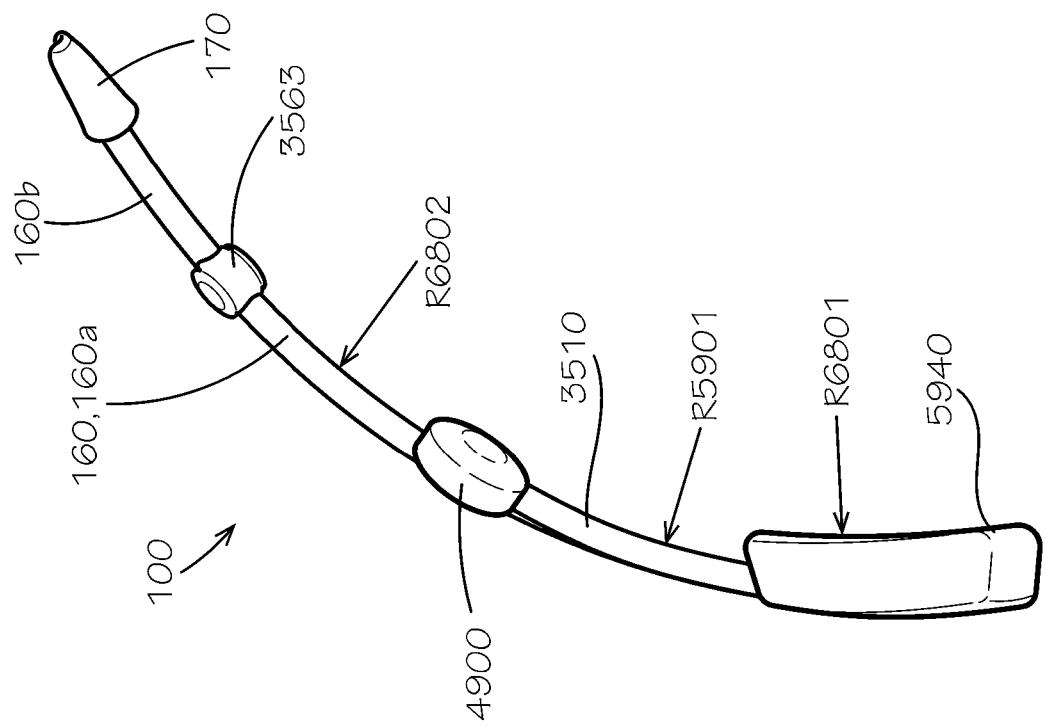
FIG. 43 is a top view of the speech assistance device of FIG. 41.
Figure 42:
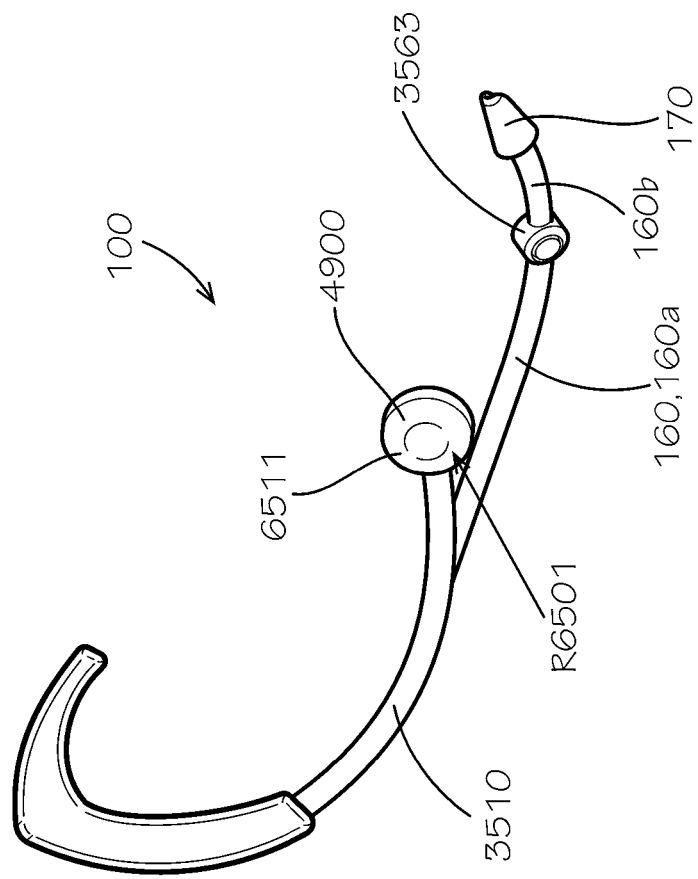
FIG. 42 is a side view of the speech assistance device of FIG. 41.

As shown in FIGS. 41-43, the device 100 can comprise both the arm 3510, which can terminate in the housing 4900, and the tube 160, which can terminate in the mouthpiece 170. The user 50 can elect to use the device by, for example, contacting the housing 4900 with a wall adjacent to the oral cavity or by inserting the mouthpiece 170 into the mouth 56. As shown in FIG. 42, the housing 4900 can define on a first surface 6511 a curved surface defining a radius R6501. As shown, the ear attachment hook 5940 and the body 140 can be asymmetric when viewed from any of multiple directions. The asymmetry of the ear attachment hook 5940 and the body 140 can facilitate secure attachment to the ear 59 of the user 50. As shown in FIG. 43, the ear attachment hook 5940 can define a radius R6801 or, as noted above, can house the batteries that can be used to power the sound transducer 3567 (not shown). Additionally, the arm 3510 can define the aforementioned radius R5901 and the tube 160 can define a radius R6802.

Figure 44:
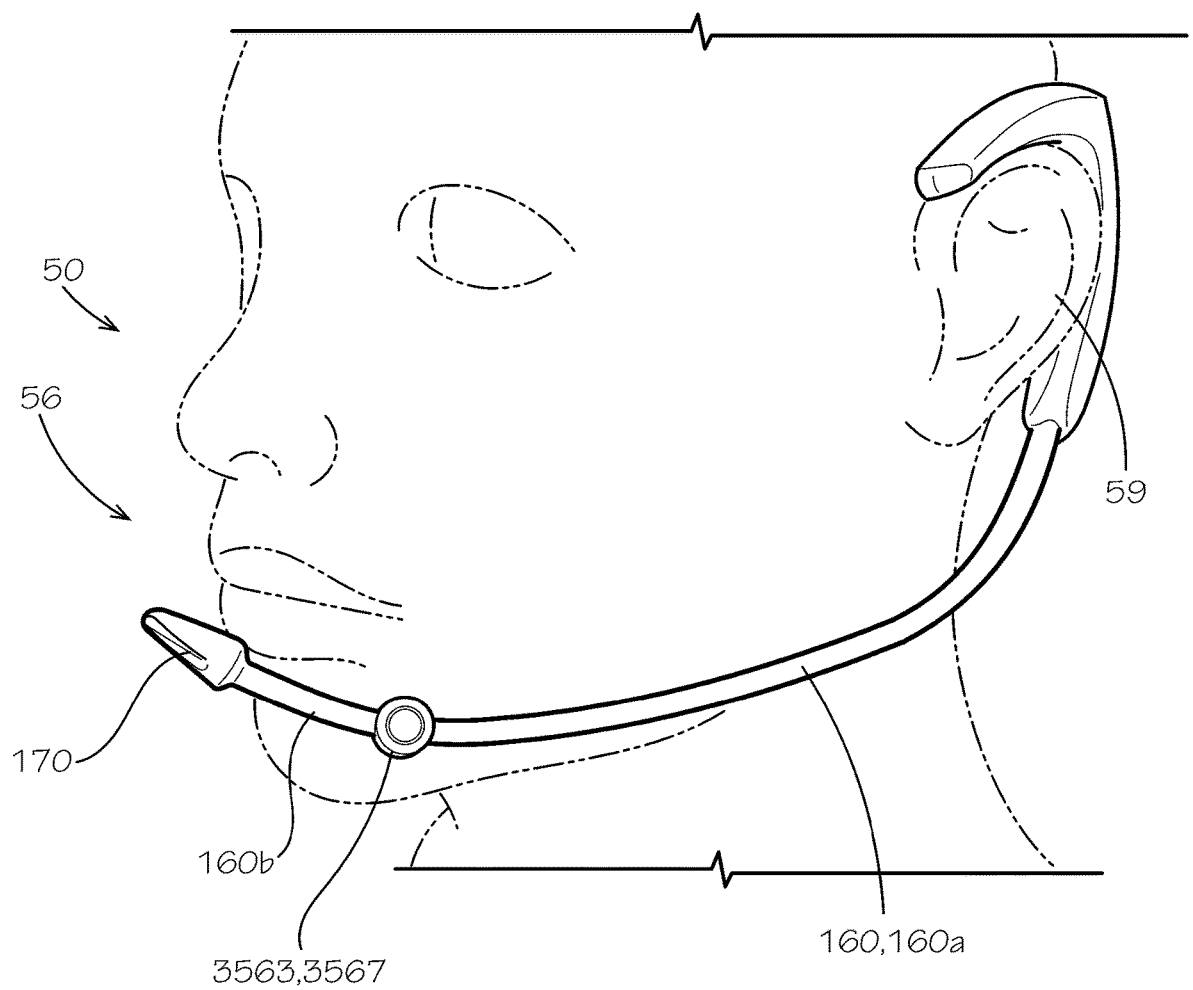
FIG. 44 is a side perspective view of the speech assistance device of FIG. 40 as worn by the user.

FIG. 44 shows the device 100 of FIG. 40 as worn by the user 50. The flexibility of the tube 160b can be such that the mouthpiece 170 can be inserted into the mouth 56 of the user 50. The device 100 of FIG. 41 can be worn similarly by the user 50.

Figure 46:
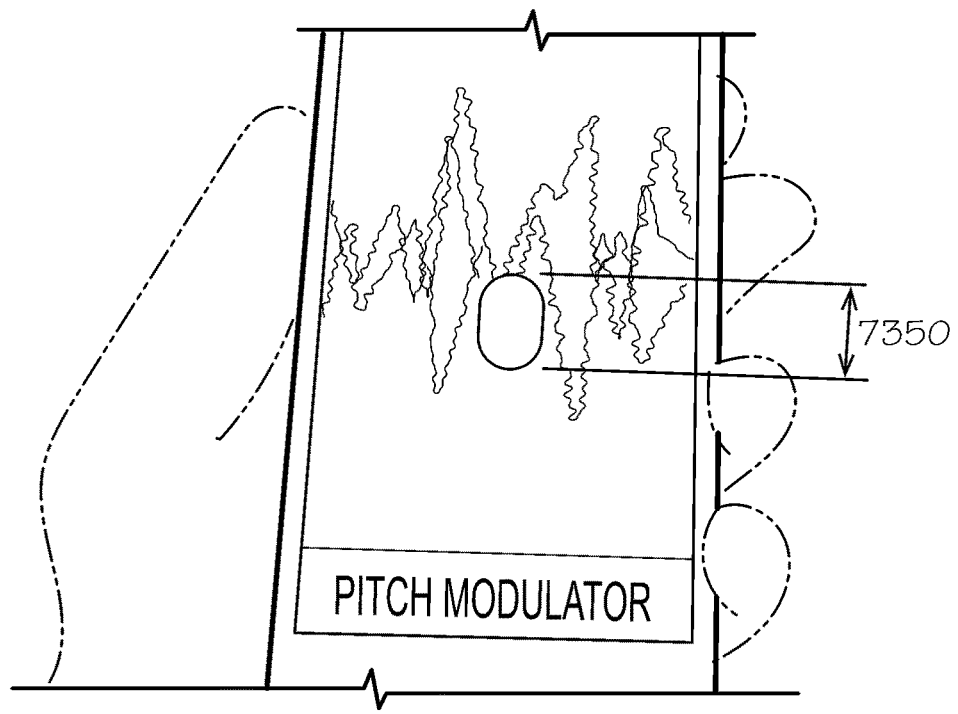
FIG. 46 is a perspective view of the portable electronic device of FIG. 45 with the graphical user interface in a second condition.

As shown in FIGS. 45 and 46, the portable electronic device 7300 can comprise a graphical user interface 7310. In some aspects, as shown, the portable electronic device 7300 can be a "smart phone" able to be held in a hand of the user 50. In other aspects, the portable electronic device 7300 can be any other electronic device. As shown in FIG. 45, in a first condition the graphical user interface 7310 can define a background 7312 on which a pitch modulation bar 7314 can be defined. A height or length 7350 of the pitch modulation bar 7314 can represent a desired pitch of assisted speech produced by the user 50 from using the device 100. The background 7312 can further define one or more waveforms 7316, each of which can be used to display any one of a number of difference sound representations such as, for example and without limitation, user-desired speech corresponding to a calibrated signal sent to the device 100 by the portable electronic device 7300 and/or actual speech produced by the user (for example, as can be picked up by a microphone of the portable electronic device 7300). As shown in a second condition of the graphical user interface 7310, the length 7350 of the pitch modulation bar 7314 can be decreased by "swiping" or otherwise manipulating— directly or indirectly—the graphical user interface 7310 with, for example and without limitation, the finger or fingers of the user 50.

In some aspects, any of the aforementioned devices 100, where powered by or comprising electronic devices configured to send or receive signals, can be configured to connect to the portable electronic device 7300 by BLUETOOTH (a federal certification mark of Bluetooth SIG, Inc.) technology or any other wireless communications technology.

The portable electronic device 7300 can be in wireless communication with the device 100, from which the device 100 can be controlled. In some aspects, the portable electronic device 7300 can be used to wirelessly activate the device 100 and specifically the housing 4900. In other aspects, the switch 3565 can be a voice onset device to initiate the production of sound by the sound transducer 3567 of the device 100. As shown, the ear attachment hook 5940 can be made adjustable to bend, stretch, or telescope in one direction or another for smaller or larger ears and other attachment methods.

The graphical user interface 7310 of the portable electronic device 7300 can define a circular jogwheel interface whereby the pitch or any other characteristic of the output from the housing 4900 can be adjusted by intuitively "spinning" or sliding the virtual wheel on the graphical user interface 7310 in a clockwise or counter-clockwise direction.

In some aspects, the device 100 can incorporate the housing 4900 into the body 140, and the ear attachment hook 5940 of the device 100 can be shaped differently and can pass in front of and over the ear 59 of the user 50.

Figure 47:
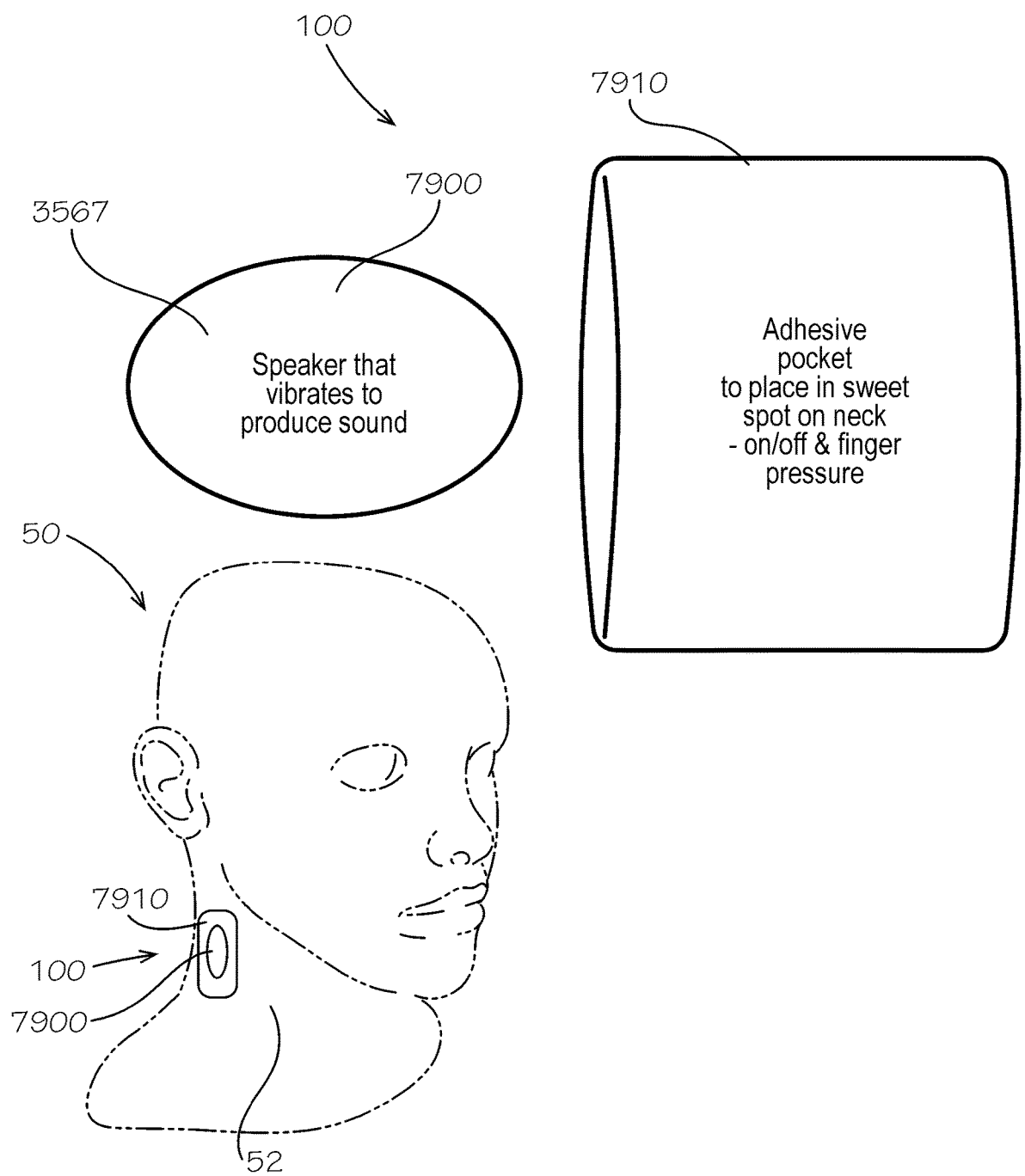
FIG. 47 is a speech assistance device in accordance with another aspect of the current disclosure, the speech assistance device comprising a neck disk.

As shown in FIG. 47, the device 100 can incorporate the same functionality as the "necklace" and "earpiece" variations of the device 100 but instead of wrapping around the neck 52 or the ear 59 of the user 50 can be a speaker disc 7900 shown. The speaker disc can be a low-profile electronic device comprising the sound transducer 3567 and able to produce vibrations like a speaker. In some aspects, the speaker disc 7900 can be held in place with a temporary adhesive cover 7910 to hold the speaker disc 7900 in a particular "sweet spot" on the neck, the location of which can depend on the unique anatomy and other physiological characteristics of the user 50. In other aspects, the temporary adhesive cover 7910 can define a pocket configured to receive the speaker disc 7900. In other aspects, the speaker disc 7900 can be held in place with a strap or other fastening device. In some aspects, the speaker disc 7900 can be activated by hand pressure. In other aspects, the speaker disc 7900, which can be in wireless communication with the portable electronic device 7300, can be activated by manipulation of the portable electronic device 7300. Like the other devices 100 incorporating the sound transducer 3567, the speaker disc 7900 can enable the user 50 to produce speech as does the aforementioned electrolarynx but in a much smaller hands-free package—except in some aspects where manual activation is desired. In some aspects, the neck disc can also be adjusted to create a better quality sound than the electrolarnyx. In some aspects, to produce the better quality sound a user's voice can be recorded before a laryngectomy to collect samples of natural speech of the user 50, and the portable electronic device 7300 can replay or continuously "loop" such a voice instead of a generic electronic sound. By the use of sound editing and other software, such a voice sample can be adjusted as desired or otherwise created even when no recording of the pre-surgery natural voice of the user 50 exists.

Figure 48:
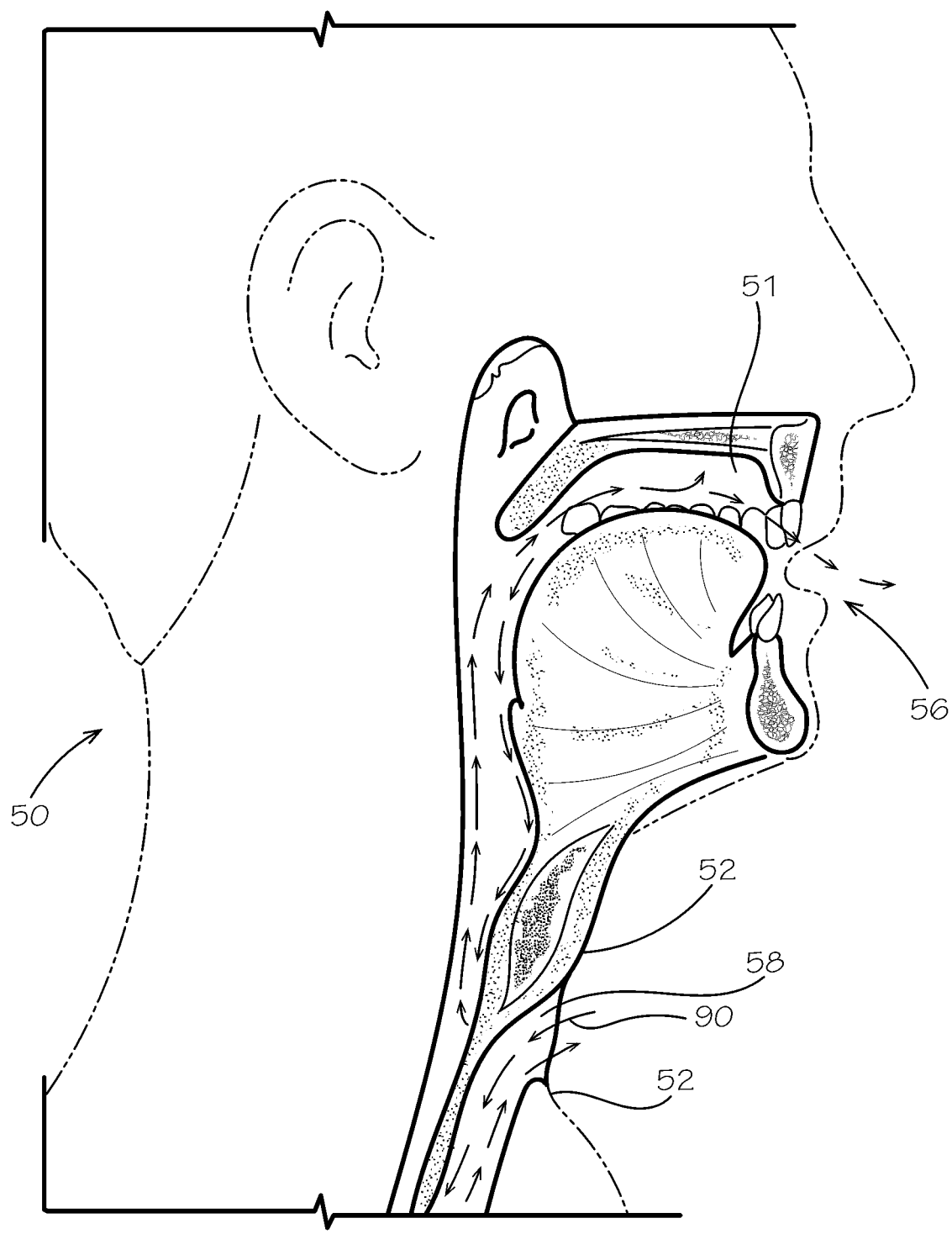
FIG. 48 is a sectional view of the head and throat of a user after a total laryngectomy, the neck of the user defining a stoma from which air can travel to and from the lungs.

FIG. 48 shows a typical laryngectomee—and the user 50—after a total laryngectomy. One position of the stoma 58, which can vary in size, shape, and position for different users 50, is shown. As shown here and previously described, the area of the neck 52 of the user 50 may be a non-flat surface against which the mating portion of the device 100 can not only reach—based on being sized to fit over the neck accessory 60—but also tightly seal based on its shape and flexibility.

A method of using the device 100 can comprise suspending a body of the device on or around the neck 52 or the ear 59 of the user 50 such as with the ear attachment hook 5940 or a "necklace" as shown in various exemplary embodiments throughout, the ear attachment hook configured to secure the body to an ear 59 of a laryngectomy patient. In some aspects, the method can comprise adjusting the tube 160 of the device 100 to reach the mouth 56 of the user 50. The method can comprise inserting the tube 160 into the mouth 56 of the user 50. The method can comprise orientating the vent 1740 of the mouthpiece 170 of the device away from the tongue of the user 50. The method can comprise producing one of vibrations and air flow in the device 100. The method can comprise propelling towards and into the mouth 56 of the user 50 one of vibrations and air flow in the device 100. In other aspects, the method can comprise adjusting the arm 3510 of the device 100 to reach a desired portion of the skin of the user 50 such as, for example and without limitation, on or proximate to the neck, check, or chin of the user 50. The method can comprise the device 100 transmitting or conducting vibrations to the oral cavity of the user 50 through skin of the user 50. The method can further comprise articulating upon the sound or vibrations inside the oral cavity of the user 50. In other aspects, the method can comprise affixing a speaker disc 7900 to the neck 52 of the user 50 and producing vibrations thereby through the skin of the user 50. In some aspects, the method can comprise activating the device 100 to produce vibrations or sound by applying pressure directly to a portion of the device 100. In other aspects, the method can comprise activating the device 100 to produce vibrations or sound by remote control of the device 100 with the portable electronic device 7300. In some aspects, the method can comprise adjusting the device 100—by any of the methods described herein—once before speech. In other aspects, the method can comprise adjusting the device 100 during speech such as by, for example and without limitation, raising the pitch during the asking of a question or otherwise adjusting the pitch or other characteristics of the speech while the speech is being produced. In some aspects, such adjustment can be made on the device 100 itself with manual rotation, depression, and/or other manipulation of an adjustment knob or wheel or other switch on the device 100.

A method of modifying the device 100 can comprise generating with the device 100 a first vibratory sound defining a first fundamental frequency. The first vibratory sound can be generated by pushing a known reference flow of air 90 through the device 100 or by the user 50 pushing air from the stoma 58 into and through the device 100, the device 100 in any case generating the first vibratory sound with a first reed module 150 incorporated therein. The method can further comprise detaching a first reed module 150 of the device 100 from the device 100. The first vibratory sound can define a first set of characteristics based on the reference flow of air 90 through the device, which can be characteristics uniquely identifying a first voice such as the first fundamental frequency, a first tonal quality, or a first pitch. The method can comprise attaching a second reed module 150 to the device 100, the second reed module 150 comprising a second reed 1300. The method can comprise covering and sealing the first end of the adaptor 110 against the stoma 58 of the user 50. The method can comprise inserting the mouthpiece 170 of the tube 160 of the device 100 into the mouth 56 of the user 50. The method can comprise generating a second vibratory sound by pushing a reference flow of air 90 through the device 100 or by the user 50 pushing air from the stoma 58 into and through the device 100. The second vibratory sound can define a second set of characteristics based on, e.g, the reference flow of air 90 through the device, which can be characteristics uniquely identifying a second voice such as the second fundamental frequency, a second tonal quality, or a second pitch. The second tonal quality different than the first tonal quality and the second pitch different than the first pitch, or the second fundamental frequency can simply differ from the first fundamental frequency. In some aspects, a user can select either the first reed module 150 or the second reed module 150 depending on the desired tonal quality and pitch.

The fundamental frequency will generally define, for example, whether a voice is high or low and typically male or female, and can be measured and can be found constant for a given configuration of the device 100 and in particular for a given reed module 150 even where the user 50 and the flow of air 90 through the device 100 varies. For reference, the fundamental frequency for an adult male human voice will generally fall within a range of 85 to 180 Hz, and the fundamental frequency for an adult female human voice will generally fall within a range of 165 to 255 Hz. The tone of the sound produced by the device 100 can nonetheless still vary depending on factors discussed above and a volume of the flow of the air 90 can vary depending on the effort utilized by the user 50 to expel the air 90 from the stoma 58.

In some aspects, as already described, the flow of air 90 expelled by the user 50 from the stoma 58 can power the device 100. In other aspects, an air source built into the device 100 or configured to mate with the device 100 and separate from the air naturally exiting the stoma 58 can power the device 100. In either case, the air source can be configured to blow air across the reed or reeds 1300. Such an air source, which can be a small fan or air pump or other air mover, can replace the adaptor 110 or mate with the adaptor 110.

Again, the reed module can be easily replaceable. Specifically, the method of detaching the first reed module 150 of the device 100 from the device 100 need not require disassembly of the first reed module 150 itself; and attaching the second reed module 150 to the device 100 in place of the first reed module 150 need not require assembly of the second reed module 150 itself. For example, the first reed module 150 can be replaceable as a unit with a second reed module 150 without the user detaching the first reed 1300 from the first reed holder 1100 or attaching a second reed 1300 to a second reed holder 1100 of the second reed module 150.

Any feature described herein such as, for example and without limitation, the indentations 960 shown in FIG. 9, can comprise both functional and aesthetic elements, and any feature described as having functional aspects can have any one of several aesthetic designs without altering the respective parts' functions.

One should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily comprise logic for deciding, with or without user input or prompting, whether these features, elements and/or steps are included or are to be performed in any particular aspect.

It should be emphasized that the above-described aspects are merely possible examples of implementations, merely set forth for a clear understanding of the principles of the present disclosure. Any process descriptions or blocks in flow diagrams should be understood as representing modules, segments, or portions of code which comprise one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described aspect(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A speech assistance device comprising:
   an adaptor defining a first end and a second end, the first end of the adaptor so dimensioned as to be able to receive and cover a heat and moisture exchange (HME) cassette secured to and protruding from a neck of a user, the HME cassette being separate from the device and secured proximate to a tracheal stoma defined in the neck of the user, the adaptor comprising a compressible material, the compressible material of the adaptor configured to compress to match and seal against a contour of the neck of the user, either directly or indirectly through one of a neck accessory and clothing positioned between the neck and the adaptor, and thereby prevent air from leaking out from between the adaptor and at least one of the neck of the user and the HME cassette;
   a reed module connected to the adaptor, the reed module comprising a reed holder and a reed, the reed configured to produce sound using air expelled by the user from the stoma; and
   a tube coupled to the reed module, the tube configured to be inserted into a mouth of the user;
   wherein the reed module is replaceable as a unit, the reed module being detachable from each of the adaptor and the tube without disassembly of the reed module or adjustment of the reed with respect to the reed holder, a second reed module comprising a second reed holder and a second reed attachable to each of the adaptor and the tube as a replacement for the reed module without assembly of the second reed module or adjustment of the second reed with respect to the second reed holder.

2. The device of claim 1, wherein the compressible material is foam.

3. The device of claim 1, further comprising a joint positioned between and connecting adjacent components of the device, the joint defining a bore allowing passage of the air expelled by the user, the joint further defining a surface preventing movement of the joint to a point where passage of the air through the bore of the joint to the adjacent components would be restricted.

4. The device of claim 1, wherein the reed module comprises a single reed configured to produce sound without any additional reeds.

5. The device of claim 1, wherein the reed module comprises at least two reeds.

6. The device of claim 1, wherein at least a portion of the reed module extends into a cavity of the adaptor.

7. The device of claim 5, wherein the reed module is positioned to direct the air expelled by the user between the at least two reeds.

8. The device of claim 1, wherein the tube comprises a mouthpiece defining a first end and a second end, the mouthpiece defining a bore sized to allow passage of air completely through the mouthpiece from the first end to the second end, the mouthpiece further defining a vent proximate to the second end of the mouthpiece, the vent defining a vent width in a transverse direction of the mouthpiece, the vent width being less than a diameter of a portion of the mouthpiece in which the vent is defined, the vent further defining a vent length extending in an axial direction from the second end of the mouthpiece.

9. A speech assistance device comprising:
   a monolithic body comprising a first end defining a first opening and a second end defining a second opening, the monolithic body defining a reed module cavity between the first opening and the second opening;
   a reed module positioned within the reed module cavity of the body, the reed module comprising a reed holder and a reed, the reed module also sealed within the reed module also sealed and positioned fully within the reed module cavity of the body, a diameter of the reed module being greater than a diameter of the first opening and greater than a diameter of the second opening; and
   an adaptor defining a first end and a second end, the first end of the adaptor so dimensioned as to be able to receive and cover a heat and moisture exchange (HME) cassette secured to and protruding from a neck of a user, the HME cassette being separate from the device and secured proximate to a tracheal stoma defined in the neck of the user, the adaptor comprising a compressible material, the compressible material of the adaptor configured to compress to match a contour of the neck of the user and thereby prevent air from leaking out from between the adaptor and at least one of the neck of the user and the HME cassette.

10. The device of claim 9, wherein the monolithic body comprises a tube configured to be inserted into a mouth of a user.

11. The device of claim 9, wherein the reed module comprises at least two reeds.

12. The device of claim 10, wherein the tube comprises a mouthpiece defining a first end and a second end, the mouthpiece defining a bore sized to allow passage of air completely through the mouthpiece from the first end to the second end, the mouthpiece further defining a vent proximate to the second end of the mouthpiece, the vent defining a vent width in a transverse direction of the mouthpiece, the vent width being less than a diameter of a portion of the mouthpiece in which the vent is defined, the vent further defining a vent length extending in an axial direction from the second end of the mouthpiece.

13. A method of using a speech assistance device, the method comprising:

receiving within an adaptor of the device and covering with the device a heat and moisture exchange (HME) cassette secured to and protruding from a neck of a user, the HME cassette being separate from the device and secured proximate to a tracheal stoma defined in the neck of the user;

sealing against leakage of air traveling from a tracheal stoma defined in the neck of the user into the device at a connection between a first end of the adaptor of the device and at least one of the neck of the user and the HME cassette;

generating with the device a first vibratory sound defining a first fundamental frequency, the device generating the first vibratory sound with a first reed module incorporated therein, the first reed module comprising a first reed holder and a first reed secured to the first reed holder, the device further comprising:

the adaptor defining the first end and a second end, the first reed module connected to the adaptor; and a tube connected to the first reed module, the tube configured to be inserted into a mouth of a user;

detaching the first reed module of the device from the device; and attaching a second reed module to the device in place of the first reed module, the second reed module comprising a second reed holder and a second reed secured to the second reed holder;

wherein detaching the first reed module of the device from the device does not require disassembly of the first reed module itself or adjustment of the first reed with respect to the first reed holder; and attaching the second reed module to the device in place of the first reed module does not require assembly of the second reed module itself or adjustment of the second reed with respect to the second reed holder.

14. The method of claim 13, wherein inserting the tube of the device into the mouth of the user comprises inserting a mouthpiece of the tube of the device into the mouth of the user, the mouthpiece defining a first end and a second end, the mouthpiece defining a bore sized to allow passage of air completely through the mouthpiece from the first end to the second end, the mouthpiece further defining a vent proximate to the second end of the mouthpiece, the vent defining a vent width in a transverse direction of the mouthpiece, the vent width being less than a diameter of a portion of the mouthpiece in which the vent is defined, the vent further defining a vent length extending in an axial direction from the second end of the mouthpiece.

15. The method of claim 13, further comprising:

detaching the first reed module of the device from the device;

attaching a second reed module to the device in place of the first reed module, the second reed module comprising a second reed; and generating a second vibratory sound defining a second fundamental frequency, the device generating the second vibratory sound with the second reed module incorporated therein, the second fundamental frequency differing from the first fundamental frequency.

16. The method of claim 15, wherein:

detaching the first reed module of the device from the device does not require disassembly of the first reed module itself; and attaching the second reed module to the device in place of the first reed module does not require assembly of the second reed module itself.

17. The device of claim 1, wherein a cavity defined in the adaptor is so dimensioned as to be able to receive the HME cassette, the cavity defining a cylindrical shape.

18. The method of claim 13, wherein the adaptor comprises a compressible material, the method further comprising compressing the adaptor of the device to match a contour of the neck of the user, either directly or indirectly through one of a neck accessory and clothing positioned between the neck and the adaptor, by adjusting a thickness of the compressible material to prevent air from leaking out from between the adaptor and the at least one of the neck of the user and the HME cassette.

19. The method of claim 13, further comprising squeezing and deforming a portion of a body of the device housing the first reed module to generate a second vibratory sound defining a second fundamental frequency, the second fundamental frequency differing from the first fundamental frequency.

20. The device of claim 9, wherein the compressible material is foam.

21. The device of claim 9, wherein one of an outer surface and an inner surface of the reed holder defines a cylindrical shape.

* * * * *